(12) United States Patent
Ertl et al.

(10) Patent No.: US 11,207,402 B2
(45) Date of Patent: *Dec. 28, 2021

(54) CONSTRUCTS FOR ENHANCING IMMUNE RESPONSES

(71) Applicant: THE WISTAR INSTITUTE OF ANATOMY AND BIOLOGY, Philadelphia, PA (US)

(72) Inventors: Hildegund C. J. Ertl, Villanova, PA (US); Marcio O. Lasaro, Maple Shade, NJ (US); Luis C. S. Ferreira, Sao Paulo (BR)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 213 days.

This patent is subject to a terminal disclaimer.

(21) Appl. No.: 16/408,730

(22) Filed: May 10, 2019

(65) Prior Publication Data

US 2019/0275143 A1    Sep. 12, 2019

Related U.S. Application Data

(63) Continuation of application No. 15/639,296, filed on Jun. 30, 2017, now Pat. No. 10,328,146, which is a
(Continued)

(51) Int. Cl.
*A61K 39/245* (2006.01)
*A61K 39/12* (2006.01)
(Continued)

(52) U.S. Cl.
CPC ............ *A61K 39/245* (2013.01); *A61K 39/12* (2013.01); *C07K 14/005* (2013.01); *C12N 7/00* (2013.01);
(Continued)

(58) Field of Classification Search
None
See application file for complete search history.

(56) References Cited

U.S. PATENT DOCUMENTS

| 5,814,486 A | 9/1998 | Cohen et al. |
| 6,936,255 B1 | 8/2005 | Wettendorff et al. |
| (Continued) | | |

FOREIGN PATENT DOCUMENTS

| EP | 1336619 A2 | 8/2003 |
| WO | 2006120034 A1 | 11/2006 |
| WO | 2007071997 A2 | 6/2007 |

OTHER PUBLICATIONS

Altstein, et al.,Immunization with influenza A NP-Expressing Vaccinia Virus Recombinant Protects Mice Against Experimental Infection with Hyuman and Avian Influenza Viruses, Archives of Virology, vol. 151, No. 5, May 2006, pp. 921-931.
(Continued)

*Primary Examiner* — Michelle S Horning
(74) *Attorney, Agent, or Firm* — Saul Ewing Arnstein & Lehr LLP; Kathryn Doyle

(57) ABSTRACT

Chimeric protein constructs including a herpesvirus glycoprotein D (gD) and a heterologous polypeptide that interact with herpes virus entry mediator (HVEM) and enhance and enhance an immune response against the heterologous polypeptide and methods for their use are provided.

9 Claims, 36 Drawing Sheets

Specification includes a Sequence Listing.

Related U.S. Application Data continuation of application No. 14/628,784, filed on Feb. 23, 2015, now Pat. No. 9,724,406, which is a continuation of application No. 13/239,771, filed on Sep. 22, 2011, now Pat. No. 8,962,816, which is a continuation of application No. 12/438,889, filed as application No. PCT/US2007/018939 on Aug. 28, 2007, now abandoned.

(60) Provisional application No. 60/840,526, filed on Aug. 28, 2006.

(51) Int. Cl.
 C07K 14/005 (2006.01)
 C12N 7/00 (2006.01)
 A61K 39/00 (2006.01)

(52) U.S. Cl.
 CPC ...... A61K 2039/53 (2013.01); A61K 2039/57 (2013.01); C07K 2319/00 (2013.01); C07K 2319/10 (2013.01); C12N 2710/10043 (2013.01); C12N 2710/16622 (2013.01); C12N 2710/16634 (2013.01); Y02A 50/30 (2018.01)

(56) References Cited

U.S. PATENT DOCUMENTS

| | | | |
|---|---|---|---|
| 8,962,816 B2* | 2/2015 | Ertl | A61K 39/12 536/23.1 |
| 9,624,510 B2 | 4/2017 | Ertl et al. | |
| 9,724,406 B2 | 8/2017 | Ertl et al. | |
| 10,328,146 B2* | 6/2019 | Ertl | A61K 39/245 |
| 2004/0253210 A1 | 12/2004 | Robert-Guroff et al. | |
| 2005/0095270 A1 | 5/2005 | Staecker et al. | |
| 2013/0315871 A1 | 11/2013 | Roy et al. | |
| 2014/0065105 A1 | 3/2014 | Wilson et al. | |
| 2014/0248305 A1 | 9/2014 | Ertl et al. | |

OTHER PUBLICATIONS

Alves, et al.,Antibody Response in Mice Immunized with a Plasmid DNA Encoding the Colonization Factor Antigen I of Enterotoxigenic *Escherichia coli*, FEMS Immunology Medical Microbiology, vol. 23, No. 4, Apr. 1999, pp. 321-330.
Chen, et al.,"Direct Observation of Xe and Kr Adsorption in a Xe-Selective Microporous Metal-Organic Framework.", J. Am. Chem. Soc. 2015, 137, 7007-7010.
Hazama, et al.,Adjuvant-independent enhanced immune responses to recombinant Herpes Simplex Virust Type 1 Glycoprotein D by fusion biologically active interlukin-2, Vaccine, vol. 11, No. 6, 1993, pp. 629-636.
Hinuma, et al.,A novel strategy for converting recombinant viral protein into high immunogeic antigen, FEBS Letters, vol. 288, No. 1/2, Aug. 1991, pp. 138-142.
Lasaro, et al.,Antibody-inducing properties of a prototype bivalent Herpes Simplex virus/Enterotoxigenic *Escherichia coli* DNA Vaccine, FEMS Immunology and Medical Microbiology, vol. 35, No. 1, Jan. 21, 2003, pp. 25-31.
Lasaro, et al.,Anti-Tumor DNA Vaccines based on the Expressiopn of Human Papillomavirus-16 E6/E7 Oncoproteins Genetically Fused With The Glycoprotein D from Herpes Simplex Virus-1, Microbes and Infection, vol. 7, No. 15, Dec. 2005, pp. 1541-1550.
Lasaro, et al.,Human papillomavirus-associated cervical cancer: Prophylactic and therapeutic vaccines., Gene Therapy Molecular Biology, 2004, vol. 8, pp. 291-306.
Michel, et al.,Enhanced Immunogenicity of HPV 16 E7 Fusion Proteins in DNA Vaccination, Virology, 2002, vol. 294, pp. 47-59.
Plonka, et al., "Light Hydrocarbon Adsorption Mechanisms in Two Calcium-Based Microporous Metal Organic Frameworks.", Chem. Mater. 2016, 28, 1636-1646.
Saha, et al.,A Fused Gene of Nucleoprotein (NP) and Herpes Simplex Virus Genes (VP22) Induces Highly Protective Immunity Against Different Subtypes of Influenza Virus, Virology, vol. 354, No. 1, Oct. 10, 2006, pp. 48-57.
Watson, et al.,Herpes Simplex Virus Type=1 Glycoprotein D Gene: Nucleotide Sequence and Expression in *Escherichia coli*, Science, vol. 218, Oct. 22, 1982, pp. 381-384.
Zago, et al.,Use of herpes simplex virus and pseudorabies virus chimeric glycoprotein D molecules to identify regions critical for membrane fusion., PNAS, 2004, vol. 101, No. 50, pp. 17498-17503.
European Search Report, EP17837398, dated Apr. 20, 2020.
International Search Report and Written Opinion, PCT/US17/43315, dated Nov. 30, 2017.
International Search Report, PCT/US2007/018939, dated May 16, 2008.
Singapore Search Report, SG Application No. 11201900808S, dated Apr. 29, 2020.
Bayer, et al., "Improved vaccine protection against retrovirus infection after co-administration of adenoviral vectors encoding viral antigens and type I interferon subtypes", 2011 Retrovirology 8:75 (15 pages).
Casimiro, et al., "Attenuation of simian immunodeficiency virus SIVmac239 infection by prophylactic immunization with DNA and recombinant adenoviral vaccine vectors expressing Gag", 2005, J Virol 79(24):15547-15555.
Casimiro, et al., "Comparative Immunogenicity in Rhesus Monkeys of DNA Plasmid, Recombinant Vaccinia Virus, and Replication-Defective Adenovirus Vectors Expressing a Human Immunodeficiency Virus Type 1 gag Gene", 2003, J Virol 77(11):6305-5313.
Cervasi, et al., "Immunological and Virological Analyses of Rhesus Macaques Immunized with Chimpanzee Adenoviruses Expressing the Simian Immunodeficiency Virus Gag/Tat Fusion Protein and Challenged Intrarectally with Repeated Low Doses of SIVmac", Journal of Virology, 87(17), Sep. 2013, 9420-9430.
Chawla, et al., "Adenovirus-vectored vaccines", Dev Biol Stand, Mar. 16, 2008, vol. 18, No. 3, pp. 293-307, Table 1.
Chen, et al., "Adenovirus-Based Vaccines: Comparison of Vectors from Three Species of Adenoviridae", 2010, Journal of Virology 84(20):10522-32.
Engram, et al., "Vaccine-induced, simian immunodeficiency virus-specific CD8+ T cells reduce virus replication but do not protect from simian immunodeficiency virus disease progression", 2009, J Immunol 183:706-717.
He, et al., "A simplified system for generating recombinant adenoviruses", 1998, PNAS 95:2509-14.
Horwitz, "Function of adenovirus E3 proteins and their interactions with immunoregulatory cell proteins", 2004, J Gene Med 6:S172-S183 (Abstract only).
Lasaro, et al., "New insights on adenovirus as vaccine vectors", Molecular Therapy, vol. 17, No. 8, Aug. 1, 2009, pp. 1333-1339.
Lasaro, et al., "Vaccine-induced T cells Provide Partial Protection Against High-dose Rectal SIVmac239 Challenge of Rhesus Macaques", Molecular Therapy, 19(2), Feb. 2011, 417-426.
Lewis, et al., "Response of a simian immunodeficiency virus (SIVmac251) to raltegravir: a basis for a new treament for simian AIDS and an animal model for studying lentiviral persistence during antiretroviral therapy", Retrovirology, 7(21), 2010, 1-19.
Lichtenstein, et al., "Functions and mechanisms of action of the adenovirus E3 proteins", 2004, International Reviews of Immunology 23: 75-111.
McCoy, et al., "Effect of Preexisting Immunity to Adenovirus Human Serotype 5 Antigens on the Immune Responses of Nonhuman Primates to Vaccine Regimens Based on Human- or Chimpanzee-Derived Adenovirus Vectors", Journal of Virology, 81(12), Jun. 2007, 6594-6604.
Patel, et al., "DNA and virus particle vaccination protects against acquisition and confers control of viremia upon heterologous simian immunodeficiency virus challenge", PNAS, 110(8), Feb. 2013, 2975-2980.
Santra, et al., "Heterologous Prime/Boost Immunizations of Rhesus Monkeys Using Chimpanzee Adenovirus Vectors", Vaccine, 27(42), Sep. 2009, 5837-5845.

(56) References Cited

OTHER PUBLICATIONS

Shiver, et al., "Replication-incompetent adenoviral vaccine vector elicits effective anti-immunodeficiency-virus immunity", 2002, Nature 415:331-335.
Small, et al., "Viruses—From Pathogens To Vaccine Carriers", Curr. Opin. Virol., 1(4), Oct. 2011, 241-245.
Tatsis, et al., "Adenovirus Vector-Induced Immune Responses in Nonhuman Primates: Responses to Prime Boost Regimens", Journal of Immunology, 182, 2009, 6587-6599.
Tatsis, et al., "Chimpanzee-origin adenovirus vectors as vaccine", 2006, Gene Therapy 13:421-429.
Tatsis, et al., "Multiple Immunizations with Adenovirus and MVA vectors improve CD8+ T cell functionality and mucosal homing", Virology, 367(1), Oct. 2007, 156-167.
Xiang, "Chimpanzee Adenovirus Antibodies in Humans, Sub-Saharan Africa", 2006, Emerging Infectious Diseases 12(10):1596-1599.
Zhou, et al., "A Universal Influenza A Vaccine Based on Adenovirus Expressing Matrix-2 Ectodomain and Nucleoprotein Protects Mice from Lethal Challenge", Molecular Therapy, 18(12), Dec. 2010, 2182-2189.
Zhou, et al., "An efficient method of directly cloning chimpanzee adenovirus as a vaccine vector", Natl. Protoc., 5(11), Nov. 2010, 1775-1785.
Zolla-Pazner, et al., "Analysis of V2 Antibody Responses Induced in Vaccinees in the ALVAC/AIDSVAX HIV-1 Vaccine Efficacy Trial", PLOS ONE, 8(1), Jan. 2013, 1-11.

* cited by examiner

FIG. 6
pgDE7
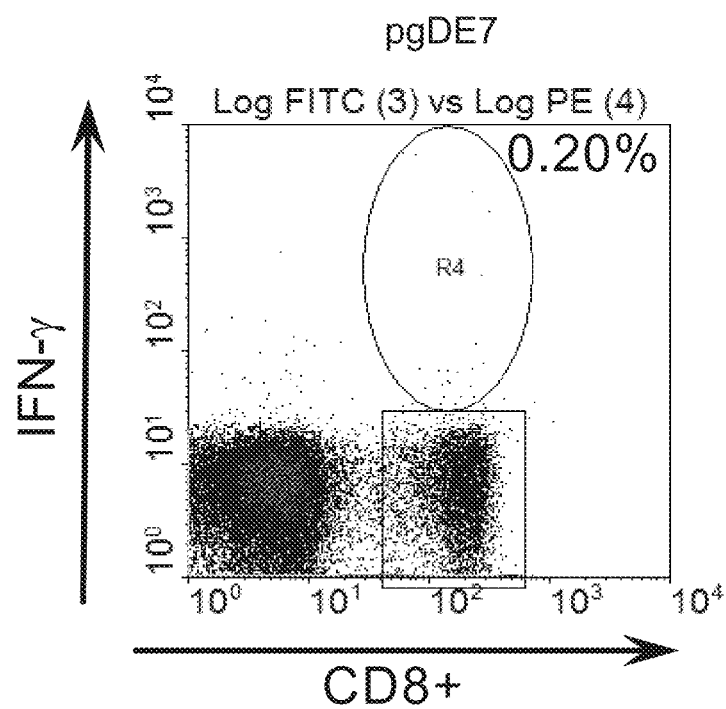
pSgDE7
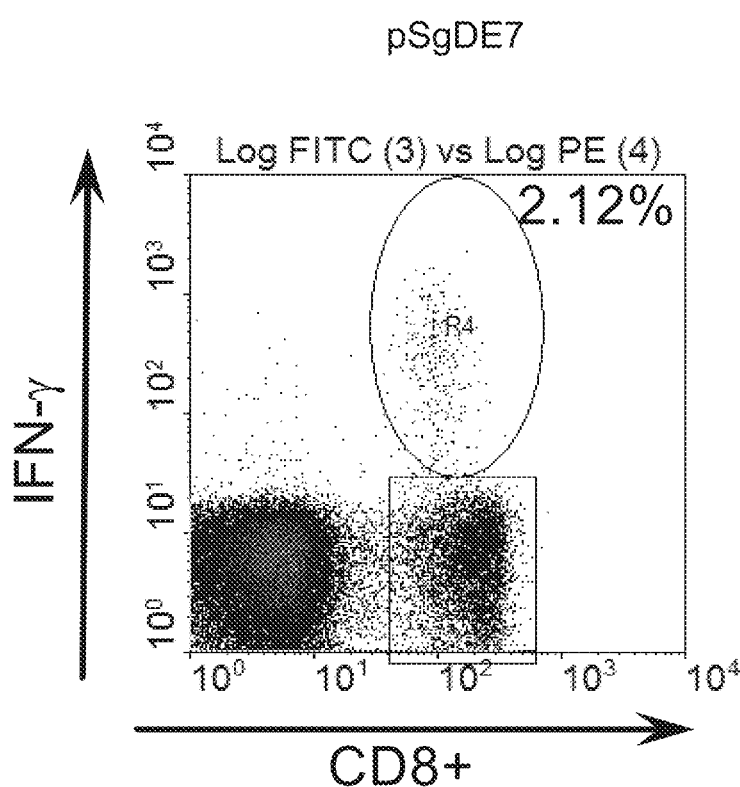

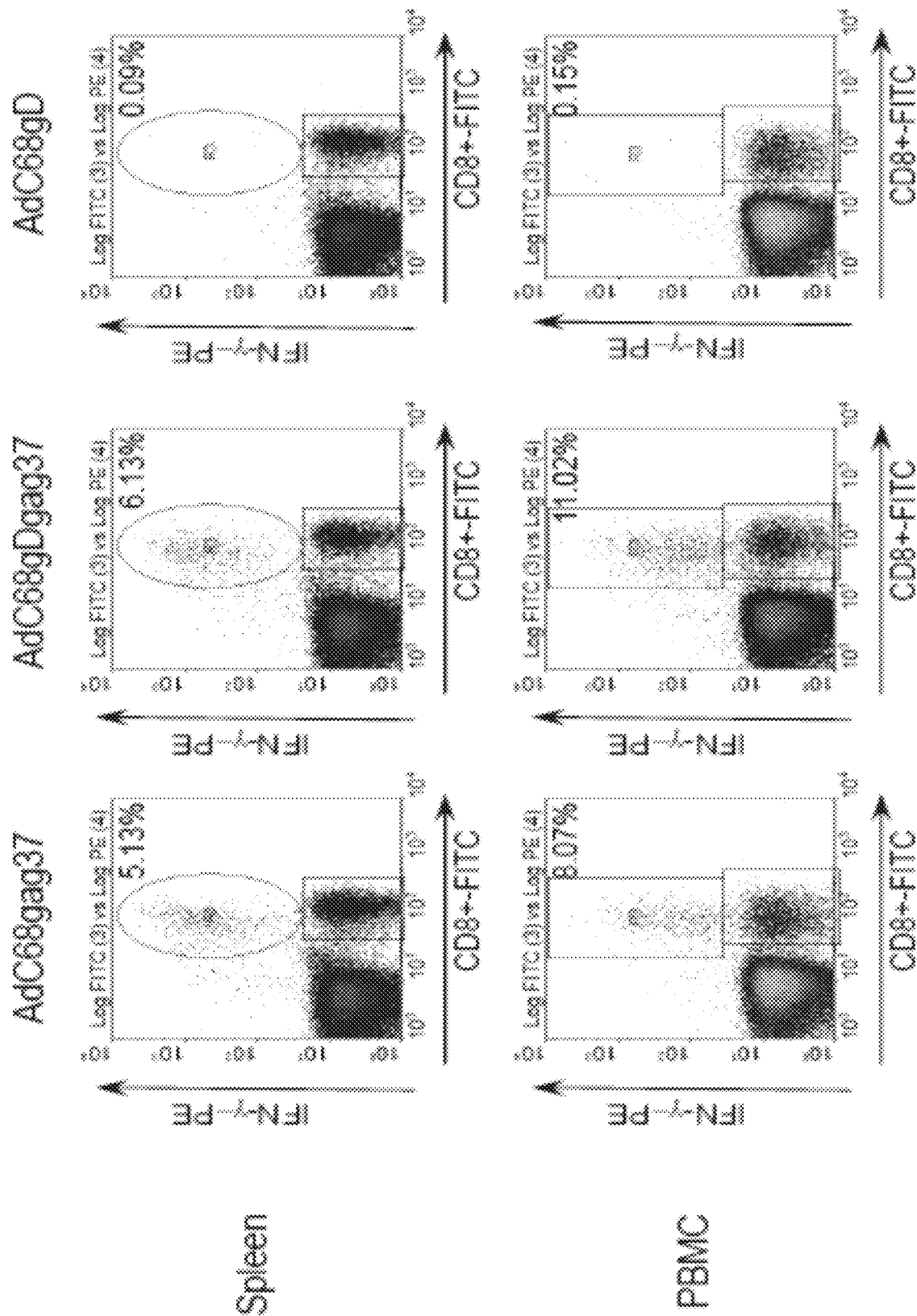

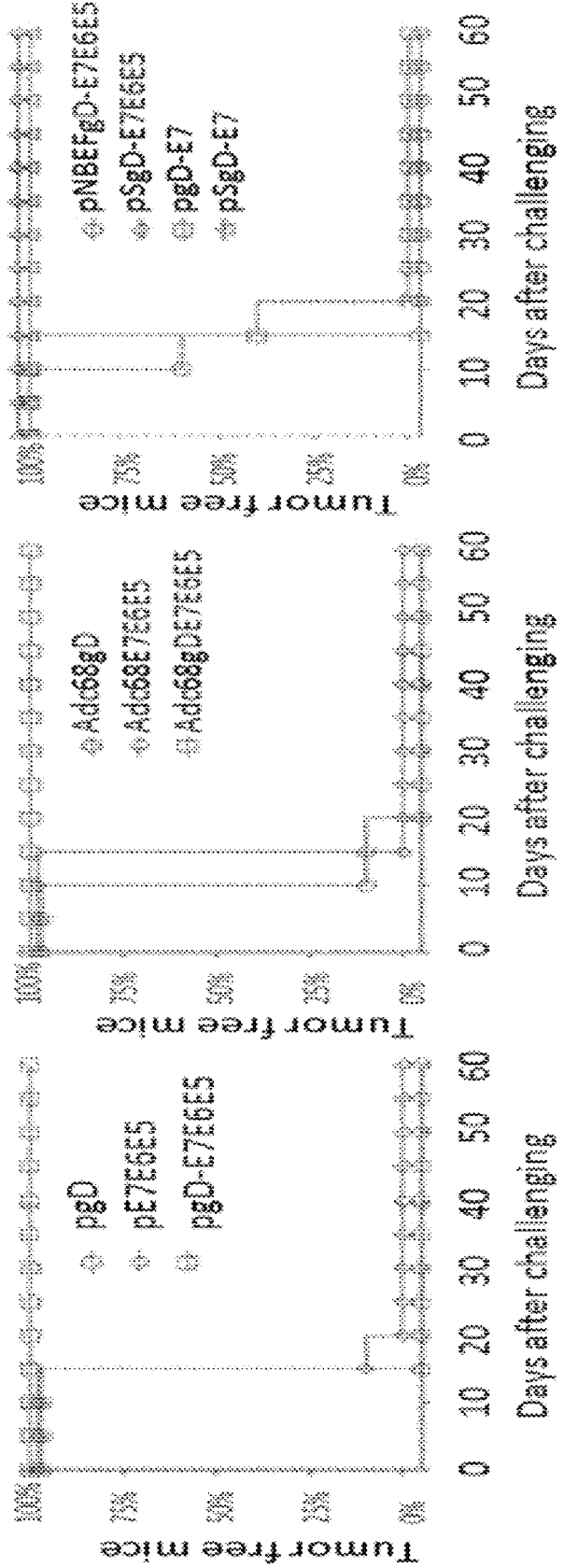

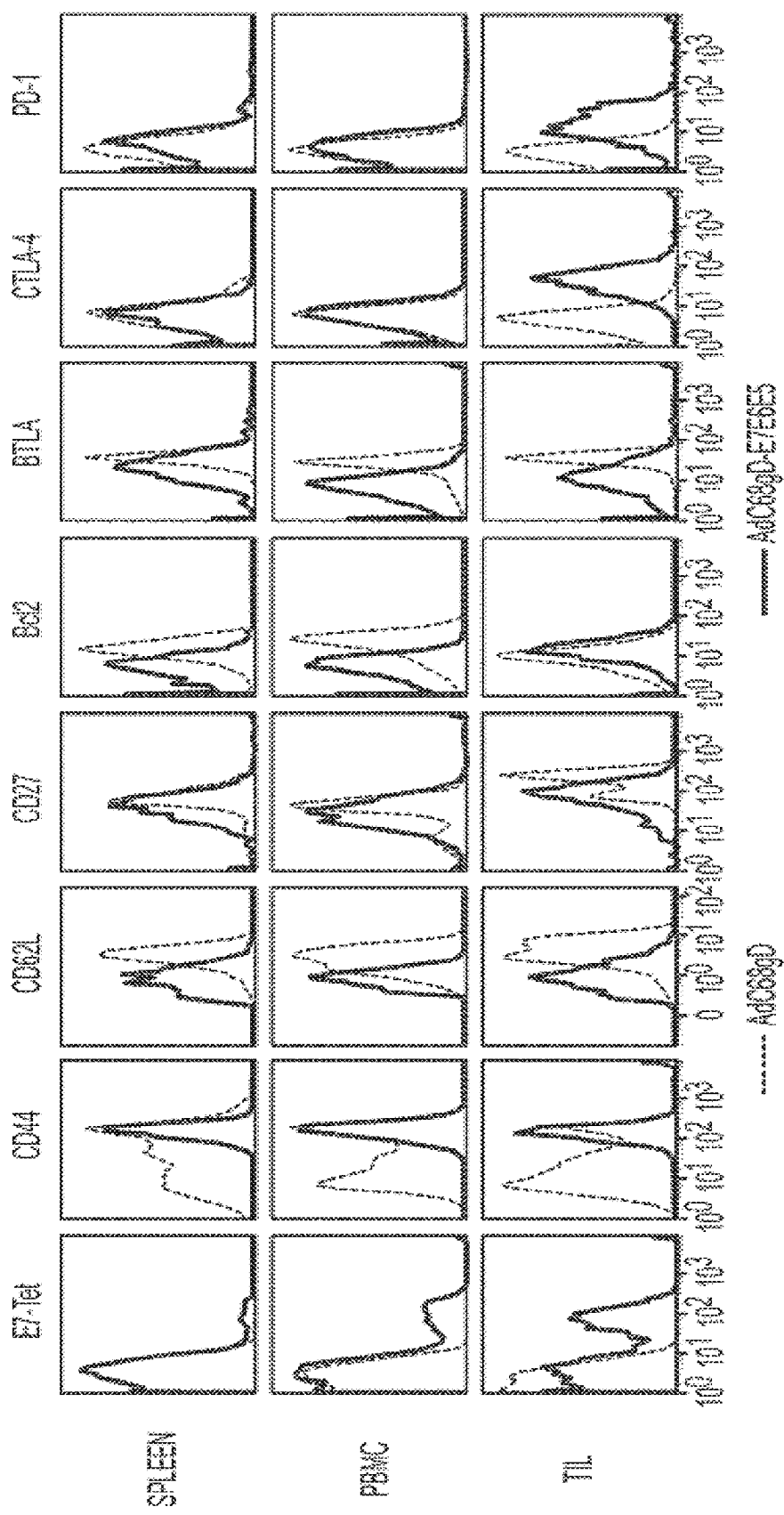

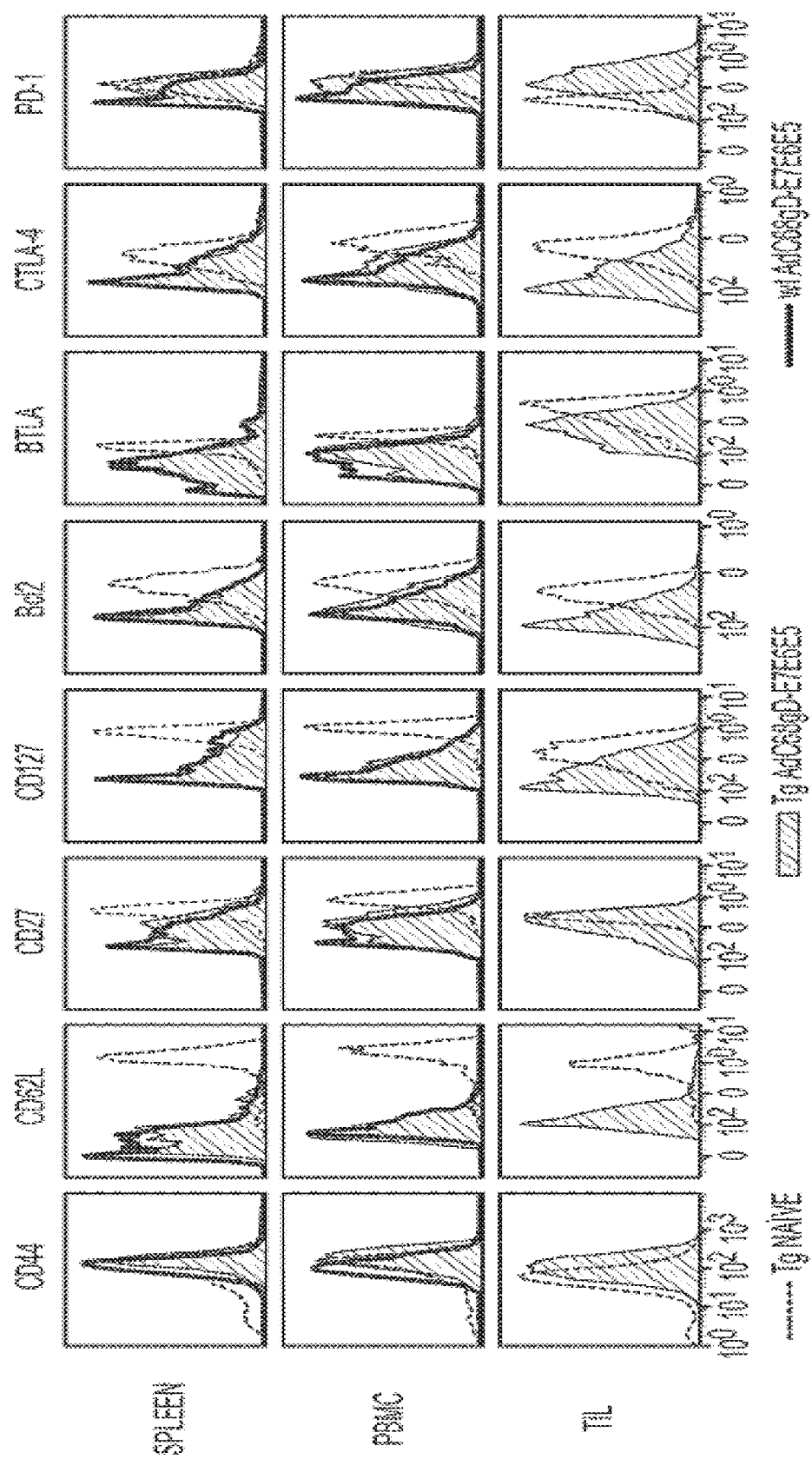

SEQUENCE LISTING

<160> NUMBER OF SEQ ID NOS: 37

<210> SEQ ID NO 1
<211> LENGTH: 29
<212> TYPE: DNA
<213> ORGANISM: Artificial Sequence
<220> FEATURE:
<223> OTHER INFORMATION: primer

<400> SEQUENCE: 1
gctgtagggc cccatggaga tacacctac                29

<210> SEQ ID NO 2
<211> LENGTH: 28
<212> TYPE: DNA
<213> ORGANISM: Artificial Sequence
<220> FEATURE:
<223> OTHER INFORMATION: primer

<400> SEQUENCE: 2
catggtggcg cctggtttct gagaacag                 28

<210> SEQ ID NO 3
<211> LENGTH: 29
<212> TYPE: DNA
<213> ORGANISM: Artificial Sequence
<220> FEATURE:
<223> OTHER INFORMATION: primer

<400> SEQUENCE: 3
agacatggcg cccaccaaaa gagaactgc                29

<210> SEQ ID NO 4
<211> LENGTH: 33
<212> TYPE: DNA
<213> ORGANISM: Artificial Sequence
<220> FEATURE:
<223> OTHER INFORMATION: primer

<400> SEQUENCE: 4
ctccatgcgg ccgcccagct gggtttctct acg                                33

<210> SEQ ID NO 5
<211> LENGTH: 32
<212> TYPE: DNA
<213> ORGANISM: Artificial Sequence
<220> FEATURE:
<223> OTHER INFORMATION: primer

<400> SEQUENCE: 5
gacaaagcgg ccgcctgcat ccacaacatt ac                                 32

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
acatatgggc cctgtaatta aaaagcgtgc                                    30

<210> SEQ ID NO 7
<211> LENGTH: 29
<212> TYPE: DNA
<213> ORGANISM: Artificial Sequence
<220> FEATURE:
<223> OTHER INFORMATION: primer

<400> SEQUENCE: 7
gggtggaagc ttatgggaga tacacctac                                     29

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
tggggcaagc ttttaaatta aaaagcgtgc                                    30

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
ccctagtcta gaatgggggg ggctgccgcc                                    30

<210> SEQ ID NO 10
<211> LENGTH: 33
<212> TYPE: DNA
<213> ORGANISM: Artificial Sequence
<220> FEATURE:
<223> OTHER INFORMATION: primer -continued

```
<400> SEQUENCE: 10
ccctagtcta gactagtaaa acaagggctg gtg                                    33

<210> SEQ ID NO 11
<211> LENGTH: 28
<212> TYPE: DNA
<213> ORGANISM: Artificial Sequence
<220> FEATURE:
<223> OTHER INFORMATION: primer

<400> SEQUENCE: 11
aagaagggcg ccggtgcgag agcgtcag                                          28

<210> SEQ ID NO 12
<211> LENGTH: 32
<212> TYPE: DNA
<213> ORGANISM: Artificial Sequence
<220> FEATURE:
<223> OTHER INFORMATION: primer

<400> SEQUENCE: 12
aagggtggcg cccaaaactc ttgccttatg gc                                     32

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
aagcccaagc ttatgggggg ggctgccgcc                                        30

<210> SEQ ID NO 14
<211> LENGTH: 33
<212> TYPE: DNA
<213> ORGANISM: Artificial Sequence
<220> FEATURE:
<223> OTHER INFORMATION: primer

<400> SEQUENCE: 14
aagcccaagc ttctagtaaa acaagggctg gtg                                    33

<210> SEQ ID NO 15
<211> LENGTH: 48
<212> TYPE: DNA
<213> ORGANISM: Artificial Sequence
<220> FEATURE:
<223> OTHER INFORMATION: primer

<400> SEQUENCE: 15
gaccggaagg tctttgccgc gaaagcgagc ggggtcggcc gccttgag                    48

<210> SEQ ID NO 16
<211> LENGTH: 47
<212> TYPE: DNA
<213> ORGANISM: Artificial Sequence
<220> FEATURE:
<223> OTHER INFORMATION: primer

<400> SEQUENCE: 16
cgctttcgcg gcaaagacct tccggtcgcg gacgcggcgg ccgcccc                     47

<210> SEQ ID NO 17
```

-continued

```
<211> LENGTH: 34
<212> TYPE: DNA
<213> ORGANISM: Artificial Sequence
<220> FEATURE:
<223> OTHER INFORMATION: primer

<400> SEQUENCE: 17
caaatccaac aaaacgcgca cataggctcg atcc                                    34

<210> SEQ ID NO 18
<211> LENGTH: 34
<212> TYPE: DNA
<213> ORGANISM: Artificial Sequence
<220> FEATURE:
<223> OTHER INFORMATION: primer

<400> SEQUENCE: 18
gatcgacggt atgtgcgcgt tttggtgggat ttgc                                   34

<210> SEQ ID NO 19
<211> LENGTH: 9
<212> TYPE: PRT
<213> ORGANISM: HPV

<400> SEQUENCE: 19

Arg Ala His Tyr Asn Ile Val Thr Phe
1               5

<210> SEQ ID NO 20
<211> LENGTH: 9
<212> TYPE: PRT
<213> ORGANISM: HIV-1

<400> SEQUENCE: 20

Ala Met Gln Met Leu Lys Glu Thr Ile
1               5

<210> SEQ ID NO 21
<211> LENGTH: 13
<212> TYPE: PRT
<213> ORGANISM: HIV-1

<400> SEQUENCE: 21

Val Val Glu Asp Glu Gly Cys Thr Asn Leu Ser Gly Phe
1               5                   10

<210> SEQ ID NO 22
<211> LENGTH: 758
<212> TYPE: PRT
<213> ORGANISM: Artificial Sequence
<220> FEATURE:
<223> OTHER INFORMATION: gDgag

<400> SEQUENCE: 22

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
                20                  25                  30

Ser Leu Lys Met Ala Asp Pro Asn Arg Phe Arg Gly Lys Asp Leu Pro
        35                  40                  45

Val Leu Asp Gln Leu Thr Asp Pro Pro Gly Val Arg Arg Val Tyr His
    50                  55                  60

Ile Gln Ala Gly Leu Pro Asp Pro Phe Gln Pro Pro Ser Leu Pro Ile
65                  70                  75                  80
```

```
Thr Val Tyr Tyr Ala Val Leu Glu Arg Ala Cys Arg Ser Val Leu Leu
                85                  90                  95
Asn Ala Pro Ser Glu Ala Pro Gln Ile Val Arg Gly Ala Ser Glu Asp
            100                 105                 110
Val Arg Lys Gln Pro Tyr Asn Leu Thr Ile Ala Trp Phe Arg Met Gly
        115                 120                 125
Gly Asn Cys Ala Ile Pro Ile Thr Val Met Glu Tyr Thr Glu Cys Ser
    130                 135                 140
Tyr Asn Lys Ser Leu Gly Ala Cys Pro Ile Arg Thr Gln Pro Arg Trp
145                 150                 155                 160
Asn Tyr Tyr Asp Ser Phe Ser Ala Val Ser Glu Asp Asn Leu Gly Phe
                165                 170                 175
Leu Met His Ala Pro Ala Phe Glu Thr Ala Gly Thr Tyr Leu Arg Leu
            180                 185                 190
Val Lys Ile Asn Asp Trp Thr Glu Ile Thr Gln Phe Ile Leu Glu His
        195                 200                 205
Arg Ala Lys Gly Ser Cys Lys Tyr Ala Leu Pro Leu Arg Ile Pro Pro
    210                 215                 220
Ser Ala Cys Leu Ser Pro Gln Ala Tyr Gln Gln Gly Val Thr Val Asp
225                 230                 235                 240
Ser Ile Gly Met Leu Pro Arg Phe Ile Pro Glu Asn Gln Arg Thr Val
                245                 250                 255
Ala Val Tyr Ser Leu Lys Ile Ala Gly Trp His Gly Pro Lys Ala Pro
            260                 265                 270
Tyr Thr Ser Thr Leu Leu Pro Pro Glu Leu Ser Glu Thr Pro Asn Ala
        275                 280                 285
Thr Gln Pro Glu Leu Ala Pro Glu Asp Pro Glu Asp Ser Ala Leu Leu
    290                 295                 300
Glu Asp Pro Val Gly Thr Val Ala Pro Gly Ala Arg Ala Ser Val Leu
305                 310                 315                 320
Ser Gly Gly Glu Leu Asp Arg Trp Glu Lys Ile Arg Leu Arg Pro Gly
                325                 330                 335
Gly Lys Lys Lys Tyr Lys Leu Lys His Ile Val Trp Ala Ser Arg Glu
            340                 345                 350
Leu Glu Arg Phe Ala Val Asn Pro Gly Leu Leu Glu Thr Ser Glu Gly
        355                 360                 365
Cys Arg Gln Ile Leu Gly Gln Leu Gln Pro Ser Leu Gln Thr Gly Ser
    370                 375                 380
Glu Glu Leu Arg Ser Leu Tyr Asn Thr Val Ala Thr Leu Tyr Cys Val
385                 390                 395                 400
His Gln Arg Ile Glu Ile Lys Asp Thr Lys Glu Ala Leu Asp Lys Ile
                405                 410                 415
Glu Glu Glu Gln Asn Lys Ser Lys Lys Lys Ala Gln Gln Ala Ala Ala
            420                 425                 430
Asp Thr Gly His Ser Asn Gln Val Ser Gln Asn Tyr Pro Ile Val Gln
        435                 440                 445
Asn Ile Gln Gly Gln Met Val His Gln Ala Ile Ser Pro Arg Thr Leu
    450                 455                 460
Asn Ala Trp Val Lys Val Val Glu Glu Lys Ala Phe Ser Pro Glu Val
465                 470                 475                 480
Ile Pro Met Phe Ser Ala Leu Ser Glu Gly Ala Thr Pro Gln Asp Leu
                485                 490                 495
```

```
Asn Thr Met Leu Asn Thr Val Gly Gly His Gln Ala Ala Met Gln Met
            500                 505                 510

Leu Lys Glu Thr Ile Asn Glu Glu Ala Ala Asp Trp Asp Arg Val His
        515                 520                 525

Pro Val His Ala Gly Pro Ile Ala Pro Gly Gln Met Arg Glu Pro Arg
    530                 535                 540

Gly Ser Asp Ile Ala Gly Thr Thr Ser Thr Leu Gln Glu Gln Ile Gly
545                 550                 555                 560

Trp Met Thr Asn Asn Pro Pro Ile Pro Val Gly Glu Ile Tyr Lys Arg
                565                 570                 575

Trp Ile Ile Leu Gly Leu Asn Lys Ile Val Arg Met Tyr Ser Pro Thr
            580                 585                 590

Ser Ile Leu Asp Ile Arg Gln Gly Pro Lys Glu Pro Phe Arg Asp Tyr
        595                 600                 605

Val Asp Arg Phe Tyr Lys Thr Leu Arg Ala Glu Gln Ala Ser Gln Glu
    610                 615                 620

Val Lys Asn Trp Met Thr Glu Thr Leu Leu Val Gln Asn Ala Asn Pro
625                 630                 635                 640

Asp Cys Lys Thr Ile Leu Lys Ala Leu Gly Pro Ala Ala Thr Leu Glu
                645                 650                 655

Glu Met Met Thr Ala Cys Gln Gly Val Gly Gly Pro Gly His Lys Ala
            660                 665                 670

Arg Val Leu Ala Pro Gln Ile Pro Pro Asn Trp His Ile Pro Ser Ile
        675                 680                 685

Gln Asp Ala Ala Thr Pro Tyr His Pro Ala Thr Pro Asn Asn Met
    690                 695                 700

Gly Leu Ile Ala Gly Ala Val Gly Gly Ser Leu Leu Ala Ala Leu Val
705                 710                 715                 720

Ile Cys Gly Ile Val Tyr Trp Met Arg Arg Thr Gln Lys Ala Pro
                725                 730                 735

Lys Arg Ile Arg Leu Pro His Ile Arg Glu Asp Gln Pro Ser Ser
            740                 745                 750

His Gln Pro Leu Phe Tyr
        755

<210> SEQ ID NO 23
<211> LENGTH: 732
<212> TYPE: PRT
<213> ORGANISM: Artificial Sequence
<220> FEATURE:
<223> OTHER INFORMATION: gDE7E6E5

<400> SEQUENCE: 23

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Thr Asp Pro Pro Gly Val Arg Arg Val Tyr His
    50                  55                  60

Ile Gln Ala Gly Leu Pro Asp Pro Phe Gln Pro Pro Ser Leu Pro Ile
65                  70                  75                  80

Thr Val Tyr Tyr Ala Val Leu Glu Arg Ala Cys Arg Ser Val Leu Leu
                85                  90                  95
```

-continued

```
Asn Ala Pro Ser Glu Ala Pro Gln Ile Val Arg Gly Ala Ser Glu Asp
                100                 105                 110
Val Arg Lys Gln Pro Tyr Asn Leu Thr Ile Ala Trp Phe Arg Met Gly
            115                 120                 125
Gly Asn Cys Ala Ile Pro Ile Thr Val Met Glu Tyr Thr Glu Cys Ser
        130                 135                 140
Tyr Asn Lys Ser Leu Gly Ala Cys Pro Ile Arg Thr Gln Pro Arg Trp
145                 150                 155                 160
Asn Tyr Tyr Asp Ser Phe Ser Ala Val Ser Glu Asp Asn Leu Gly Phe
                165                 170                 175
Leu Met His Ala Pro Ala Phe Glu Thr Ala Gly Thr Tyr Leu Arg Leu
            180                 185                 190
Val Lys Ile Asn Asp Trp Thr Glu Ile Thr Gln Phe Ile Leu Glu His
        195                 200                 205
Arg Ala Lys Gly Ser Cys Lys Tyr Ala Leu Pro Leu Arg Ile Pro Pro
225                 230                 235                 240
Ser Ala Cys Leu Ser Pro Gln Ala Tyr Gln Gln Gly Val Thr Val Asp
225                 230                 235                 240
Ser Ile Gly Met Leu Pro Arg Phe Ile Pro Glu Asn Gln Arg Thr Val
                245                 250                 255
Ala Val Tyr Ser Leu Lys Ile Ala Gly Trp His Gly Pro His Gly Asp
            260                 265                 270
Thr Pro Thr Leu His Glu Tyr Met Leu Asp Leu Gln Pro Glu Thr Thr
        275                 280                 285
Asp Leu Tyr Cys Tyr Glu Gln Leu Asn Asp Ser Ser Glu Glu Glu Asp
290                 295                 300
Glu Ile Asp Gly Pro Ala Gly Gln Ala Glu Pro Asp Arg Ala His Tyr
305                 310                 315                 320
Asn Ile Val Thr Phe Cys Cys Lys Cys Asp Ser Thr Leu Arg Leu Cys
                325                 330                 335
Val Gln Ser Thr His Val Asp Ile Arg Thr Leu Glu Asp Leu Leu Met
            340                 345                 350
Gly Thr Leu Gly Ile Val Cys Pro Ile Cys Ser Gln Lys Pro Gly Ala
        355                 360                 365
His Gln Lys Arg Thr Ala Met Phe Gln Asp Pro Gln Glu Arg Pro Arg
        370                 375                 380
Lys Leu Pro Gln Leu Cys Thr Glu Leu Gln Thr Thr Ile His Asp Ile
385                 390                 395                 400
Ile Leu Glu Cys Val Tyr Cys Lys Gln Gln Leu Leu Arg Arg Glu Val
                405                 410                 415
Tyr Asp Phe Ala Phe Arg Asp Leu Cys Ile Val Tyr Arg Asp Gly Asn
            420                 425                 430
Pro Tyr Ala Val Cys Asp Lys Cys Leu Lys Phe Tyr Ser Lys Ile Ser
        435                 440                 445
Glu Tyr Arg His Tyr Cys Tyr Ser Leu Tyr Gly Thr Thr Leu Glu Gln
    450                 455                 460
Gln Tyr Asn Lys Pro Leu Cys Asp Leu Leu Ile Arg Cys Ile Asn Cys
465                 470                 475                 480
Gln Lys Pro Leu Cys Pro Glu Glu Lys Gln Arg His Leu Asp Lys Lys
                485                 490                 495
Gln Arg Phe His Asn Ile Arg Gly Arg Trp Thr Gly Arg Cys Met Ser
            500                 505                 510
Cys Cys Arg Ser Ser Arg Thr Arg Arg Glu Thr Gln Leu Ala Ala Ala
```

```
            515                 520                 525
Cys Ile His Asn Ile Thr Gly Val Leu Phe Ala Leu Leu Cys Val Leu
        530                 535                 540

Leu Cys Val Cys Leu Leu Ile Arg Pro Leu Leu Ser Val Ser Thr
545                 550                 555                 560

Tyr Thr Ser Leu Ile Ile Leu Val Leu Leu Leu Trp Ile Thr Ala Ala
                565                 570                 575

Ser Ala Phe Arg Cys Phe Ile Val Tyr Ile Ile Phe Val Tyr Ile Pro
            580                 585                 590

Leu Phe Leu Ile His Thr His Ala Arg Phe Leu Ile Thr Gly Pro Lys
        595                 600                 605

Ala Pro Tyr Thr Ser Thr Leu Leu Pro Pro Glu Leu Ser Glu Thr Pro
    610                 615                 620

Asn Ala Thr Gln Pro Glu Leu Ala Pro Glu Asp Pro Glu Asp Ser Ala
625                 630                 635                 640

Leu Leu Glu Asp Pro Val Gly Thr Val Ala Pro Gln Ile Pro Pro Asn
                645                 650                 655

Trp His Ile Pro Ser Ile Gln Asp Ala Ala Thr Pro Tyr His Pro Pro
            660                 665                 670

Ala Thr Pro Asn Asn Met Gly Leu Ile Ala Gly Ala Val Gly Gly Ser
        675                 680                 685

Leu Leu Ala Ala Leu Val Ile Cys Gly Ile Val Tyr Trp Met Arg Arg
    690                 695                 700

Arg Thr Gln Lys Ala Pro Lys Arg Ile Arg Leu Pro His Ile Arg Glu
705                 710                 715                 720

Asp Asp Gln Pro Ser Ser His Gln Pro Leu Phe Tyr
                725                 730

<210> SEQ ID NO 24
<211> LENGTH: 732
<212> TYPE: PRT
<213> ORGANISM: Artificial Sequence
<220> FEATURE:
<223> OTHER INFORMATION: gDE7E6E5 W294A

<400> SEQUENCE: 24

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
                20                  25                  30

Ser Leu Lys Met Ala Asp Pro Asn Arg Phe Arg Gly Lys Asp Leu Pro
            35                  40                  45

Val Leu Asp Gln Leu Thr Asp Pro Pro Gly Val Arg Arg Val Tyr His
        50                  55                  60

Ile Gln Ala Gly Leu Pro Asp Pro Phe Gln Pro Pro Ser Leu Pro Ile
65                  70                  75                  80

Thr Val Tyr Tyr Ala Val Leu Glu Arg Ala Cys Arg Ser Val Leu Leu
                85                  90                  95

Asn Ala Pro Ser Glu Ala Pro Gln Ile Val Arg Gly Ala Ser Glu Asp
            100                 105                 110

Val Arg Lys Gln Pro Tyr Asn Leu Thr Ile Ala Trp Phe Arg Met Gly
        115                 120                 125

Gly Asn Cys Ala Ile Pro Ile Thr Val Met Glu Tyr Thr Glu Cys Ser
    130                 135                 140

Tyr Asn Lys Ser Leu Gly Ala Cys Pro Ile Arg Thr Gln Pro Arg Trp
```

-continued

```
            145                 150                 155                 160
        Asn Tyr Tyr Asp Ser Phe Ser Ala Val Ser Glu Asp Asn Leu Gly Phe
                        165                 170                 175
        Leu Met His Ala Pro Ala Phe Glu Thr Ala Gly Thr Tyr Leu Arg Leu
                        180                 185                 190
        Val Lys Ile Asn Asp Trp Thr Glu Ile Thr Gln Phe Ile Leu Glu His
                        195                 200                 205
        Arg Ala Lys Gly Ser Cys Lys Tyr Ala Leu Pro Leu Arg Ile Pro Pro
                        210                 215                 220
        Ser Ala Cys Leu Ser Pro Gln Ala Tyr Gln Gln Gly Val Thr Val Asp
        225                 230                 235                 240
        Ser Ile Gly Met Leu Pro Arg Phe Ile Pro Glu Asn Gln Arg Thr Val
                            245                 250                 255
        Ala Val Tyr Ser Leu Lys Ile Ala Gly Trp His Gly Pro His Gly Asp
                        260                 265                 270
        Thr Pro Thr Leu His Glu Tyr Met Leu Asp Leu Gln Pro Glu Thr Thr
                    275                 280                 285
        Asp Leu Tyr Cys Tyr Glu Gln Leu Asn Asp Ser Ser Glu Glu Glu Asp
                    290                 295                 300
        Glu Ile Asp Gly Pro Ala Gly Gln Ala Glu Pro Asp Arg Ala His Tyr
        305                 310                 315                 320
        Asn Ile Val Thr Phe Cys Cys Lys Cys Asp Ser Thr Leu Arg Leu Cys
                        325                 330                 335
        Val Gln Ser Thr His Val Asp Ile Arg Thr Leu Glu Asp Leu Leu Met
                    340                 345                 350
        Gly Thr Leu Gly Ile Val Cys Pro Ile Cys Ser Gln Lys Pro Gly Ala
                355                 360                 365
        His Gln Lys Arg Thr Ala Met Phe Gln Asp Pro Gln Glu Arg Pro Arg
            370                 375                 380
        Lys Leu Pro Gln Leu Cys Thr Glu Leu Gln Thr Thr Ile His Asp Ile
        385                 390                 395                 400
        Ile Leu Glu Cys Val Tyr Cys Lys Gln Gln Leu Leu Arg Arg Glu Val
                        405                 410                 415
        Tyr Asp Phe Ala Phe Arg Asp Leu Cys Ile Val Tyr Arg Asp Gly Asn
                        420                 425                 430
        Pro Tyr Ala Val Cys Asp Lys Cys Leu Lys Phe Tyr Ser Lys Ile Ser
                        435                 440                 445
        Glu Tyr Arg His Tyr Cys Tyr Ser Leu Tyr Gly Thr Thr Leu Glu Gln
                    450                 455                 460
        Gln Tyr Asn Lys Pro Leu Cys Asp Leu Leu Ile Arg Cys Ile Asn Cys
        465                 470                 475                 480
        Gln Lys Pro Leu Cys Pro Glu Glu Lys Gln Arg His Leu Asp Lys Lys
                        485                 490                 495
        Gln Arg Phe His Asn Ile Arg Gly Arg Trp Thr Gly Arg Cys Met Ser
                    500                 505                 510
        Cys Cys Arg Ser Ser Arg Thr Arg Arg Glu Thr Gln Leu Ala Ala Ala
                515                 520                 525
        Cys Ile His Asn Ile Thr Gly Val Leu Phe Ala Leu Leu Cys Val Leu
                    530                 535                 540
        Leu Cys Val Cys Leu Leu Ile Arg Pro Leu Leu Ser Val Ser Thr
        545                 550                 555                 560
        Tyr Thr Ser Leu Ile Ile Leu Val Leu Leu Leu Trp Ile Thr Ala Ala
                        565                 570                 575
```

```
Ser Ala Phe Arg Cys Phe Ile Val Tyr Ile Ile Phe Val Tyr Ile Pro
                580                 585                 590

Leu Phe Leu Ile His Thr His Ala Arg Phe Leu Ile Thr Gly Pro Lys
            595                 600                 605

Ala Pro Tyr Thr Ser Thr Leu Leu Pro Pro Glu Leu Ser Glu Thr Pro
        610                 615                 620

Asn Ala Thr Gln Pro Glu Leu Ala Pro Glu Asp Pro Glu Asp Ser Ala
625                 630                 635                 640

Leu Leu Glu Asp Pro Val Gly Thr Val Ala Pro Gln Ile Pro Pro Asn
                645                 650                 655

Ala His Ile Pro Ser Ile Gln Asp Ala Ala Thr Pro Tyr His Pro Pro
            660                 665                 670

Ala Thr Pro Asn Asn Met Gly Leu Ile Ala Gly Ala Val Gly Gly Ser
        675                 680                 685

Leu Leu Ala Ala Leu Val Ile Cys Gly Ile Val Tyr Trp Met Arg Arg
    690                 695                 700

Arg Thr Gln Lys Ala Pro Lys Arg Ile Arg Leu Pro His Ile Arg Glu
705                 710                 715                 720

Asp Asp Gln Pro Ser Ser His Gln Pro Leu Phe Tyr
                725                 730

<210> SEQ ID NO 25
<211> LENGTH: 394
<212> TYPE: PRT
<213> ORGANISM: Artificial Sequence
<220> FEATURE:
<223> OTHER INFORMATION: gD W294A

<400> SEQUENCE: 25

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Thr Asp Pro Pro Gly Val Arg Arg Val Tyr His
    50                  55                  60

Ile Gln Ala Gly Leu Pro Asp Pro Phe Gln Pro Pro Ser Leu Pro Ile
65                  70                  75                  80

Thr Val Tyr Tyr Ala Val Leu Glu Arg Ala Cys Arg Ser Val Leu Leu
                85                  90                  95

Asn Ala Pro Ser Glu Ala Pro Gln Ile Val Arg Gly Ala Ser Glu Asp
            100                 105                 110

Val Arg Lys Gln Pro Tyr Asn Leu Thr Ile Ala Trp Phe Arg Met Gly
        115                 120                 125

Gly Asn Cys Ala Ile Pro Ile Thr Val Met Glu Tyr Thr Glu Cys Ser
    130                 135                 140

Tyr Asn Lys Ser Leu Gly Ala Cys Pro Ile Arg Thr Gln Pro Arg Trp
145                 150                 155                 160

Asn Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205
```

```
Arg Ala Lys Gly Ser Cys Lys Tyr Ala Leu Pro Leu Arg Ile Pro Pro
        210                 215                 220

Ser Ala Cys Leu Ser Pro Gln Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Val Tyr Ser Leu Lys Ile Ala Gly Trp His Gly Pro Lys Ala Pro
            260                 265                 270

Tyr Thr Ser Thr Leu Leu Pro Pro Glu Leu Ser Glu Thr Pro Asn Ala
        275                 280                 285

Thr Gln Pro Glu Leu Ala Pro Glu Asp Pro Glu Asp Ser Ala Leu Leu
    290                 295                 300

Glu Asp Pro Val Gly Thr Val Ala Pro Gln Ile Pro Pro Asn Ala His
305                 310                 315                 320

Ile Pro Ser Ile Gln Asp Ala Ala Thr Pro Tyr His Pro Pro Ala Thr
                325                 330                 335

Pro Asn Asn Met Gly Leu Ile Ala Gly Ala Val Gly Gly Ser Leu Leu
            340                 345                 350

Ala Ala Leu Val Ile Cys Gly Ile Val Tyr Trp Met Arg Arg Arg Thr
        355                 360                 365

Gln Lys Ala Pro Lys Arg Ile Arg Leu Pro His Ile Arg Glu Asp Asp
    370                 375                 380

Gln Pro Ser Ser His Gln Pro Leu Phe Tyr
385                 390
```

```
<210> SEQ ID NO 26
<211> LENGTH: 1206
<212> TYPE: DNA
<213> ORGANISM: Herpes simplex 1
<220> FEATURE:
<221> NAME/KEY: CDS
<222> LOCATION: (1)...(1185)

<400> SEQUENCE: 26
```

```
atg ggg ggg gct gcc gcc agg ttg ggg gcc gtg att ttg ttt gtc gtc       48
Met Gly Gly Ala Ala Ala Arg Leu Gly Ala Val Ile Leu Phe Val Val
1               5                   10                  15 ata gtg ggc ctc cat ggg gtc cgc ggc aaa tat gcc ttg gcg gat gcc       96
Ile Val Gly Leu His Gly Val Arg Gly Lys Tyr Ala Leu Ala Asp Ala
            20                  25                  30 tct ctc aag atg gcc gac ccc aat cgc ttt cgc ggc aaa gac ctt ccg      144
Ser Leu Lys Met Ala Asp Pro Asn Arg Phe Arg Gly Lys Asp Leu Pro
        35                  40                  45 gtc ctg gac cag ctg acc gac cct ccg ggg gtc cgg cgc gtg tac cac      192
Val Leu Asp Gln Leu Thr Asp Pro Pro Gly Val Arg Arg Val Tyr His
    50                  55                  60 atc cag gcg ggc cta ccg gac ccg ttc cag ccc ccc agc ctc ccg atc      240
Ile Gln Ala Gly Leu Pro Asp Pro Phe Gln Pro Pro Ser Leu Pro Ile
65                  70                  75                  80 acg gtt tac tac gcc gtg ttg gag cgc gcc tgc cgc agc gtg ctc cta      288
Thr Val Tyr Tyr Ala Val Leu Glu Arg Ala Cys Arg Ser Val Leu Leu
                85                  90                  95 aac gca ccg tcg gag gcc ccc cag att gtc cgc ggg gcc tcc gaa gac      336
Asn Ala Pro Ser Glu Ala Pro Gln Ile Val Arg Gly Ala Ser Glu Asp
            100                 105                 110 gtc cgg aaa caa ccc tac aac ctg acc atc gct tgg ttt cgg atg gga      384
Val Arg Lys Gln Pro Tyr Asn Leu Thr Ile Ala Trp Phe Arg Met Gly
        115                 120                 125
```

```
ggc aac tgt gct atc ccc atc acg gtc atg gag tac acc gaa tgc tcc        432
Gly Asn Cys Ala Ile Pro Ile Thr Val Met Glu Tyr Thr Glu Cys Ser
130                 135                 140 tac aac aag tct ctg ggg gcc tgt ccc atc cga acg cag ccc cgc tgg        480
Tyr Asn Lys Ser Leu Gly Ala Cys Pro Ile Arg Thr Gln Pro Arg Trp
145                 150                 155                 160 aac tac tat gac agc ttc agc gcc gtc agc gag gat aac ctg ggg ttc        528
Asn Tyr Tyr Asp Ser Phe Ser Ala Val Ser Glu Asp Asn Leu Gly Phe
                165                 170                 175 ctg atg cac gcc ccc gcg ttt gag acc gcc ggc acg tac ctg cgg ctc        576
Leu Met His Ala Pro Ala Phe Glu Thr Ala Gly Thr Tyr Leu Arg Leu
            180                 185                 190 gtg aag ata aac gac tgg acg gag att aca cag ttt atc ctg gag cac        624
Val Lys Ile Asn Asp Trp Thr Glu Ile Thr Gln Phe Ile Leu Glu His
        195                 200                 205 cga gcc aag ggc tcc tgt aag tac gcc ctc ccg ctc cgc atc ccc ccg        672
Arg Ala Lys Gly Ser Cys Lys Tyr Ala Leu Pro Leu Arg Ile Pro Pro
    210                 215                 220 tca gcc tgc ctg tcc ccc cag gcc tac cag cag ggg gtg acg gtg gac        720
Ser Ala Cys Leu Ser Pro Gln Ala Tyr Gln Gln Gly Val Thr Val Asp
225                 230                 235                 240 agc atc ggg atg ctg ccc cgc ttc atc ccc gag aac cag cgc acc gtc        768
Ser Ile Gly Met Leu Pro Arg Phe Ile Pro Glu Asn Gln Arg Thr Val
                245                 250                 255 gcc gta tac agc ttg aag atc gcc ggg tgg cac ggg ccc aag gcc cca        816
Ala Val Tyr Ser Leu Lys Ile Ala Gly Trp His Gly Pro Lys Ala Pro
            260                 265                 270 tac acg agc acc ctg ctg ccc ccg gag ctg tcc gag acc ccc aac gcc        864
Tyr Thr Ser Thr Leu Leu Pro Pro Glu Leu Ser Glu Thr Pro Asn Ala
        275                 280                 285 acg cag cca gaa ctc gcc ccg gaa gac ccc gag gat tcg gcc ctc ttg        912
Thr Gln Pro Glu Leu Ala Pro Glu Asp Pro Glu Asp Ser Ala Leu Leu
    290                 295                 300 gag gac ccc gtg ggg acg gtg gcg ccg caa atc cca cca aac tgg cac        960
Glu Asp Pro Val Gly Thr Val Ala Pro Gln Ile Pro Pro Asn Trp His
305                 310                 315                 320 ata ccg tcg atc cag gac gcc gcg acg cct tac cat ccc ccg gcc acc       1008
Ile Pro Ser Ile Gln Asp Ala Ala Thr Pro Tyr His Pro Pro Ala Thr
                325                 330                 335 ccg aac aac atg ggc ctg atc gcc ggc gcg gtg ggc ggc agt ctc ctg       1056
Pro Asn Asn Met Gly Leu Ile Ala Gly Ala Val Gly Gly Ser Leu Leu
            340                 345                 350 gca gcc ctg gtc att tgc gga att gtg tac tgg atg cgc cgc cgc act       1104
Ala Ala Leu Val Ile Cys Gly Ile Val Tyr Trp Met Arg Arg Arg Thr
        355                 360                 365 caa aaa gcc cca aag cgc ata cgc ctc ccc cac atc cgg gaa gac gac       1152
Gln Lys Ala Pro Lys Arg Ile Arg Leu Pro His Ile Arg Glu Asp Asp
    370                 375                 380 cag ccg tcc tcg cac cag ccc ttg ttt tac tag atacccccc ttaatgggtg      1205
Gln Pro Ser Ser His Gln Pro Leu Phe Tyr *
385                 390 c                                                                      1206

<210> SEQ ID NO 27
<211> LENGTH: 394
<212> TYPE: PRT
<213> ORGANISM: Herpes simplex 1

<400> SEQUENCE: 27
```

```
Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
            35                  40                  45

Val Leu Asp Gln Leu Thr Asp Pro Pro Gly Val Arg Arg Val Tyr His
50                  55                  60

Ile Gln Ala Gly Leu Pro Asp Pro Phe Gln Pro Ser Leu Pro Ile
65                  70                  75                  80

Thr Val Tyr Tyr Ala Val Leu Glu Arg Ala Cys Arg Ser Val Leu Leu
                85                  90                  95

Asn Ala Pro Ser Glu Ala Pro Gln Ile Val Arg Gly Ala Ser Glu Asp
            100                 105                 110

Val Arg Lys Gln Pro Tyr Asn Leu Thr Ile Ala Trp Phe Arg Met Gly
            115                 120                 125

Gly Asn Cys Ala Ile Pro Ile Thr Val Met Glu Tyr Thr Glu Cys Ser
            130                 135                 140

Tyr Asn Lys Ser Leu Gly Ala Cys Pro Ile Arg Thr Gln Pro Arg Trp
145                 150                 155                 160

Asn Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
            195                 200                 205

Arg Ala Lys Gly Ser Cys Lys Tyr Ala Leu Pro Leu Arg Ile Pro Pro
210                 215                 220

Ser Ala Cys Leu Ser Pro Gln Ala Tyr Gln Gln Gly Val Thr Val Asp
225                 230                 235                 240

Ser Ile Gly Met Leu Pro Arg Phe Ile Pro Glu Asn Gln Arg Thr Val
            245                 250                 255

Ala Val Tyr Ser Leu Lys Ile Ala Gly Trp His Gly Pro Lys Ala Pro
            260                 265                 270

Tyr Thr Ser Thr Leu Leu Pro Pro Glu Leu Ser Glu Thr Pro Asn Ala
            275                 280                 285

Thr Gln Pro Glu Leu Ala Pro Glu Asp Pro Glu Asp Ser Ala Leu Leu
            290                 295                 300

Glu Asp Pro Val Gly Thr Val Ala Pro Gln Ile Pro Pro Asn Trp His
305                 310                 315                 320

Ile Pro Ser Ile Gln Asp Ala Ala Thr Pro Tyr His Pro Pro Ala Thr
            325                 330                 335

Pro Asn Asn Met Gly Leu Ile Ala Gly Ala Val Gly Gly Ser Leu Leu
            340                 345                 350

Ala Ala Leu Val Ile Cys Gly Ile Val Tyr Trp Met Arg Arg Arg Thr
            355                 360                 365

Gln Lys Ala Pro Lys Arg Ile Arg Leu Pro His Ile Arg Glu Asp Asp
            370                 375                 380

Gln Pro Ser Ser His Gln Pro Leu Phe Tyr
385                 390

<210> SEQ ID NO 28
<211> LENGTH: 1730
<212> TYPE: DNA
```

```
<213> ORGANISM: Herpes simplex 2
<220> FEATURE:
<221> NAME/KEY: CDS
<222> LOCATION: (275)...(1456)

<400> SEQUENCE: 28
agagcggtgg gggggggggg gggaagaaac taaaaacaca tcaagcccac aaccctccac      60
aaggggggtt atggcggacc caccgcacca ccatactccg attcgaccac atatgcaacc     120
aaatcacccc cagaggggaa ggttccattt ttacgaggag gaggagtata atagagtctt     180
tgtgtttaaa acccggggtc ggtgtggtgt tcggtcataa gctgcattgc gaacgactag     240
tcggccgttt ttcgtgtgca tcgcgtatca cggc atg ggg cgt ttg acc tcc ggc    295
                                    Met Gly Arg Leu Thr Ser Gly
                                      1               5 gtc ggg acg gcg gcc ctg cta gtt gtc gcg gtg gga ctc cgc gtc gtc       343
Val Gly Thr Ala Ala Leu Leu Val Val Ala Val Gly Leu Arg Val Val
         10                  15                  20 tgc gcc aaa tac gcc tta gca gac ccc tcg ctt aag atg gcc gat ccc       391
Cys Ala Lys Tyr Ala Leu Ala Asp Pro Ser Leu Lys Met Ala Asp Pro
 25                  30                  35 aat cga ttt cgc ggg aag aac ctt ccg gtt ttg gac cag ctg acc gac       439
Asn Arg Phe Arg Gly Lys Asn Leu Pro Val Leu Asp Gln Leu Thr Asp
 40                  45                  50                  55 ccc ccc ggg gtg aag cgt gtt tac cac att cag ccg agc ctg gag gac       487
Pro Pro Gly Val Lys Arg Val Tyr His Ile Gln Pro Ser Leu Glu Asp
                 60                  65                  70 ccg ttc cag ccc ccc agc atc ccg atc act gtg tac tac gca gtg ctg       535
Pro Phe Gln Pro Pro Ser Ile Pro Ile Thr Val Tyr Tyr Ala Val Leu
             75                  80                  85 gaa cgt gcc tgc cgc agc gtg ctc cta cat gcc cca tcg gag gcc ccc       583
Glu Arg Ala Cys Arg Ser Val Leu Leu His Ala Pro Ser Glu Ala Pro
         90                  95                 100 cag atc gtg cgc ggg gct tcg gac gag gcc cga aag cac acg tac aac       631
Gln Ile Val Arg Gly Ala Ser Asp Glu Ala Arg Lys His Thr Tyr Asn
105                 110                 115 ctg acc atc gcc tgg tat cgc atg gga gac aat tgc gct atc ccc atc       679
Leu Thr Ile Ala Trp Tyr Arg Met Gly Asp Asn Cys Ala Ile Pro Ile
120                 125                 130                 135 acg gtt atg gaa tac acc gag tgc ccc tac aac aag tcg ttg ggg gtc       727
Thr Val Met Glu Tyr Thr Glu Cys Pro Tyr Asn Lys Ser Leu Gly Val
                140                 145                 150 tgc ccc atc cga acg cag ccc cgc tgg agc tac tat gac agc ttt agc       775
Cys Pro Ile Arg Thr Gln Pro Arg Trp Ser Tyr Tyr Asp Ser Phe Ser
            155                 160                 165 gcc gtc agc gag gat aac ctg gga ttc ctg atg cac gcc ccc gcc ttc       823
Ala Val Ser Glu Asp Asn Leu Gly Phe Leu Met His Ala Pro Ala Phe
        170                 175                 180 gag acc gcg ggt acg tac ctg cgg cta gtg aag ata aac gac tgg acg       871
Glu Thr Ala Gly Thr Tyr Leu Arg Leu Val Lys Ile Asn Asp Trp Thr
    185                 190                 195 gag atc aca caa ttt atc ctg gag cac cgg gcc cgc gcc tcc tgc aag       919
Glu Ile Thr Gln Phe Ile Leu Glu His Arg Ala Arg Ala Ser Cys Lys
200                 205                 210                 215 tac gct ctc ccc ctg cgc atc ccc ccg gca gcg tgc ctc acc tcg aag       967
Tyr Ala Leu Pro Leu Arg Ile Pro Pro Ala Ala Cys Leu Thr Ser Lys
                220                 225                 230 gcc tac caa cag ggc gtg acg gtc gac agc atc ggg atg tta ccc cgc      1015
Ala Tyr Gln Gln Gly Val Thr Val Asp Ser Ile Gly Met Leu Pro Arg
            235                 240                 245
```

-continued

```
ttt act ccc gaa aac cag cgc acc gtc gcc cta tac agc tta aaa atc      1063
Phe Thr Pro Glu Asn Gln Arg Thr Val Ala Leu Tyr Ser Leu Lys Ile
        250                 255                 260 gcc ggg tgg cac ggc ccc aag ccc ccg tac acc agc acc ctg ctg ccg      1111
Ala Gly Trp His Gly Pro Lys Pro Pro Tyr Thr Ser Thr Leu Leu Pro
265                 270                 275 ccg gag ctg tcc gac acc acc aac gcc acg caa ccc gaa ctc gtt ccg      1159
Pro Glu Leu Ser Asp Thr Thr Asn Ala Thr Gln Pro Glu Leu Val Pro
280                 285                 290                 295 gaa gac ccc gag gac tcg gcc ctc tta gag gat ccc gcc ggg acg gtg      1207
Glu Asp Pro Glu Asp Ser Ala Leu Leu Glu Asp Pro Ala Gly Thr Val
                300                 305                 310 tct tcg cag atc ccc cca aac tgg cac atc ccg tcg atc cag gac gtc      1255
Ser Ser Gln Ile Pro Pro Asn Trp His Ile Pro Ser Ile Gln Asp Val
            315                 320                 325 gcg ccg cac cac gcc ccc gcc gcc cca gcc aac ccg ggc ctg atc atc      1303
Ala Pro His His Ala Pro Ala Ala Pro Ala Asn Pro Gly Leu Ile Ile
        330                 335                 340 ggc gcg ctg gcc ggc agt acc ctg gcg gcg ctg gtc atc ggc ggt att      1351
Gly Ala Leu Ala Gly Ser Thr Leu Ala Ala Leu Val Ile Gly Gly Ile
345                 350                 355 gcg ttt tgg gta cgc cgc cgg cgc tca gtg gcc ccc aag cgc cta cgt      1399
Ala Phe Trp Val Arg Arg Arg Arg Ser Val Ala Pro Lys Arg Leu Arg
360                 365                 370                 375 ctc ccc cac atc cgg gat gac gac gcg ccc ccc tcg cac cag cca ttg      1447
Leu Pro His Ile Arg Asp Asp Asp Ala Pro Pro Ser His Gln Pro Leu
                380                 385                 390 ttt tac tag aggagtttcc ccgctcccgt gtacctctga ggcccgtgtg              1496
Phe Tyr  * gagggtggct gggtatttta gggtgggact tggactccgc ataaaggagt ctcgaaggag    1556
ggaaactagg acagttcata ggccgggagc gtggggcgcg cgccgcgtgt cccgacgatt    1616
agccagccgc gcccacagcc acctcgaccc ggtccgatcc gcggtatgcc cggccgctcg    1676
ctgcagggcc tggcgatcct gggcctgtgg gtctgcgcca ccggcctggt ccgt          1730

<210> SEQ ID NO 29
<211> LENGTH: 393
<212> TYPE: PRT
<213> ORGANISM: Herpes simplex 2

<400> SEQUENCE: 29

Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Asp Gln Leu Thr Asp Pro Pro Gly Val Lys Arg Val Tyr His
    50                  55                  60

Ile Gln Pro Ser Leu Glu Asp Pro Phe Gln Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
        115                 120                 125
```

-continued

```
Asp Asn Cys Ala Ile Pro Ile Thr Val Met Glu Tyr Thr Glu Cys Pro
130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Arg Ala Ser Cys Lys Tyr Ala Leu Pro Leu Arg Ile Pro Pro
210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Thr Pro Glu Asn Gln Arg Thr Val
                245                 250                 255

Ala Leu Tyr Ser Leu Lys Ile Ala Gly Trp His Gly Pro Lys Pro Pro
            260                 265                 270

Tyr Thr Ser Thr Leu Leu Pro Pro Glu Leu Ser Asp Thr Thr Asn Ala
        275                 280                 285

Thr Gln Pro Glu Leu Val Pro Glu Asp Pro Glu Asp Ser Ala Leu Leu
290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro
                325                 330                 335

Ala Asn Pro Gly Leu Ile Ile Gly Ala Leu Ala Gly Ser Thr Leu Ala
            340                 345                 350

Ala Leu Val Ile Gly Gly Ile Ala Phe Trp Val Arg Arg Arg Arg Ser
        355                 360                 365

Val Ala Pro Lys Arg Leu Arg Leu Pro His Ile Arg Asp Asp Asp Ala
370                 375                 380

Pro Pro Ser His Gln Pro Leu Phe Tyr
385                 390
```

<210> SEQ ID NO 30
<211> LENGTH: 8
<212> TYPE: PRT
<213> ORGANISM: HIV-1

<400> SEQUENCE: 30

```
Ser Ile Ile Asn Phe Glu Lys Leu
1               5
```

<210> SEQ ID NO 31
<211> LENGTH: 2199
<212> TYPE: DNA
<213> ORGANISM: Artificial Sequence
<220> FEATURE:
<223> OTHER INFORMATION: nucleotide sequence encoding gDE7E6E5

<400> SEQUENCE: 31

```
atggggggggg ctgccgccag gttgggggcc gtgattttgt tgtcgtcat agtgggcctc    60 catgggtcc gcggcaaata tgccttggcg gatgcctctc tcaagatggc cgaccccaat   120
cgctttcgcg gcaaagacct tccggtcctg gaccagctga ccgaccctcc ggggtccgg   180 cgcgtgtacc acatccaggc gggcctaccg gacccgttcc agcccccag cctcccgatc   240
```

```
acggtttact acgccgtgtt ggagcgcgcc tgccgcagcg tgctcctaaa cgcaccgtcg      300 gaggccccc  agattgtccg cggggcctcc gaagacgtcc ggaaacaacc ctacaacctg      360
accatcgctt ggtttcggat gggaggcaac tgtgctatcc ccatcacggt catggagtac      420
accgaatgct cctacaacaa gtctctgggg gcctgtccca tccgaacgca gccccgctgg      480
aactactatg acagcttcag cgccgtcagc gaggataacc tggggttcct gatgcacgcc      540
cccgcgtttg agaccgccgg cacgtacctg cggctcgtga agataaacga ctggacggag      600
attacacagt ttatcctgga gcaccgagcc aagggctcct gtaagtacgc cctcccgctg      660
cgcatccccc cgtcagcctg cctgtcccc  caggcctacc agcaggggt  gacggtggac      720 agcatcggga tgctgccccg cttcatcccc gagaaccagc gcaccgtcgc cgtatacagc      780
ttgaagatcg ccgggtggca cgggccccat ggagatacac ctacattgca tgaatatatg      840
ttagatttgc aaccagagac aactgatctc tactgttatg agcaattaaa tgacagctca      900
gaggaggagg atgaaataga tggtccagct ggacaagcag aaccggacag agcccattac      960
aatattgtaa ccttttgttg caagtgtgac tctacgcttc ggttgtgcgt acaaagcaca     1020
cacgtagaca ttcgtacttt ggaagacctg ttaatgggca cactaggaat tgtgtgcccc     1080
atctgttctc agaaaccagg cgcccaccaa agagaactg  caatgtttca ggacccacag     1140
gagcgaccca gaaagttacc acagttatgc acagagctgc aaacaactat acatgatata     1200
atattagaat gtgtgtactg caagcaacag ttactgcgac gtgaggtata tgactttgct     1260
tttcgggatt tatgcatagt atatagagat gggaatccat atgctgtatg tgataaatgt     1320
ttaaagtttt attctaaaat tagtgagtat agacattatt gttatagttt gtatggaaca     1380
acattagaac agcaatacaa caaccgttg  tgtgatttgt taattaggtg tattaactgt     1440
caaaagccac tgtgtcctga agaaaagcaa agacatctgg acaaaaagca agattccat      1500 aatataaggg gtcggtggac cggtcgatgt atgtcttgtt gcagatcatc aagaacacgt     1560
agagaaaccc agctggcggc cgcctgcatc cacaacatta ctggcgtgct ttttgctttg     1620
ctttgtgtgc ttttgtgtgt ctgcctatta atacgtccgc tgcttttgtc tgtgtctaca     1680
tacacatcat taataatatt ggtattacta ttgtggataa cagcagcctc tgcgtttagg     1740
tgttttattg tatatattat atttgtttat ataccattat ttttaataca tacacatgca     1800 cgcttttttaa ttacagggcc caaggcccca tacacgagca ccctgctgcc cccggagctg     1860
tccgagaccc ccaacgccac gcagccagaa ctcgccccgg aagaccccga ggattcggcc     1920
ctcttggagg accccgtggg gacggtggcg ccgcaaatcc caccaaactg gcacataccg     1980
tcgatccagg acgccgcgac gccttaccat ccccggcca  ccccgaacaa catgggcctg     2040
atcgccggcg cggtgggcgg cagtctcctg gcagccctgg tcatttgcgg aattgtgtac     2100
tggatgcgcc gccgcactca aaagccccca agcgcatac  gcctccccca catccgggaa     2160
gacgaccagc cgtcctcgca ccagcccttg ttttactag                            2199
```

<210> SEQ ID NO 32
<211> LENGTH: 2277
<212> TYPE: DNA
<213> ORGANISM: Artificial Sequence
<220> FEATURE:
<223> OTHER INFORMATION: nucleotide sequence encoding gDgag

<400> SEQUENCE: 32

```
atggggggg  ctgccgccag gttgggggcc gtgattttgt ttgtcgtcat agtgggcctc       60
```

| | |
|---|---|
| catggggtcc gcggcaaata tgccttggcg gatgcctctc tcaagatggc cgaccccaat | 120 |
| cgctttcgcg gcaaagacct tccggtcctg gaccagctga ccgaccctcc ggggtccgg | 180 |
| cgcgtgtacc acatccaggc gggcctaccg gacccgttcc agccccccag cctcccgatc | 240 |
| acggtttact acgccgtgtt ggagcgcgcc tgccgcagcg tgctcctaaa cgcaccgtcg | 300 |
| gaggcccccc agattgtccg cggggcctcc gaagacgtcc ggaaacaacc ctacaacctg | 360 |
| accatcgctt ggtttcggat gggaggcaac tgtgctatcc ccatcacggt catggagtac | 420 |
| accgaatgct cctacaacaa gtctctgggg gcctgtccca tccgaacgca gccccgctgg | 480 |
| aactactatg acagcttcag cgccgtcagc gaggataacc tggggttcct gatgcacgcc | 540 |
| cccgcgtttg agaccgccgg cacgtacctg cggctcgtga agataaacga ctggacggag | 600 |
| attacacagt ttatcctgga gcaccgagcc aagggctcct gtaagtacgc cctcccgctg | 660 |
| cgcatccccc cgtcagcctg cctgtccccc aggcctacc agcaggggt gacggtggac | 720 |
| agcatcggga tgctgccccg cttcatcccc gagaaccagc gcaccgtcgc cgtatacagc | 780 |
| ttgaagatcg ccgggtggca cgggcccaag gccccatac cgagcaccct gctgcccccg | 840 |
| gagctgtccg agacccccaa cgccacgcag ccagaactcg ccccggaaga ccccgaggat | 900 |
| tcggccctct tggaggaccc cgtggggacg gtggcgccgg tgcgagagc gtcagtatta | 960 |
| agcgggggag aattagatcg atgggaaaaa attcggttaa ggccaggggg aaagaagaag | 1020 |
| tacaagctaa agcacatcgt atgggcaagc agggagctag aacgattcgc agttaatcct | 1080 |
| ggcctgttag aaacatcaga aggctgtaga caaatactgg gacagctaca accatcccctt | 1140 |
| cagacaggat cagaggagct tcgatcacta taccaacacag tagcaaccct ctattgtgtg | 1200 |
| caccagcgga tcgagatcaa ggacaccaag gaagctttag acaagataga ggaagagcaa | 1260 |
| aacaagtcca agaagaaggc ccagcaggca gcagctgaca caggacacag caatcaggtc | 1320 |
| agccaaaatt accctatagt gcagaacatc caggggcaaa tggtacatca ggccatatca | 1380 |
| cctagaactt taaatgcatg ggtaaaagta gtagaagaga aggctttcag cccagaagtg | 1440 |
| atacccatgt tttcagcatt atcagaagga gccaccccac aggacctgaa cacgatgttg | 1500 |
| aacaccgtgg ggggacatca agcagccatg caaatgttaa agagaccat caatgaggaa | 1560 |
| gctgcagatt gggatagagt gcatccagtg catgcagggc ctattgcacc aggccagatg | 1620 |
| agagaaccaa ggggaagtga catagcagga actactagta cccttcagga caaatagga | 1680 |
| tggatgacaa ataatccacc tatcccagta ggagagatct acaagaggtg gataatcctg | 1740 |
| ggattgaaca agatcgtgag gatgtatagc cctaccagca ttctggacat aagacaagga | 1800 |
| ccaaaggaac cctttagaga ctatgtagac cggttctata aaactctaag agctgagcaa | 1860 |
| gcttcacagg aggtaaaaaa ttggatgaca gaaaccttgt tggtccaaaa tgcgaaccca | 1920 |
| gattgtaaga ccatcctgaa ggctctcggc ccagcggcta cactagaaga aatgatgaca | 1980 |
| gcatgtcagg gagtaggagg acccggccat aaggcaagag ttttggcgcc gcaaatccca | 2040 |
| ccaaactggc ataccgtc gatccaggac gccgcgacgc cttaccatcc cccggccacc | 2100 |
| ccgaacaaca tgggcctgat cgccggcgcg gtgggcggca gtctcctggc agccctggtc | 2160 |
| atttgcggaa ttgtgtactg gatgcgccgc cgcactcaaa aagcccccaaa gcgcatacgc | 2220 |
| ctcccccaca tccgggaaga cgaccagccg tcctcgcacc agcccttgtt ttactag | 2277 |

<210> SEQ ID NO 33
<211> LENGTH: 758
<212> TYPE: PRT
<213> ORGANISM: Artificial Sequence
<220> FEATURE:
<223> OTHER INFORMATION: amino acid sequence of gDgagW294A

<400> SEQUENCE: 33

| | | | | | | | | | | | | | | |
|---|---|---|---|---|---|---|---|---|---|---|---|---|---|---|
| Met | Gly | Gly | Ala | Ala | Ala | Arg | Leu | Gly | Ala | Val | Ile | Leu | Phe | Val | Val |
| 1 | | | | 5 | | | | | 10 | | | | | 15 | |

Ile Val Gly Leu His Gly Val Arg Gly Lys Tyr Ala Leu Ala Asp Ala
                20                  25                  30

Ser Leu Lys Met Ala Asp Pro Asn Arg Phe Arg Gly Lys Asp Leu Pro
            35                  40                  45

Val Leu Asp Gln Leu Thr Asp Pro Pro Gly Val Arg Arg Val Tyr His
50                  55                  60

Ile Gln Ala Gly Leu Pro Asp Pro Phe Gln Pro Ser Leu Pro Ile
65                  70                  75                  80

Thr Val Tyr Tyr Ala Val Leu Glu Arg Ala Cys Arg Ser Val Leu Leu
                85                  90                  95

Asn Ala Pro Ser Glu Ala Pro Gln Ile Val Arg Gly Ala Ser Glu Asp
            100                 105                 110

Val Arg Lys Gln Pro Tyr Asn Leu Thr Ile Ala Trp Phe Arg Met Gly
        115                 120                 125

Gly Asn Cys Ala Ile Pro Ile Thr Val Met Glu Tyr Thr Glu Cys Ser
    130                 135                 140

Tyr Asn Lys Ser Leu Gly Ala Cys Pro Ile Arg Thr Gln Pro Arg Trp
145                 150                 155                 160

Asn Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Lys Gly Ser Cys Lys Tyr Ala Leu Pro Leu Arg Ile Pro Pro
210                 215                 220

Ser Ala Cys Leu Ser Pro Gln Ala Tyr Gln Gln Gly Val Thr Val Asp
225                 230                 235                 240

Ser Ile Gly Met Leu Pro Arg Phe Ile Pro Glu Asn Gln Arg Thr Val
            245                 250                 255

Ala Val Tyr Ser Leu Lys Ile Ala Gly Trp His Gly Pro Lys Ala Pro
        260                 265                 270

Tyr Thr Ser Thr Leu Leu Pro Pro Glu Leu Ser Glu Thr Pro Asn Ala
    275                 280                 285

Thr Gln Pro Glu Leu Ala Pro Glu Asp Pro Glu Asp Ser Ala Leu Leu
290                 295                 300

Glu Asp Pro Val Gly Thr Val Ala Pro Gly Ala Arg Ala Ser Val Leu
305                 310                 315                 320

Ser Gly Gly Glu Leu Asp Arg Trp Glu Lys Ile Arg Leu Arg Pro Gly
                325                 330                 335

Gly Lys Lys Lys Tyr Lys Leu Lys His Ile Val Trp Ala Ser Arg Glu
            340                 345                 350

Leu Glu Arg Phe Ala Val Asn Pro Gly Leu Leu Glu Thr Ser Glu Gly
        355                 360                 365

Cys Arg Gln Ile Leu Gly Gln Leu Gln Pro Ser Leu Gln Thr Gly Ser
    370                 375                 380

Glu Glu Leu Arg Ser Leu Tyr Asn Thr Val Ala Thr Leu Tyr Cys Val
385                 390                 395                 400

His Gln Arg Ile Glu Ile Lys Asp Thr Lys Glu Ala Leu Asp Lys Ile
            405                 410                 415
Glu Glu Glu Gln Asn Lys Ser Lys Lys Lys Ala Gln Gln Ala Ala Ala
        420                 425                 430
Asp Thr Gly His Ser Asn Gln Val Ser Gln Asn Tyr Pro Ile Val Gln
        435                 440                 445
Asn Ile Gln Gly Gln Met Val His Gln Ala Ile Ser Pro Arg Thr Leu
    450                 455                 460
Asn Ala Trp Val Lys Val Val Glu Glu Lys Ala Phe Ser Pro Glu Val
465                 470                 475                 480
Ile Pro Met Phe Ser Ala Leu Ser Glu Gly Ala Thr Pro Gln Asp Leu
                485                 490                 495
Asn Thr Met Leu Asn Thr Val Gly Gly His Gln Ala Ala Met Gln Met
            500                 505                 510
Leu Lys Glu Thr Ile Asn Glu Glu Ala Ala Asp Trp Asp Arg Val His
        515                 520                 525
Pro Val His Ala Gly Pro Ile Ala Pro Gly Gln Met Arg Glu Pro Arg
    530                 535                 540
Gly Ser Asp Ile Ala Gly Thr Thr Ser Thr Leu Gln Glu Gln Ile Gly
545                 550                 555                 560
Trp Met Thr Asn Asn Pro Pro Ile Pro Val Gly Glu Ile Tyr Lys Arg
                565                 570                 575
Trp Ile Ile Leu Gly Leu Asn Lys Ile Val Arg Met Tyr Ser Pro Thr
            580                 585                 590
Ser Ile Leu Asp Ile Arg Gln Gly Pro Lys Glu Pro Phe Arg Asp Tyr
        595                 600                 605
Val Asp Arg Phe Tyr Lys Thr Leu Arg Ala Glu Gln Ala Ser Gln Glu
    610                 615                 620
Val Lys Asn Trp Met Thr Glu Thr Leu Leu Val Gln Asn Ala Asn Pro
625                 630                 635                 640
Asp Cys Lys Thr Ile Leu Lys Ala Leu Gly Pro Ala Ala Thr Leu Glu
                645                 650                 655
Glu Met Met Thr Ala Cys Gln Gly Val Gly Pro Gly His Lys Ala
            660                 665                 670
Arg Val Leu Ala Pro Gln Ile Pro Pro Asn Ala His Ile Pro Ser Ile
        675                 680                 685
Gln Asp Ala Ala Thr Pro Tyr His Pro Pro Ala Thr Pro Asn Asn Met
    690                 695                 700
Gly Leu Ile Ala Gly Ala Val Gly Gly Ser Leu Leu Ala Ala Leu Val
705                 710                 715                 720
Ile Cys Gly Ile Val Tyr Trp Met Arg Arg Thr Gln Lys Ala Pro
                725                 730                 735
Lys Arg Ile Arg Leu Pro His Ile Arg Glu Asp Asp Gln Pro Ser Ser
            740                 745                 750
His Gln Pro Leu Phe Tyr
        755

<210> SEQ ID NO 34
<211> LENGTH: 2277
<212> TYPE: DNA
<213> ORGANISM: Artificial Sequence
<220> FEATURE:
<223> OTHER INFORMATION: nucleotide sequence encoding gDgagW294A

<400> SEQUENCE: 34

```
atggggggggg ctgccgccag gttgggggcc gtgattttgt ttgtcgtcat agtgggcctc      60
catgggtcc   gcggcaaata tgccttggcg gatgcctctc tcaagatggc cgaccccaat     120
cgctttcgcg  gcaaagacct tccggtcctg gaccagctga ccgaccctcc ggggtccgg      180
cgcgtgtacc  acatccaggc gggcctaccg gacccgttcc agcccccag  cctcccgatc    240
acggtttact  acgccgtgtt ggagcgcgcc tgccgcagcg tgctcctaaa cgcaccgtcg     300
gaggcccccc  agattgtccg cggggcctcc gaagacgtcc ggaaacaacc ctacaacctg     360
accatcgctt  ggtttcggat gggaggcaac tgtgctatcc ccatcacggt catggagtac     420
accgaatgct  cctacaacaa gtctctgggg gcctgtccca tccgaacgca gccccgctgg     480
aactactatg  acagcttcag cgccgtcagc gaggataacc tggggttcct gatgcacgcc     540
cccgcgtttg  agaccgccgg cacgtacctg cggctcgtga agataaacga ctggacggag     600
attacacagt  ttatcctgga gcaccgagcc aagggctcct gtaagtacgc cctcccgctg     660
cgcatcccc   cgtcagcctg cctgtcccc  caggcctacc agcaggggt  gacggtggac     720
agcatcggga  tgctgccccg cttcatcccc gagaaccagc gcaccgtcgc cgtatacagc     780
ttgaagatcg  ccgggtggca cgggcccaag gccccataca cgagcaccct gctgcccccg     840
gagctgtccg  agacccccaa cgccacgcag ccagaactcg ccccggaaga ccccgaggat     900
tcggccctct  tggaggaccc cgtggggacg gtggcgccgg tgcgagagc  gtcagtatta     960
agcggggggag aattagatcg atgggaaaaa attcggttaa ggccagggg  aaagaagaag    1020
tacaagctaa  agcacatcgt atgggcaagc agggagctag aacgattcgc agttaatcct    1080
ggcctgttag  aaacatcaga aggctgtaga caaatactgg gacagctaca accatccctt    1140
cagacaggat  cagaggagct tcgatcacta tacaacacag tagcaaccct ctattgtgtg    1200
caccagcgga  tcgagatcaa ggacaccaag gaagctttag acaagataga ggaagagcaa    1260
aacaagtcca  agaagaaggc ccagcaggca gcagctgaca caggacacag caatcaggtc    1320
agccaaaatt  accctatagt gcagaacatc caggggcaaa tggtacatca ggccatatca    1380
cctagaactt  taaatgcatg ggtaaaagta gtagaagaga aggctttcag cccagaagtg    1440
atacccatgt  tttcagcatt atcagaagga gccaccccac aggacctgaa cacgatgttg    1500
aacaccgtgg  ggggacatca agcagccatg caaatgttaa agagaccat  caatgaggaa    1560
gctgcagatt  gggatagagt gcatccagtg catgcagggc ctattgcacc aggccagatg    1620
agagaaccaa  ggggaagtga catagcagga actactagta cccttcagga caaatagga    1680
tggatgacaa  ataatccacc tatcccagta ggagagatct acaagaggtg gataatcctg    1740
ggattgaaca  agatcgtgag gatgtatagc cctaccagca ttctggacat aagacaagga    1800
ccaaaggaac  cctttagaga ctatgtagac cggttctata aaactctaag agctgagcaa    1860
gcttcacagg  aggtaaaaaa ttggatgaca gaaaccttgt tggtccaaaa tgcgaaccca    1920
gattgtaaga  ccatcctgaa ggctctcggc ccagcggcta cactagaaga aatgatgaca    1980
gcatgtcagg  gagtaggagg acccggccat aaggcaagag ttttggcgcc gcaaatccca    2040
ccaaacgcgc  acataccgtc gatccaggac gccgcgacgc cttaccatcc cccggccacc    2100
ccgaacaaca  tgggcctgat cgccggcgcg gtgggcggga gtctcctggc agccctggtc    2160
atttgcggaa  ttgtgtactg gatgcgccgc cgcactcaaa aagccccaaa gcgcatacgc    2220
ctcccccaca  tccgggaaga cgaccagccg tcctcgcacc agcccttgtt ttactag      2277
```

<210> SEQ ID NO 35

<211> LENGTH: 2682
<212> TYPE: DNA
<213> ORGANISM: Artificial Sequence
<220> FEATURE:
<223> OTHER INFORMATION: nucleotide sequence encoding gDNP

<400> SEQUENCE: 35

```
atggggggggg ctgccgccag gttgggggcc gtgattttgt ttgtcgtcat agtgggcctc      60
catgggtcc gcggcaaata tgccttggcg gatgcctctc tcaagatggc cgaccccaat      120
cgctttcgcg gcaaagacct tccggtcctg gaccagctga ccgaccctcc ggggtccgg       180
cgcgtgtacc acatccaggc gggcctaccg gacccgttcc agcccccag cctcccgatc      240
acggtttact acgccgtgtt ggagcgcgcc tgccgcagcg tgctcctaaa cgcaccgtcg      300
gaggcccccc agattgtccg cggggcctcc gaagacgtcc ggaaacaacc ctacaacctg      360
accatcgctt ggtttcggat gggaggcaac tgtgctatcc ccatcacggt catggagtac      420
accgaatgct cctacaacaa gtctctgggg gcctgtccca tccgaacgca gccccgctgg      480
aactactatg acagcttcag cgccgtcagc gaggataacc tggggttcct gatgcacgcc      540
cccgcgtttg agaccgccgg cacgtacctg cggctcgtga agataaacga ctggacggag      600
attacacagt ttatcctgga gcaccgagcc aagggctcct gtaagtacgc cctcccgctg      660
cgcatcccccc cgtcagcctg cctgtccccc caggcctacc agcaggggt gacggtggac      720
agcatcggga tgctgccccg cttcatcccc gagaaccagc gcaccgtcgc cgtatacagc      780
ttgaagatcg ccgggtggca cgggcccgcg tcccaaggca ccaaacggtc ttacgaacag      840
atggagactg atggagaacg ccagaatgcc actgaaatca gcgcatccgt cggaaaaatg      900
attggtggaa ttggacgatt ctacatccaa atgtgcaccg aactcaaact cagtgattat      960
gagggacggt tgatccaaaa cagcttaaca atagagagaa tggtgctctc tgcttttgac      1020
gaaaggagaa ataaatacct ggaagaacat cccagtgcgg ggaaagatcc taagaaaact      1080
ggaggaccta tatacaggag agtaaacgga aagtggatga gagaactcat cctttatgac      1140
aaagaagaaa taaggcgaat ctggcgccaa actaataatg gtgacgatgc aacggctggt      1200
ctgactcaca tgatgatctg gcattccaat ttgaatgatg caacttatca gaggacaaga      1260
gctcttgttc gcaccggaat ggatcccagg atgtgctctc tgatgcaagg ttcaactctc      1320
cctaggaggt ctggagccgc aggtgctgca gtcaaaggag ttggaacaat ggtgatggaa      1380
ttggtcagga tgatcaaacg tgggatcaat gatcggaact tctggagggg cgagaatgga      1440
cgaaaaacaa gaattgctta tgaaagaatg tgcaacattc tcaaagggaa atttcaaact      1500
gctgcacaaa aagcaatgat ggatcaagtg agagagagcc ggaacccagg gaatgctgag      1560
ttcgaagatc tcactttttct agcacggtct gcactcatat tgagagggtc ggttgctcac      1620
aagtcctgcc tgcctgcctg tgtgtatgga cctgccgtag ccagtgggta cgactttgaa      1680
agagagggat actctctagt cggaatagac ccttttcagac tgcttcaaaa cagccaagtg      1740
tacagcctaa tcagaccaaa tgagaatcca gcacacaaga gtcaactggt gtggatggca      1800
tgccattctg ccgcatttga agatctaaga gtattaagct tcatcaaagg gacgaaggtg      1860
ctcccaagag ggaagctttc cactagagga gttcaaattg cttccaatga aaatatggat      1920
gctatggaat caagtacact tgaactgaga agcaggtact gggccataag gaccagaagt      1980
ggggggaaaca ccaatcaaca gagggcatct gcgggccaaa tcagcataca acctacgttc      2040
tcagtacaga gaaatctccc tttttgacaga acaaccatta tggcagcatt caatgggaat      2100
acagagggaa gaacatctga catgaggacc gaaatcataa ggatgatgga aagtgcaaga      2160
```

```
ccagaagatg tgtctttcca ggggcgggga gtcttcgagc tctcggacga aaaggcagcg    2220
agcccgatcg tgccttcctt tgacatgagt aatgaaggat cttatttctt cggagacaat    2280
gcagaggagt acgacaatgg gcccaaggcc ccatacacga gcaccctgct gcccccggag    2340
ctgtccgaga cccccaacgc cacgcagcca gaactcgccc ggaagaccc cgaggattcg     2400 gccctcttgg aggacccgt ggggacggtg gcgccgcaaa tcccaccaaa ctggcacata    2460
ccgtcgatcc aggacgccgc gacgccttac catcccccgg ccaccccgaa caacatgggc    2520
ctgatcgccg gcgcggtggg cggcagtctc ctggcagccc tggtcatttg cggaattgtg    2580
tactggatgc gccgccgcac tcaaaaagcc ccaaagcgca tacgcctccc ccacatccgg    2640
gaagacgacc agccgtcctc gcaccagccc ttgttttact ag                       2682

<210> SEQ ID NO 36
<211> LENGTH: 1185
<212> TYPE: DNA
<213> ORGANISM: Artificial Sequence
<220> FEATURE:
<223> OTHER INFORMATION: nucleotide sequence encoding gDW294A

<400> SEQUENCE: 36 atggggggg ctgccgccag gttggggggcc gtgattttgt ttgtcgtcat agtgggcctc      60 catgggtcc gcggcaaata tgccttggcg gatgcctctc tcaagatggc cgaccccaat     120
cgctttcgcg gcaaagacct tccggtcctg gaccagctga ccgaccctcc gggggtccgg    180
cgcgtgtacc acatccaggc gggcctaccg gacccgttcc agccccccag cctcccgatc    240
acggtttact acgccgtgtt ggagcgcgcc tgccgcagcg tgctcctaaa cgcaccgtcg    300
gaggcccccc agattgtccg cggggcctcc gaagacgtcc ggaaacaacc ctacaacctg    360
accatcgctt ggtttcggat gggaggcaac tgtgctatcc ccatcacggt catggagtac    420
accgaatgct cctacaacaa gtctctgggg gcctgtccca tccgaacgca gcccgctgg    480 aactactatg acagcttcag cgccgtcagc gaggataacc tggggttcct gatgcacgcc    540
cccgcgtttg agaccgccgg cacgtacctg cggctcgtga agataaacga ctggacggag    600
attacacagt ttatcctgga gcaccgagcc aagggctcct gtaagtacgc cctcccgctg    660
cgcatccccc cgtcagcctg cctgtccccc aggcctacc agcagggggt gacggtggac    720
agcatcggga tgctgccccg cttcatcccc gagaaccagc gcaccgtcgc cgtatacagc    780
ttgaagatcg ccgggtggca cgggcccaag gccccataca cgagcaccct gctgcccccg    840
gagctgtccg agacccccaa cgccacgcag ccagaactcg ccccggaaga ccccgaggat    900
tcggccctct tggaggaccc cgtggggacg gtggcgccgc aaatcccacc aaacgcgcac    960
ataccgtcga tccaggacgc cgcgacgcct taccatcccc cggccacccc gaacaacatg    1020
ggcctgatcg ccggcgcggt gggcggcagt ctcctggcag ccctggtcat ttgcggaatt    1080
gtgtactgga tgcgccgccg cactcaaaaa gccccaaagc gcatacgcct ccccacatc    1140 cgggaagacg accagccgtc ctcgcaccag cccttgtttt actag                    1185

<210> SEQ ID NO 37
<211> LENGTH: 2199
<212> TYPE: DNA
<213> ORGANISM: Artificial Sequence
<220> FEATURE:
<223> OTHER INFORMATION: nucleotide sequence encoding NBEF gDE7E6E5

<400> SEQUENCE: 37
```

```
atgggggggg ctgccgccag gttggggggcc gtgattttgt ttgtcgtcat agtgggcctc    60
catgggggtcc gcggcaaata tgccttggcg gatgcctctc tcaaggcggc cgacccccgct   120
cgctttcgcg gcaaagacct tccggtcgcg gacgcggcgg ccgccccctcc ggggggtccgg   180
cgcgtgtacc acatccaggc gggcctaccg gacccgttcc agccccccag cctcccgatc   240
acggtttact acgccgtgtt ggagcgcgcc tgccgcagcg tgctcctaaa cgcaccgtcg   300
gaggccccccc agattgtccg cggggcctcc gaagacgtcc ggaaacaacc ctacaacctg   360
accatcgctt ggtttcggat gggaggcaac tgtgctatcc ccatcacggt catggagtac   420
accgaatgct cctacaacaa gtctctgggg gcctgtccca tccgaacgca gccccgctgg   480
aactactatg acagcttcag cgccgtcagc gaggataacc tggggttcct gatgcacgcc   540
cccgcgtttg agaccgccgg cacgtacctg cggctcgtga agataaacga ctggacggag   600
attacacagt ttatcctgga gcaccgagcc aagggctcct gtaagtacgc cctcccgctg   660
cgcatcccccc cgtcagcctg cctgtccccc caggcctacc agcaggggggt gacggtggac   720
agcatcggga tgctgccccg cttcatcccc gagaaccagc gcaccgtcgc cgtatacagc   780
ttgaagatcg ccgggtggca cgggcccccat ggagatacac ctacattgca tgaatatatg   840
ttagatttgc aaccagagac aactgatctc tactgttatg agcaattaaa tgacagctca   900
gaggaggagg atgaaataga tggtccagct ggacaagcag aaccggacag agcccattac   960
aatattgtaa ccttttgttg caagtgtgac tctacgcttc ggttgtgcgt acaaagcaca  1020
cacgtagaca ttcgtacttt ggaagacctg ttaatgggca cactaggaat tgtgtgcccc  1080
atctgttctc agaaaccagg cgcccaccaa aagagaactg caatgtttca ggacccacag  1140
gagcgaccca gaaagttacc acagttatgc acagagctgc aaacaactat acatgatata  1200
atattagaat gtgtgtactg caagcaacag ttactgcgac gtgaggtata tgactttgct  1260
tttcgggatt tatgcatagt atatagagat gggaatccat atgctgtatg tgataaatgt  1320
ttaaagtttt attctaaaat tagtgagtat agacattatt gttatagttt gtatggaaca  1380
acattagaac agcaatacaa caaaccgttg tgtgatttgt taattaggtg tattaactgt  1440
caaaagccac tgtgtcctga agaaaagcaa agacatctgg acaaaaagca aagattccat  1500
aatataaggg gtcggtggac cggtcgatgt atgtcttgtt gcagatcatc aagaacacgt  1560
agagaaaccc agctggcggc cgcctgcatc cacaacatta ctggcgtgct ttttgctttg  1620
cttttgtgtgc ttttgtgtgt ctgcctatta atacgtccgc tgcttttgtc tgtgtctaca  1680
tacacatcat taataatatt ggtattacta ttgtggataa cagcagcctc tgcgtttagg  1740
tgtttttattg tatatattat atttgtttat ataccattat ttttaataca tacacatgca  1800
cgcttttttaa ttacagggcc caaggcccca tacacgagca ccctgctgcc cccgagctg   1860
tccgagaccc ccaacgccac gcagccagaa ctcgccccgg aagacccccga ggattcggcc  1920
ctcttggagg accccgtggg gacggtggcg ccgcaaatcc caccaaactg gcacataccg  1980
tcgatccagg acgccgcgac gccttaccat cccccgccca cccgaacaa catgggcctg  2040
atcgccggcg cggtgggcgg cagtctcctg gcagccctgg tcatttgcgg aattgtgtac  2100
tggatgcgcc gccgcactca aaaagcccca aagcgcatac gcctcccccca catccgggaa  2160
gacgaccagc cgtcctcgca ccagcccttg ttttactag                          2199
```

CONSTRUCTS FOR ENHANCING IMMUNE RESPONSES

CROSS-REFERENCE TO RELATED APPLICATIONS

The present application is a continuation of U.S. patent application Ser. No. 15/639,296, filed on Jun. 30, 2017, allowed, which is a continuation of U.S. patent application Ser. No. 14/628,784, filed on Feb. 23, 2015, now U.S. Pat. No. 9,724,406, which is a continuation of U.S. patent application Ser. No. 13/239,771, filed on Sep. 22, 2011, now U.S. Pat. No. 8,962,816, which is a continuation of U.S. patent application Ser. No. 12/438,889, filed on Feb. 25, 2009, abandoned, which is a National Stage application of PCT/US2007/018939, filed on Aug. 28, 2007, which claims priority under 35 U.S.C. § 119(e) to U.S. Provisional Patent Application No. 60/840,526, filed on Aug. 28, 2006, each of which application is incorporated by reference in its entirety herein.

STATEMENT REGARDING FEDERALLY SPONSORED RESEARCH OR DEVELOPMENT

This invention was made with government support under 5 P01 AI052271, awarded by the National Institutes of Health (NIH). The government has certain rights in the invention.

FIELD OF THE INVENTION

Embodiments of the present invention relate in general to chimeric (fusion) protein constructs including a herpesvirus glycoprotein D (gD) and a heterologous polypeptide (e.g., antigen) that enhance the immune response against the heterologous polypeptide (e.g., antigen) in a subject.

BACKGROUND OF THE INVENTION gD is the receptor-binding glycoprotein of herpesviruses (Fusco et al. (2005) *Proc. Natl. Acad. Sci. U.S.A.* 102:9323). The gD ectodomain is organized in two structurally and functionally differentiated regions. The amino-terminus includes the signal sequence and receptor-binding sites, and the carboxy-terminus includes the pro-fusion domain and the transmembrane domain. gD interacts with two alternative receptors belonging to unrelated protein families, the herpesvirus entry mediator (HVEM) and the nectins (Geraghty et al. (1998) *Science* 280:1618; Montgomery et al. (1996) *Cell* 87:427; Cocchi et al. (1998) *J. Virol.* 72:9992; Warner et al. (1998) *Virology* 246:179; Lopez et al. (2000) *J. Virol.* 74:1267). HVEM is expressed on dendritic cells and the B and T lymphocyte attenuator (BTLA) is expressed on activated T and B lymphocytes. The interaction between HVEM and BTLA results in the down-regulation of immune responses.

BRIEF DESCRIPTION OF THE DRAWINGS

FIG. 3A depicts a FACS analysis of the gag-specific CD8/IFN-$\gamma^+$ response in peripheral blood mononuclear cells (PBMC) from mice immunized with DNA vaccine expressing either HIV-1 gag or HIV-1 gag fused to HSV-1 gD (gDgag). Numbers on the right corner represent percentage $CD8^+$/IFN-$\gamma^+$ cells over total of $CD8^+$ cells. FIG. 3B graphically depicts PBMC from mice immunized with AdC68 vectors carrying either genes encoding gag or gDgag, inoculated with different amounts of virus particles per mouse.

FIG. 6 depicts the E7-specific $CD8^+$ IFN-$\gamma$ response in mice immunized with DNA vaccines expressing non-mutated (gDE7) or mutated gD (SgDE7). This mutation (SgD) was designed to increase binding between gD and HVEM. Mice were immunized with pgDE7 or pSgDE7 and 14 days later peripheral blood mononuclear cells were investigated by intracellular cytokine staining for E7-specific $CD8^+$ IFN-$\gamma$ response. Numbers in the corners represent percentage $CD8^+$/IFN-$\gamma^+$ cells over total of $CD8^+$ cells.

(FIG. 10A) Microscopy was performed with a Leica TCS SP2 Confocal Microscope at 400× final magnification. (FIG. 10B) Cell suspensions were analyzed using an EPICS XL (Beckman-Coulter, Inc., Miami, Fla.). B78H1/3E5 cells were cultured with either AdC68gDgag-infected CHO-CAR cells (darker line) or non-infected CHO-CAR cells (lighter line). Data on graph show cells which are positive for GFP.

FIG. 11 depicts the gag-specific CD8$^+$ T cell response in mice immunized with AdC68 vectors. PBMC and splenocytes from mice immunized with 1×10$^9$ vp of AdC68 vectors carrying either gag, gDgag or gD were tested. Percentage represents CD8$^+$/IFN-γ$^+$ cells over total of CD8$^+$ cells. CD8$^+$/IFN-γ$^+$ frequencies in all groups stimulated with an unrelated control peptide were below 0.20%. Data shown are representative of two performed experiments.

FIG. 18A, the gag insertion is connected to the gD ectodomain core by a long flexible linker. FIG. 18B, a superposition of the native gD X-ray structure (2C36) (darker ribbon) and that of the gD-gag chimera model (lighter ribbon) shows that the gag insert repositions the C-terminus of native gD away from the HVEM binding pocket. The dashed line indicates an 11 residue gD loop segment that like the first 22 N-terminal residues (not shown) is unresolved in the X-ray structure and presumed to be highly flexible (Krummenacher et al., EMBO J. 24, 4144-53, 2005). FIG. 18C, gD-gag chimera model in the HVEM ligated conformation with HVEM positioned as observed in the gD-HVEM complex X-ray structure (1JMA). The gD N-terminus changes conformation upon formation of the HVEM complex. FIG. 18D, a superposition of the native gD X-ray structure (2C36) (darker ribbon) with the gD-gag chimera model (lighter ribbon) in the HVEM-bound conformation shows that the gag insert does not disrupt the gD core domain.

FIG. 23A, intracellular cytokine staining of E7- and gag-specific CD8⁺ T cells were carried out on PBMCs from mice i.m. immunized with DNA vaccines (upper graphs) or AdC68 vectors (lower graphs) expressing either gD, E7E6E5, gD-E7E6E5, gag or gD-gag, after stimulation with E7 or gag peptide and cell surface staining for CD8 (FITC) and intracellular staining for IFN-γ (PE). PBMCs were isolated from animals 14 days after DNA vaccination or 10 days after application of AdC68 vector. The numbers in the right upper corners show frequencies of IFN-γ-producing CD8⁺ T cells as a percentage of all CD8⁺ T cells. Frequencies of IFN-γ⁺/CD8⁺ T cells stimulated with an unrelated control peptide were below 0.2% in all groups. FIG. 23B, Gag-specific CD8⁺ T cell frequencies were determined 10 days after immunization of mice with decreasing doses of either AdC68gag (open bars) or AdC68gD-gag (black bars) vectors. FIG. 23C, The kinetics of E7-specific CD8⁺ T cell responses induced by the AdC68gD-E7E6E5 vector were analyzed from BPMCs of mice immunized with either AdC68E7E6E5 (squares), AdC68gD (diamonds) or AdC68gD-E7E6E5 (triangles) vectors at different days after a single dose of $10^{10}$ vps of the vaccines.

FIG. 24A, E7-specific IFN-γ⁺CD8⁺ responses were evaluated with splenocytes from mice immunized with one dose of DNA vaccines expressing the E7E6E5 polypeptide either within wild-type gD (pgD-E7E6E5), a mutated gD that shows loss of binding to HVEM (NBEFgD-E7E6E5) or that shows enhanced binding to HVEM (SgD-E7E6E5). FIG. 24B, splenocytes from mice immunized with one dose of DNA vaccines carrying E7 fused to either wild type gD (gD-E7) or mutated gD with high affinity to HVEM (SgD-E7) were evaluated for E7-specific IFN-γ⁺CD8⁺ response. PBMCs were isolated 14 days after DNA vaccine immunizations.

FIGS. 26A-26C. CD8⁺ T cells induced by gD-antigen chimeric protein are functional in vivo. Protection against TC-1 tumor challenge was evaluated in mice vaccinated with DNA (FIG. 26A) or AdC68vectors (FIG. 26B) expressing either gD (circles), E7E6E5 (diamonds) or gD-E7E6E5 (squares). FIG. 26C, Protection to TC-1 tumor challenge in mice vaccinated with DNA vaccine expressing either NBEFgD-E7E6E5 (diamonds), SgD-E7E6E5 (squares), gD-E7 (circles) or SgD-E7 (triangles) chimeric genes. Mice were challenged 14 and 10 days after vaccination with DNA and AdC68 vectors, respectively. Tumor development was followed up for up to 60 days after challenge.

FIG. 27A, RNA isolated from non-infected cells and from cells infected with AdC68gD (white bars), AdC68E7E6E5 (gray bars) or AdC68gD-E7E6E5 (black bars) were reverse transcribed and quantified by Real-Time PCR. After quantification of GAPDH mRNA copies, all samples were normalized to $10^9$ GAPDH mRNA copies. Specific mRNA copies were quantified using gD, E7, E6, and E5 specific primers. Neither E7, E6 nor E5 mRNA were detected in cells infected with AdC68gD, and no gD specific mRNA was detected in cells infected with AdC68E7E6E5. mRNA levels were assessed in three independent experiments and each sample was investigated in triplicates. p values from two-tail student's t test are shown on top of the bars. FIG. 27B, confocal microscopy was carried out with CHO/CAR cells infected with AdC68 expressing either gD, E7E6E5 or gD-E7E6E5, then permeabilized and stained with anti-gD DL-6 MAb and anti-mouse IgG conjugated with FITC. Immunoflorescence is shown on the top panel while differential interference contrast (DIC) microscopy is shown on the bottom panel. Cells were examined with a Leica TCS SP2 Confocal Microscope at 400× magnification.

FIG. 28A, frequencies of E7-specific CD8⁺ T cells in PBMC (top) or spleens (bottom) from naïve mice or mice immunized with AdC68 vector expressing either gD, E7E6E5 or gD-E7E6E5 were determined 10 days after immunization. FIG. 28B, frequencies of E7-specific CD8⁺ T cells in PBMC (top) or spleens (bottom) from naïve mice or mice immunized with DNA vaccines expressing either gD, E7E6E5 or gD-E7E6E5 were determined 14 days after immunization. FIG. 28C, prime and boost regimens with pgD-E7E6E5 and AdC68gD-E7E6E5 vectors. Mice immunized with one dose of pgD-E7E6E5 vector were boosted after 90 days with AdC68gD-E7E6E5 (open bars), while mice immunized with AdC68gD-E7E6E5 were boosted after 90 days with pgD-E7E6E5 (black bars). Detection of E7-specific CD8⁺ T response was carried out after stimulation with a MHC class I restricted E7 peptide and cell surface staining for CD8 (FITC) and intracellular staining for IFN-γ (PE). The numbers in the right upper corners show the frequencies of E7-specific CD8⁺ T cells, as percentages of IFN-γ-producing CD8⁺ T cells over all detected CD8⁺ T cells. IFN-γ-producing CD8⁺ cell frequencies in all groups stimulated with an unrelated peptide or in the absence of stimulus were below 0.2%. The data shown in a and b are from one representative experiment of four performed.

FIG. 30A, for post-challenge vaccination, groups of 10 mice were s.c. inoculated with TC-1, then 5 days later immunized with either AdC68gD (triangles), AdC68E7E6E5 (circles) or AdC68gD-E7E6E5 (squares). FIG. 30B, for pre-challenge vaccination, groups of 10 mice vaccinated one year earlier with AdC68 vectors carrying either gD (triangles), E7E6E5 (circles) or gD-E7E6E5 (squares) were s.c. challenged with TC-1. For all TC-1 challenge experiments animals were monitored 3 times per week for evidence of tumor growth over a period of 60 days.

FIG. 31A, ICS of E7-specific CD8+ T cells in spleen from non-challenged mice (top) or mice challenged with TC-1 cells (top). Frequencies of IFN-γ-producing E7-specific CD8+ T cells in spleen were determined as in FIG. 2 legend. FIG. 31B, E7-tetramer staining of CD8+ T cells isolated from spleen, blood and liver of mice challenged (white bars) or not (black bars) with TC-1 cells. Data represent percentages of E7-tetramer+ CD8+ T cells over all detected CD8+ T cells. E7-tetramer+ CD8+ cells were not detected in mice immunized with either AdC68gD or AdC68E7E6E5.

FIGS. 32A-32C. CD8+ T cell response and phenotypic profile in mice immunized with AdC68 vectors and subsequently challenged with TC-1 cells. Lymphocytes were isolated 3 days after TC-1 challenge from animals immunized with AdC68gD-E7E6E5 and 7 days after challenge from animals immunized with either AdC68gD or AdC68E7E6E5. E7-specific CD8+ T response were determined in spleen, PBMC and TIL by ICS (FIG. 32A) and E7-tetramer staining (FIG. 32B). ICS data was determined as in FIG. 2 legend, while E7-tetramer staining data represent percentages of E7-tetramer+CD8+ T cells over all detected CD8+ T cells. E7-specific IFN-γ+CD8+ cells and E7-tetramer+CD8+ cells were not detected in mice immunized with either AdC68gD or AdC68E7E6E5. FIG. 32C, phenotype analysis of splenocytes, PBMCs and TILs were determined with cells isolated from mice immunized with AdC68gD-E7E6E5 (black line) or AdC68gD (dotted black line) then challenged with TC-1. Cells were stained with E7-tetramer-APC and anti-CD8-PerCP, in combination with antibodies to CD44, CD62L, CD27, Bcl2, BTLA, CTLA-4 and PD-1. CD8+ T cells isolated from either naïve mice or mice immunized with AdC68E7E6E5 showed similar phenotype profiles as CD8+ T cells isolated from mice immunized with AdC68gD.

FIGS. 33A-33C. Comparison of CD8+ T cell responses and phenotype profiles induced by AdC68 vectors in wild-type and HPV-16 E6/E7-tg mice. One-year old E6/E7-tg mice were vaccinated with AdC68 vectors expressing either gD, E7E6E5 or gD-E7E6E5, and 1-year old C57Bl/6 mice were vaccinated with AdC68gD-E7E6E5 vector. Ten days later frequencies and phenotypes of E7-specific CD8+ T cells were determined. FIG. 33A, E7-specific CD8+ T cells isolated from spleens of E6/E7-tg mice immunized with AdC68gD, AdC68E7E6E5 or AdC68gD-E7E6E5, or from spleen of wild-type mice immunized with AdC68gD-E7E6E5 were tested by ICS. Frequencies of IFN-γ-producing E7-specific CD8+ T cells in spleen were determined as described in legend to FIG. 2. FIG. 33B, E7-tetramer staining of CD8+ T cells was performed with splenocytes and PBMC from wild-type and E6/E7-tg mice, and with lymphocytes from thyroids of E6/E7-tg mice. Data show percentages of E7-tetramer+CD8+ T cells over all detected CD8+ T cells. ND, not determined. FIG. 33C, phenotypic profile of E7-specific CD8+ T cells were determined using cells isolated from spleen and blood of AdC68gD-E7E6E5 vaccinated E6/E7 tg (filled gray) and wild-type (black line) mice, and from cells isolated from thyroid of E6/E7 tg mice vaccinated with AdC68gD-E7E6E5. CD8+ T cells isolated from E6/E7 tg naïve mice were used as controls (black dotted line).

DETAILED DESCRIPTION

Figure 1:
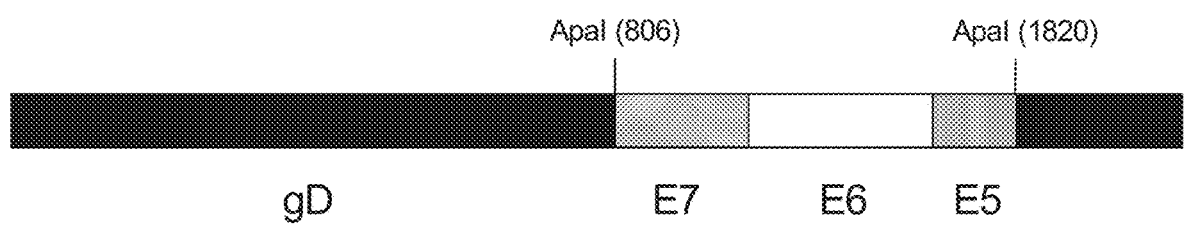
FIG. 1 depicts a schematic representation of the chimeric gene gDE7E6E5. The HPV-16 E5, E6 and E7 genes without respective start and stop codons were linked in tandem and incorporated into the HSV-1 gD gene ApaI site, which corresponds to amino acid 244 in the gD mature form.

The invention provides chimeric, or fusion, proteins in which one or more antigens is inserted into the C terminal region of a mature HSV gD protein. Such fusion proteins enhance the immune response of a host against the antigen(s) to a much greater degree than is observed without the gD. The gD chimeric proteins of the present invention are particularly suitable for use as genetic vaccines (e.g., DNA vaccines or viral vector vaccines) to therapeutically or prophylactically treat a subject. Thus, the invention also provides nucleic acid molecules which encode fusion proteins of the invention.

Glycoprotein D

Glycoprotein D (gD) is an envelope glycoprotein found on Herpes simplex viruses such as HSV-1 or HSV-2 and is expressed in cells infected by the viruses. An HSV gD has a 25-amino acid amino-terminal signal sequence and a carboxy-terminal transmembrane domain. The signal sequence is typically cleaved in the mature form of the protein. The amino acid sequence of HSV-1 gD is shown in SEQ ID NO:27 (amino acids 1-25 are the signal sequence; amino acids 26-394 are mature HSV-1 gD); a coding sequence for SEQ ID NO:27 is shown in SEQ ID NO:26. The amino acid sequence of HSV-2 gD is shown in SEQ ID NO:29 (amino acids 1-25 are the signal sequence; amino acids 26-393 are mature HSV-2 gD); a coding sequence for SEQ ID NO:25 is shown in SEQ ID NO:28.

An HSV gD or mutant thereof which is useful in the present invention has the ability to interact with HVEM and, in addition, may have one or more of the following properties: 1) ability to stimulate a CD8+ T cell response to the fusion partner; 2) ability to disrupt an HVEM-BTLA pathway activity; 3) ability to interact with nectin-1; 4) ability to mediate cell entry by an HSV-1 and/or HSV-2 virus; and 5) ability to mediate cell-to-cell spread of HSV-1 and/or HSV-2. Thus, as used herein, a "gD" or an "immunostimulatory portion of a gD" refers to a polypeptide having an amino acid sequence of a wild-type gD or a mutant thereof which retains one or more gD activities.

gD chimeric (fusion) proteins of the invention comprise at least two, preferably three polypeptide segments. The first polypeptide segment comprises at least amino acids 1-240 of a mature Herpes simplex virus (HSV) glycoprotein D; in preferred embodiments the first polypeptide segment does not comprise a full length mature glycoprotein D; in this case a third polypeptide segment is included. The second polypeptide segment, the N terminus of which is linked to the C terminus of the first polypeptide segment, comprises at least one antigen which is not an HSV glycoprotein D antigen. The third polypeptide comprises a C terminal portion of the HSV glycoprotein D; the N terminus of the third polypeptide segment is linked to the C terminus of the second polypeptide segment. Thus, in certain embodiments an antigen is fused to the carboxy-terminal region of gD. In other aspects, an antigen is inserted within the carboxy-terminal amino acid sequence of gD such that the amino-terminal end of the gD chimeric protein is an amino-terminal gD amino acid sequence, fused to an internal antigenic sequence, fused to a carboxy-terminal amino acid sequence of gD.

In certain embodiments, the first polypeptide segment of a gD chimeric protein of the present invention includes the entire gD amino acid sequence (e.g., amino acids 1-394) or the mature gD amino acid sequence (e.g., amino acids 26-394, the carboxy-terminal 369 amino acids). In other embodiments, the first polypeptide segment includes less than full-length mature gD but includes 250, 260, 270, 280, 290, 300, 305, 310, 315, 320, 325, 330, 335, 340, 345, 350, 351, 352, 353, 354, 355, 356, 357, 358, 359, 360, 361, 362, 363, 362, 365, 366, 367 or 368 amino acids of the mature gD sequence.

In certain aspects, an antigenic amino acid sequence is inserted within a region of a gD that is between amino acids 230 and 300, between amino acids 235 and 295, or between amino acids 240 and 290 of a mature gD amino acid sequence. In other aspects an antigenic amino acid sequence is inserted at a position carboxy-terminal to amino acid 230, 235, 240, 245, 250, 255, 260, 265, 270, 275, 280, 285 of a mature gD amino acid sequence. In certain aspects, an antigenic amino acid sequence is inserted immediately adjacent to amino acid 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 282, 282, 283, 284, 285, 286, 287, 288, 289, 290, 291, 292, 293, 294, 295, 296, 297, 298, 299, or 300 of a mature gD amino acid sequence In certain embodiments, a chimeric gD protein of the invention has a structure that is similar to the structure of the wild-type protein, that is, the chimeric gD protein has the ability to interact with HVEM and, in addition, may have one or more of the following activities: 1) stimulating a $CD8^+$ T cell response to the fusion partner; 2) disrupting an HVEM-BTLA pathway activity; 3) interacting with nectin-1; 4) mediating cell entry by an HSV-1 and/or HSV-2 virus; and/or 5) mediating cell-to-cell spread of HSV-1 and/or HSV-2.

Antigens

As used herein, the term "antigen" (also termed "fusion partner" in relation to gD) is intended to include, but is not limited to, a substance that an immune response is specifically mounted against, such as a protein or a polypeptide. An antigen of the invention can be of any length, ranging in size from a few amino acids in length to hundreds of amino acids in length, provided that that the chimeric gD maintains a structure that is similar to that of the wild-type gD, e.g., the chimeric gD retains one or more activities of the wild-type gD, particularly the activities of interacting with HVEM and/or stimulating a $CD8^+$ T cell response to the fusion partner in the host. In certain aspects of the invention, the antigen is 1000, 900, 800, 700, 600, 500, 400, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 30, 20, 10 or less amino acids in length.

An antigen of the present invention includes a heterologous protein and/or polypeptide, such as a viral, bacterial, fungal, or parasite protein or polypeptide, and/or a host polypeptide and/or protein e.g., a tumor cell polypeptide or protein (such as an oncoprotein or a portion thereof) or a polypeptide or protein associated with inflammation. Antigens of particular interest include, but are not limited to, influenza virus antigens, such as nucleoprotein P (NP; see FIG. 16), matrixprotein (M), and hemagglutinin (HA); *Plasmodium* antigens such as thrombospondin-related anonymous protein (TRAP; see FIG. 17), ring-infected erythrocyte surface antigen (RESA), merozoite surface protein 1 (MSP1), merozoite surface protein 2 (MSP2), merozoite surface protein 3 (MSP3), and glutamate-rich antigen (GLURP); human papilloma virus (HPV) antigens, particularly HPV-16 antigens, such as E5 protein, E6 protein, and E7 protein; and HIV antigens, such as gag, pol, nef, tet, and env.

Viruses include DNA or RNA animal virus. As used herein, RNA viruses include, but are not limited to, virus families such as picornaviridae (e.g., polioviruses), reoviridae (e.g., rotaviruses), togaviridae (e.g., encephalitis viruses, yellow fever virus, rubella virus), orthomyxoviridae (e.g., influenza viruses), paramyxoviridae (e.g., respiratory syncytial virus (RSV), measles virus (MV), mumps virus (MuV), parainfluenza virus (PIV)), rhabdoviridae (e.g., rabies virus (RV)), coronaviridae, bunyaviridae, flaviviridae (e.g., hepatitis C virus (HCV)), filoviridae, arenaviridae, bunyaviridae, and retroviridae (e.g., human T-cell lymphotropic viruses (HTLV), human immunodeficiency viruses (HIV)). As used herein, DNA viruses include, but are not limited to, virus families such as papovaviridae (e.g., papilloma viruses), adenoviridae (e.g., adenovirus), herpesviridae (e.g., herpes simplex viruses, e.g., HSV-1, HSV-2; varicella zoster virus (VZV); Epstein-Barr virus (EBV); cytomegalovirus (CMV); human herpesviruses, e.g., HHV-6 and HHV-7; Kaposi's sarcoma-associated herpesvirus (KSHV) and the like), and poxviridae (e.g., variola viruses). These and other viruses and viral proteins are included in the present invention and are described further in Knipe et al., *Field's Virology,* $4^{th}$ ed., Lippincott Williams & Wilkins, 2001, incorporated herein by reference in its entirety for all purposes.

Bacteria include, but are not limited to, gram positive bacteria, gram negative bacteria, acid-fast bacteria and the like. As used herein, gram positive bacteria include, but are not limited to, Actinomedurae, *Actinomyces israelii, Bacillus anthracis, Bacillus cereus, Clostridium botulinum, Clostridium difficile, Clostridium perfringens, Clostridium tetani, Corynebacterium, Enterococcus faecalis, Listeria monocytogenes, Nocardia, Propionibacterium acnes, Staphylococcus aureus, Staphylococcus epiderm, Streptococcus mutans, Streptococcus pneumoniae* and the like. As used herein, gram negative bacteria include, but are not limited to, *Afipia felis, Bacteroides, Bartonella bacilliformis, Bortadella pertussis, Borrelia burgdorferi, Borrelia recurrentis, Brucella, Calymmatobacterium granulomatis, Campylobacter, Escherichia coli, Francisella tularensis, Gardnerella vaginalis, Haemophilius aegyptius, Haemophilius ducreyi, Haemophilius influenziae, Heliobacter pylori, Legionella pneumophila, Leptospira interrogans, Neisseria meningitidia, Porphyromonas gingivalis, Providencia sturti, Pseudomonas aeruginosa, Salmonella enteridis, Salmonella typhi, Serratia marcescens, Shigella boydii, Streptobacillus moniliformis, Streptococcus pyogenes, Treponema pallidum, Vibrio cholerae, Yersinia enterocolitica, Yersinia pestis* and the like. As used herein, acid-fast bacteria include, but are not limited to, *Myobacterium avium, Myobacterium leprae, Myobacterium tuberculosis* and the like.

Other bacteria not falling into the other three categories include, but are not limited to, *Bartonella henseiae, Chlamydia psittaci, Chlamydia trachomatis, Coxiella burnetii, Mycoplasma pneumoniae, Rickettsia akari, Rickettsia prowazekii, Rickettsia rickettsii, Rickettsia tsutsugamushi, Rickettsia typhi, Ureaplasma urealyticum, Diplococcus pneumoniae, Ehrlichia chafensis, Enterococcus faecium, Meningococci* and the like.

Fungi include, but are not limited to, Aspergilli, Candidae, *Candida albicans, Coccidioides immitis*, Cryptococci, and combinations thereof.

Parasites include, but are not limited to, *Balantidium coli, Cryptosporidium parvum, Cyclospora cayatanensis, Encephalitozoa, Entamoeba histolytica, Enterocytozoon bieneusi, Giardia lamblia, Leishmaniae, Plasmodii, Toxoplasma gondii, Trypanosomae*, trapezoidal amoeba and the like.

Oncoproteins are intended, without limitation, to refer to proteins and/or peptides that are capable of inducing cell transformation. Oncoproteins include, but are not limited to, cellular proteins such as PDGF, ERB-B, ERB-B2, K-RAS, N-RAS, C-MYC, N-MYC, L-MYC, BCL-2, BCL-1, MDM2 and the like. Oncoproteins also include, but are not limited to, viral proteins from RNA and/or DNA tumor viruses such as hepatitis B viruses, SV40 viruses, polyomaviruses, adenoviruses, herpes viruses, retroviruses and the like. Tumor suppressor proteins are intended, without limitation, to refer to proteins or polypeptides that can suppress or block aberrant cellular proliferation, as well as tumor suppressor proteins that have been mutated and, accordingly, no longer suppress or block aberrant cellular proliferation. Tumor suppressor proteins include, but are not limited to, cellular proteins such as APC, DPC4, NF-1, NF-2, MTS1, RB, p53 and the like.

gD chimeric proteins of the present invention are useful for modulating disorders associated with aberrant cellular proliferation mediated by oncoproteins and/or tumor suppressor proteins, such as cancer. Aberrant cellular proliferation is intended to include, but is not limited to, inhibition of proliferation including rapid proliferation. As used herein, the term "disorder associated with aberrant cellular proliferation" includes, but is not limited to, disorders characterized by undesirable or inappropriate proliferation of one or more subset(s) of cells in a multicellular organism. The term "cancer" refers to various types of malignant neoplasms, most of which can invade surrounding tissues, and may metastasize to different sites (*PDR Medical Dictionary* 1st edition (1995)). The terms "neoplasm" and "tumor" refer to an abnormal tissue that grows by cellular proliferation more rapidly than normal and continues to grow after the stimuli that initiated proliferation is removed (*PDR Medical Dictionary* 1st edition (1995)). Such abnormal tissue shows partial or complete lack of structural organization and functional coordination with the normal tissue which may be either benign (benign tumor) or malignant (malignant tumor).

Polypeptides and proteins associated with inflammation include those that modulate a disease or disorder characterized by, caused by, resulting from, or becoming affected by inflammation. Examples of inflammatory diseases or disorders include, but not limited to, acute and chronic inflammation disorders such as asthma, psoriasis, rheumatoid arthritis, osteoarthritis, psoriatic arthritis, inflammatory bowel disease (Crohn's disease, ulcerative colitis), sepsis, vasculitis, and bursitis; autoimmune diseases such as lupus, polymyalgia, rheumatica, scleroderma, Wegener's granulomatosis, temporal arteritis, cryoglobulinemia, and multiple sclerosis; transplant rejection; reperfusion injury in strokes or myocardial infarction; osteoporosis; cancer, including solid tumors (e.g., lung, CNS, colon, kidney, and pancreas); Alzheimer's disease; atherosclerosis; viral (e.g., HIV or influenza) infections; chronic viral (e.g., Epstein-Barr, cytomegalovirus, herpes simplex virus) infection; and ataxia telangiectasia.

Nucleic Acid Molecules

The invention also provides nucleic acid molecules which encode fusion proteins of the invention. In certain embodiments of the invention, the nucleic acid molecule is a vector. As used herein, the term "vector" refers to a nucleic acid molecule, a protein, or a liquid structure capable of transporting another nucleic acid. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors are replication-defective and remain in the nucleus as episomes. Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. The terms "plasmid" and "vector" can be used interchangeably as the plasmid is a commonly used form of vector.

In one embodiment, a recombinant virus is provided for eliciting an immune response in a host infected by the virus. In certain aspects, the recombinant virus is replication-incompetent. A recombinant virus may be constructed from any virus using methods known in the art, provided that the native progenitor is rendered replication incompetent. For example, replication-incompetent adenovirus, adeno-associated virus, SV40 virus, retrovirus, herpes simplex virus or vaccinia virus may be used to generate the recombinant virus by inserting the viral antigen into a region that is non-essential to the infectivity of the recombinant virus. A recombinant virus does not have the pathologic regions of the native progenitor of the benign virus but retains its infectivity to the host.

In a certain embodiment, the recombinant virus is a replication-incompetent chimpanzee-derived adenovirus. Chimpanzee-derived adenovirus vectors have distinct advantages over previously used adenoviral recombinants of the human serotype 5 that is typically used in the art. Most importantly, the efficacy of simian adenoviral vaccine carriers is not impaired by pre-existing neutralizing antibodies to human adenovirus serotype 5 that can be detected in up to 45% of the adult human population in the United States. Furthermore, simian adenoviral recombinants have interactions with cells of the innate immune system, most notably dendritic cells, which sponsor development of strongly biased Th1 responses suited to induce potent responses of $CD8^+$ T cells, a subset of immunocytes that is particularly important to control the spread of HIV-1. For a review of replication-incompetent chimpanzee-derived adenovirus, see U.S. Pat. No. 6,019,978, incorporated herein by reference in its entirety for all purposes.

A number of viral vectors suitable for in vivo expression of the gD chimeric proteins described herein are known. Such vectors include retroviral vectors (see, e.g., Miller (1992) *Curr. Top. Microbiol. Immunol.* 158:1; Salmons and Gunzburg (1993) *Human Gene Therapy* 4:129; Miller et al. (1994) *Meth. Enz.* 217:581) and adeno-associated vectors (reviewed in Carter (1992) *Curr. Opinion Biotech.* 3:533; Muzcyzka (1992) *Curr. Top. Microbiol. Immunol.* 158:97). Other viral vectors that are used include adenoviral vectors, alphavirus replicons, herpes virus vectors, pox virus vectors, and rhabdovirus vectors, as generally described in, e.g., Jolly (1994) *Cancer Gene Therapy* 1:51; Latchman (1994) *Molec. Biotechnol.* 2:179; Johanning et al. (1995) *Nucl. Acids Res.* 23:1495; Berencsi et al. (2001) *J. Infect. Dis.* 183:1171; Rosenwirth et al. (2001) *Vaccine* February 19:1661; Kittlesen et al. (2000) *J. Immunol.* 164:4204; Brown et al. (2000) *Gene Ther.* 7:1680; Kanesa-thasan et al. (2000) *Vaccine* 19:483; and Sten (2000) *Drug* 60:249. Compositions comprising vectors and an acceptable excipient are provided herein.

Nucleic Acid and Protein Variants

In certain aspects, gD nucleic acid molecules and polypeptides are "naturally occurring." As used herein, a "naturally-occurring" molecule refers to a gD molecule having a nucleotide sequence that occurs in nature (e.g., encodes a gD polypeptide sequence found in a herpes simplex virus, e.g., HSV-1 or HSV-2). In addition, naturally or non-naturally occurring variants of these polypeptides and nucleic acid molecules which retain the same functional activity, e.g., the ability to bind HVEM and/or stimulate an immune response to a fusion partner in a host. Such variants can be made, e.g., by mutation using techniques that are known in the art. Alternatively, variants can be chemically synthesized.

As used herein, the term "variant" is intended to include, but is not limited to, nucleic acid molecules or polypeptides that differ in sequence from a reference nucleic acid molecule or polypeptide, but retains its essential properties, that is, it retains the ability to interact with HVEM and, in addition, it may have one or more of the following activities: 1) stimulating a $CD8^+$ T cell response to a fusion partner 2) disrupting an HVEM-BTLA pathway activity; 3) interacting with nectin-1; 4) mediating cell entry by an HSV-1 and/or HSV-2 virus; and/or 5) mediating cell-to-cell spread of HSV-1 and/or HSV-2. Changes in the nucleotide sequence of the variant may or may not alter the amino acid sequence of a polypeptide encoded by the reference nucleic acid molecule. Nucleotide changes may result in amino acid substitutions, additions, deletions, fusions and truncations in the polypeptide encoded by the reference sequence.

Variants can be made using mutagenesis techniques that are known in the art. Alternatively, variants can be chemically synthesized. Mutations can include one or more point mutations, deletions and/or insertions. In certain aspects of the invention, a mutant gD chimeric polypeptide has the ability to bind HVEM at a level that is the same as or greater than the ability of a wild-type gD protein to bind HVEM. In certain aspects of the invention, amino acid W 294 of the mature gD sequence is mutated to alanine.

Construction of Fusion Proteins

Fusion proteins of the invention typically are prepared recombinantly, as described in Example 1. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS). Alternatively, a fusion protein can be synthesized chemically, for example, using solid phase techniques. See, e.g., Merrifield, J. Am. Chem. Soc. 85, 2149 54, 1963; Roberge et al., Science 269, 202 04, 1995. Protein synthesis can be performed using manual techniques or by automation. Automated synthesis can be achieved, for example, using Applied Biosystems 431A Peptide Synthesizer (Perkin Elmer). Optionally, fragments of a fusion protein can be separately synthesized and combined using chemical methods to produce a full-length molecule.

Methods of Using Fusion Proteins and Nucleic Acids of the Invention

Pharmaceutical Compositions

Dosage Regimens

Certain embodiments of the invention are directed to prophylactically treating an individual in need thereof. As used herein, the term "prophylactic treatment" includes, but is not limited to, the administration of a nucleic acid sequence encoding a gD chimeric protein to a subject who does not display signs or symptoms of a disease, pathology, or medical disorder, or displays only early signs or symptoms of a disease, pathology, or disorder, such that treatment is administered for the purpose of diminishing, preventing, or decreasing the risk of developing the disease, pathology, or medical disorder. A prophylactic treatment functions as a preventative treatment against a disease or disorder.

Certain embodiments of the invention are directed to therapeutically treating an individual in need thereof. As used herein, the term "therapeutically" includes, but is not limited to, the administration of a nucleic acid sequence encoding a gD chimeric protein to a subject who displays symptoms or signs of pathology, disease, or disorder, in which treatment is administered to the subject for the purpose of diminishing or eliminating those signs or symptoms of pathology, disease, or disorder.

Embodiments of the present invention are directed to compositions and methods for enhancing the immune response of a subject to one or more antigens. As used herein, the terms "subject" and "host" are intended to include living organisms such as mammals. Examples of subjects or hosts include, but are not limited to, horses, cows, sheep, pigs, goats, dogs, cats, rabbits, guinea pigs, rats, mice, gerbils, non-human primates, humans and the like, non-mammals, including, e.g., non-mammalian vertebrates, such as birds (e.g., chickens or ducks) fish or frogs (e.g., *Xenopus*), and a non-mammalian invertebrates, as well as transgenic species thereof.

As used herein, the term "immune response" is intended to include, but is not limited to, T and/or B cell responses, that is, cellular and/or humoral immune responses. In one embodiment, the claimed methods can be used to stimulate cytotoxic T cell responses. The claimed methods can be used to stimulate both primary and secondary immune responses. The immune response of a subject can be determined by, for example, assaying antibody production, immune cell proliferation, the release of cytokines, the expression of cell surface markers, cytotoxicity, and the like. In certain aspects, the claimed gD chimeric proteins increase the immune response in a subject when compared to the immune response by an untreated subject or a subject who receives a vaccine containing the same antigen but without gD.

As used herein, the term "enhancing an immune response" includes increasing T and/or B cell responses, that is, cellular and/or humoral immune responses, by treatment of a subject using the claimed gD chimeric proteins and/or methods. In one embodiment, the claimed gD chimeric proteins and/or methods can be used to enhance cytotoxic T cell responses to the antigen (fusion partner). In another embodiment, the claimed compounds and methods can be used to inhibit the ability of the HVEM to interact with B and T lymphocyte attenuator (BTLA), thus enhancing an immune response to the antigen (fusion partner). In another embodiment, the claimed gD chimeric protein interacts with HVEM.

As used herein, the term "immune cell" is intended to include, but is not limited to, cells that are of hematopoietic origin and play a role in an immune response. Immune cells include, but are not limited to, lymphocytes, such as B cells and T cells; natural killer cells; myeloid cells, such as monocytes, macrophages, eosinophils, mast cells, basophils, and granulocytes.

As used herein, the term "adjuvant" includes, but is not limited to, agents which potentiate the immune response to an antigen. Adjuvants can be administered in conjunction with a nucleic acid sequence encoding a gD chimeric protein of the invention to additionally augment the immune response.

Nucleic acid sequences encoding the gD chimeric proteins described herein can be administered to subjects in whom it is desirable to promote an immune response. In one embodiment, a nucleic acid sequence encoding a gD chimeric protein described herein is administered prophylactically, e.g., prior to infection with a pathogen or to a subject who is free of cancer or free of an autoimmune disease. In another embodiment, a nucleic acid sequence encoding a gD chimeric protein described herein is administered therapeutically, e.g., to a subjects who has a preexisting condition, e.g., a subject who is infected with a pathogen, who has cancer, or who suffers from an autoimmune disease.

In one embodiment, the gD chimeric protein is administered by "genetic immunization." In this embodiment, a DNA expression vector encoding the gD chimeric protein is injected into the subject animal, e.g., into the skin or into a muscle of the subject. The gene products are correctly synthesized, glycosylated, folded, and expressed by the subject to elicit the desired immune response. In one embodiment, DNA is injected into muscles or delivered into the skin coated onto gold microparticles by a particle bombardment device, a "gene gun." Genetic immunization has been shown to induce specific humoral responses and cellular immune responses (See, e.g., Mor et al. (1995) *J. Immunol.* 155:2039; Xu and Liew (1995) *Immunology* 84:173; Davis et al. (1994) *Vaccine* 12:1503).

A dosage regimen of administration of a gD chimeric protein or a nucleic acid sequence encoding a gD chimeric protein may be adjusted to provide the optimum therapeutic response for each subject without undue experimentation. For example, antibody titers to an antigen or cellular immune responses to an antigen can be measured to determine whether or not the subject is developing an immune response or is manifesting an enhanced immune response to the antigen and the dosage regimen can be adjusted accordingly.

The composition including a gD chimeric protein or a nucleic acid sequence encoding a gD chimeric protein may also be administered parenterally or intraperitoneally. The agent can be administered, for example, intranasally, orally, intravenously, intramuscularly, subcutaneously or mucosally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injection include sterile aqueous solutions (where water soluble) or dispersions and sterile powders for the extemporaneous preparation of sterile injectable solutions or dispersion. A pharmaceutical composition of the invention can be formulated to be suitable for a particular route of administration. For example, in various embodiments, a pharmaceutical composition of the invention can be suitable for injection, inhalation or insufflation (either through the mouth or the nose), or for intranasal, mucosal, oral, buccal, parenteral, rectal, intramuscular, intravenous, intraperitoneal, and subcutaneous delivery.

The composition including a gD chimeric protein or a nucleic acid sequence encoding a gD chimeric protein will be sterile. In addition, it will be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be desirable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile, injectable solutions can be prepared by incorporating a gD chimeric protein or a nucleic acid sequence encoding a gD chimeric protein in the required amount in an appropriate solvent with one or a combination of ingredients enumerated above, as required, followed by filter sterilization. Generally, dispersions are prepared by incorporating the gD chimeric protein or the nucleic acid sequence (with or without a carrier) encoding the gD chimeric protein into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., agent or composition) plus any additional desired ingredient from a previously sterile-filtered solution thereof. The agent or composition can be administered in a form suitable for use with a needle-less injector device (such devices are known in the art (see, e.g., U.S. Pat. Nos. 5,383,851; 5,581,198; 5,846,233) for example as described in *Mol. Med.* (1998) 4:109.

When the composition including a gD chimeric protein or a nucleic acid sequence encoding a gD chimeric protein is suitably protected, as described above, the composition may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the composition including a gD chimeric protein or a nucleic acid sequence encoding a gD chimeric protein, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active agent or composition for the treatment of individuals.

The composition including a gD chimeric protein or a nucleic acid sequence encoding a gD chimeric protein of the invention is administered to subjects in a biologically compatible form suitable for pharmaceutical administration in vivo to enhance immune responses. By "biologically compatible form suitable for administration in vivo" is meant a form of the gD chimeric protein or a nucleic acid sequence encoding a gD chimeric protein to be administered in which any toxic effects are outweighed by the therapeutic effects of the agent.

Administration of a therapeutically or prophylactically active amount of the compositions of a gD chimeric protein or a nucleic acid sequence encoding a gD chimeric protein is defined as an amount effective, at dosages and for periods of time necessary to achieve the desired result. The administration of a gD chimeric protein or a nucleic acid sequence encoding a gD chimeric protein can result in an enhanced immune response (e.g., a stimulation of $CD8^+$ T cells) to an antigen (e.g., a viral or a tumor cell antigen).

As defined herein, a therapeutically or prophylactically effective amount of a composition of a gD chimeric protein or a nucleic acid sequence encoding a gD chimeric protein (an effective dosage) ranges from about 0.001 to 30 mg/kg body weight, about 0.01 to 25 mg/kg body weight, about 0.1 to 20 mg/kg body weight, or from about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an inhibitor can include a single treatment or can include a series of treatments. It will also be appreciated that the effective dosage of inhibitor used for treatment may increase or decrease over the course of a particular treatment. Changes in dosage may result from the results of diagnostic assays as described herein.

The practice of the present invention will employ, unless otherwise indicated, conventional techniques of cell biology, cell culture, molecular biology, microbiology, recombinant DNA and immunology, which are within the skill of the art. Such techniques are explained fully in the literature. See, for example, *Molecular Cloning A Laboratory Manual*, 2nd Ed., ed. by Sambrook, J. et al. (Cold Spring Harbor Laboratory Press (1989)); *Short Protocols in Molecular Biology*, 3rd Ed., ed. by Ausubel, F. et al. (Wiley, NY (1995)); *Current Protocols in Molecular Biology*, John Wiley & Sons, Inc., 1998; DNA Cloning, Volumes I and II (D. N. Glover ed., 1985); Oligonucleotide Synthesis (M. J. Gait ed. (1984)); Mullis et al. U.S. Pat. No. 4,683,195; Nucleic Acid Hybridization (B. D. Hames & S. J. Higgins eds. (1984)); the treatise, Methods In Enzymology (Academic Press, Inc., N.Y.); *Immunochemical Methods in Cell and Molecular Biology* (Mayer and Walker, eds., Academic Press, London (1987)); *Handbook of Experimental Immunology*, Volumes I IV (D. M. Weir and C. C. Blackwell, eds. (1986)); and Miller, J. *Experiments in Molecular Genetics* (Cold Spring Harbor Press, Cold Spring Harbor, N.Y. (1972)).

The following examples are set forth as being representative of the present invention. These examples are not to be construed as limiting the scope of the invention as these and other equivalent embodiments will be apparent in view of the present disclosure, figures, tables, and accompanying claims. The contents of all references, patents and published patent applications cited throughout this application are hereby incorporated by reference in their entirety for all purposes.

Example 1

Materials and Methods
Construction of HSV-1 gD Fused Genes

A number of DNA and adenovirus vector vaccines were constructed and tested (Table 1). The chimeric gene gDE7E6E5 was constructed based on the fusion of the HPV-16 E7, E6 and E5 oncoproteins and the HSV-1 gD protein. Although in this example the HPV proteins are in the order E7, E6, and E5, they can be used in any order. The E7, E6 and E5 genes, without their respective stop codons, were amplified by PCR using the HPV-16 complete genome as a template. The gD gene is from HSV-1. E7, E6, and E5 genes are from HPV-16. Gag is a codon-optimized truncated form of gag from HIV-1 clade B. SgD is a mutated form (W294A) of HSV-1 gD, which shows high affinity to HVEM (Krummenacher et al., 2005). NBEF is a mutated HSV-1 gD, which contains mutations that has been described to prevent gD-HVEM interaction (Connelly et al, 2003); see SEQ ID NO:37. pRE4 was provide by Drs. Gary Cohen and Roselyn Eisenberg (Cohen et al., 1988). AdC68gag was previously described by Fitzgerald and collaborators (2003).

TABLE 1

List of vaccine vectors used.

| Vector name | Genes encoded | Vaccine carrier |
| --- | --- | --- |
| pRE4 (pgD) | gD | DNA vaccine |
| pE7E6E5 | E7, E6, and E5 | DNA vaccine |
| pgDE7E6E5 | gD, E7, E6, and E5 | DNA vaccine |
| pgDE7 | gD and E7 | DNA vaccine |
| pSgDE7 | SgD (gDW294A) and E7 | DNA vaccine |
| pSgDE7E6E5 | SgD, E7, E6, and E5 | DNA vaccine |
| pNBEFgDE7E6E5 | NBEFgD, E7, E6 and E5 | DNA vaccine |
| pgag | gag | DNA vaccine |
| pgDgag | gD and gag | DNA vaccine |
| AdC68gD | gD | E1-deleted adenovirus vector, chimpanzee serotype 68 |
| AdC68E7 | E7 | E1-deleted adenovirus vector, chimpanzee serotype 68 |
| AdC68E7E6E5 | E7, E6, and E5 | E1-deleted adenovirus vector, chimpanzee serotype 68 |
| AdC68gDE7E6E5 | gD, E7, E6, and E5 | E1-deleted adenovirus vector, chimpanzee serotype 68 |
| AdC68gag | gag | E1-deleted adenovirus vector, chimpanzee serotype 68 |
| AdC68gDgag | gD and gag | E1-deleted adenovirus vector, chimpanzee serotype 68 |

Separate amplification reactions were carried out with the following primers: E7FwApaI and E7RvNarI, E6FwNarI and E6RvNotI, and E5FwNotI and E5RvApaI (Table 2). The DNA fragment of the E7 gene was cleaved with ApaI and NotI. The E6 DNA fragment was cleaved with NotI and NarI, and the E5 was cleaved with NarI and ApaI. All DNA fragments were cloned into the ApaI site in the pRE4 vector, provided by Drs. Gary Cohen and Roselyn Eisenberg (University of Pennsylvania, USA) (Cohen et al., 1988). The correct in-frame cloning of E7-, E6- and E5-encoding genes was confirmed after nucleotide sequencing at Wistar Sequencing Facility. Control vectors pE7E6E5 and AdC68E7E6E5 were generated by PCR using pgDE7E6E5 as template and primers E7FwHindIII and E5RvHindIII (Table 2). AdC68gD control vector was generated using pRE4 as template and primers gDFwXbaI and gDRvXbaI (Table 2).

TABLE 2

List of primers used

| Primer | Sequence (5'-3') |
| --- | --- |
| E7FwApaI | GCTGTAGGGCCCCATGGAGATACACCTAC (SEQ ID NO: 1) |
| E7RvNarI | CATGGTGGCGCCTGGTTTCTGAGAACAG (SEQ ID NO: 2) |
| E6FwNarI | AGACATGGCGCCCACCAAAAGAGAACTGC (SEQ ID NO: 3) |
| E6RvNotI | CTCCATGCGGCCGCCCAGCTGGGTTTCTCTACG (SEQ ID NO: 4) |
| E5FwNotI | GACAAAGCGGCCGCCTGCATCCACAACATTAC (SEQ ID NO: 5) |
| E5RvApaI | ACATATGGGCCCTGTAATTAAAAAGCGTGC (SEQ ID NO: 6) |
| E7FwHindIII | GGGTGGAAGCTTATGGGAGATACACCTAC (SEQ ID NO: 7) |
| E5RvHindIII | TGGGGCAAGCTTTTAAATTAAAAAGCGTGC (SEQ ID NO: 8) |
| gDFwXbaI | CCCTAGTCTAGAATGGGGGGGCTGCCGCC (SEQ ID NO: 9) |
| gDRvXbaI | CCCTAGTCTAGACTAGTAAAACAAGGGCTGGTG (SEQ ID NO: 10) |
| gagFwNarI | AAGAAGGGCGCCGGTGCGAGAGCGTCAG (SEQ ID NO: 11) |
| gagRvNarI | AAGGGTGGCGCCCAAAACTCTTGCCTTATGGC (SEQ ID NO: 12) |
| gDFwHindIII | AAGCCCAAGCTTATGGGGGGGCTGCCGCC (SEQ ID NO: 13) |
| gDRvHindIII | AAGCCCAAGCTTCTAGTAAAACAAGGGCTGGTG (SEQ ID NO: 14) |
| NBEFgDrv | GACCGGAAGGTCTTTGCCGCGAAAGCGAGCGGGGTCGGCCGCCTTGAG (SEQ ID NO: 15) |
| NBEFgDFw | CGCTTTCGCGGCAAAGACCTTCCGGTCGCGGACGCGGCGGCCGCCCC (SEQ ID NO: 16) |
| SgDFw | CAAATCCAACAAAACGCGCACATAGGCTCGATCC (SEQ ID NO: 17) |
| SgDRv | GATCGACGGTATGTGCGCGTTTGGTGGGATTTGC (SEQ ID NO: 18) |

To construct the AdC68gDE7E6E5 vector, the gDE7E6E5 chimeric gene was amplified by PCR using the pgDE7E6E5 vector as a template. The PCR reaction was carried out with gDFwXbaI and gDRvXbaI primers (Table 2). The DNA fragment of the gDE7E6E5 chimeric gene was cleaved with XbaI and cloned into XbaI site on the shuttle vector (BD PharMingen, San Diego, Calif.). The pShuttlegDE7E6E5 clone was confirmed by restriction analysis and sub-cloned into E1-deleted chimpanzee-derived adenovirus vector serotype 68 using PI-SceI and I-CeuI sites as described (Fitzgerald et al. 2003).

The gDgag chimeric gene was generated by insertion of the codon-optimized truncated form of gag from HIV-1 clade B into the HSV-1 gD NarI site. The gag gene was amplified by PCR using the pCMVgag vector as a template and primers gagFwNarI and gagRvNarI (Table 2). The DNA fragment corresponding to gag gene was cleaved with NarI, cloned into pShuttlegD, and then sub-cloned into AdC68 vector as described above.

Construction of gD Mutants

The SgDE7 mutated gene was constructed using QUICK-CHANGE® site-directed mutagenesis kit (Stratagene Cloning Systems, La Jolla, Calif.) as recommended by the manufacturer. Briefly, SgDFw and SgDRv primers (Table 2), designed to mutate the amino acid residue 294 of gD, were used to PCR amplify the entire pgDE7 vector. The reaction products were then treated with DpnI and used to transform DH5α E. coli cells. The NBEFgDE7E6E5 gene (see SEQ ID NO:37) was generated by mutation of residues crucial for HVEM-gD interaction. HSV-1 gD residues 11, 15, 25, 27, 28, 29, and 30, were mutated to alanine by gene splicing by overlap extension (i.e., gene SOEing). Briefly, two PCR reactions were carried out using set of primers, (i) with gDFwHindIII and NBEFgDRv, and (ii) with NBEFgDFw and gDRvHindIII (Table 2). Vector pgDE7E6E5 was used as a template in both PCR reactions. Two amplified fragments were used as template to PCR reaction with gDfWHindIII and gDRvHindIII primers (Table 2). The NBEFgDE7E6E5 DNA fragment was cloned into the same pgDE7E6E5 backbone vector. Both mutant gD sequences were confirmed by sequencing the entire gene at Wistar Sequencing Facility.

DNA Vaccine and E1-Deleted Chimpanzee-Derived Adenovirus Purification

DNA vaccines were propagated in E. coli K12 DH5α cells in LB medium supplemented with ampicillin and purified with the Maxi Prep Kit (QIAGEN®, Valencia, Calif.). The DNA concentration was determined by spectrophotometry at 260 nm and confirmed by visual inspection of ethidium bromide-stained 1% agarose gels in comparison to DNA fragments of known concentration (Invitrogen, Carlsbad, Calif.). Plasmids were kept at −20° C. until use, at which time the DNA concentration was adjusted to 1 µg/µl in phosphate-buffered saline (PBS). AdC68 vectors were propagated using E1-transfected HEK 293 cells and purified by CsCl gradient centrifugation as previously described (Fitzgerald et al., 2003). Upon purification, the concentration of each virus vector batch was determined by measuring virus particles (vp) by spectrophotometry at 260 nm.

Cell Lines

TC-1 tumor cells, derived from C57BL/6 origin lung epithelial cells transformed with v-Ha-ras and HPV-16 E6 and E7 genes, were provided by Dr. T. C. Wu, Johns Hopkins University, USA (Lin et al., 1996). Mouse melanoma cells B78H1 and B78H1/3E5, which express HVEM fused to EGFP, were provided by Drs. Gary Cohen and Roselyn Eisenberg (University of Pennsylvania, USA). E1-transfected HEK 293 cells were used to propagate E1-deleted chimpanzee derived adenovirus vectors. All cells were propagated in DMEM supplemented with glutamine, sodium pyruvate, nonessential amino acids, HEPES buffer, antibiotic, and 10% FBS (TC-1, CHO/CAR and E1-transfected HEK 293 cells) or 5% FBS (B78H1 and B78H1/3E5 cells). CHO cells stably transfected to express the coxsackie adenovirus receptor (CHO/CAR) were obtained from J. Bergelson (Childrens Hospital of Philadelphia).

Animals and Immunization

Female BALB/c and C57Bl/6 mice at 6-8 weeks of age were purchased from Jackson Laboratory (Bar Harbor, Me.) or Charles River Laboratories (Boston, Mass.) and housed at the Animal Facility of the Wistar Institute. All procedures involving handling and sacrifice of animals were performed according to approved protocols in accordance with recommendations for the proper use and care of laboratory animals at the Wistar Institute. Groups of 5 to 10 BALB/c and C57Bl/6 mice were intramuscularly (i.m.) vaccinated with the DNA vaccines or E1-deleted chimpanzee derived adenovirus vectors into the tibialis anterior muscle of each hind limb. DNA vaccine was given at 100 µg divided in two 50 µl aliquots. E1-deleted chimpanzee-derived adenovirus vectors (AdC68) were inoculated from $1 \times 10^8$ to at $5 \times 10^{10}$ vp per mouse. For most experiments AdC68 vectors were inoculated at $10^{10}$ viral particles per mouse.

E7 Transgenic Mouse

The E7 transgenic mouse was based on a similar mouse where E7 is expressed in the thymus under the control of the thyroglobulin promoter (Ledent et al., *Oncogene* 1995; 10:1789-97). The plasmid used to create the E7 mouse was a very generous gift from Dr. Catherine Ledent, Université Libre de Bruxelles. The plasmid, constructed in the pSG5 vector, contained the bovine thyroglobulin promoter, a rabbit β-intron, the E7 gene, and a polyadenylation signal in a gene cassette. The bovine thyroglobulin promoter was used as it has been shown to be tightly regulated and expressed in thyrocytes (Ledent et al., *Proc Natl Acad Sci USA* 87:6176, 1990). The rabbit β-intron was used to increase the expression of the transgenes (Palmiter et al., *Proc Natl Acad Sci USA* 88:478, 1991). This cassette was removed and purified by gel electrophoresis followed by a Geneclean kit (Q-Biogen, Morgan Irvine, Calif.). DNA was concentrated by ethanol precipitation. The cut DNA was then microinjected by the University of Pennsylvania School of Medicine Transgenic Facility under the direction of Dr. Jean Richa. The founder mouse strain was C57BL/6. The founder mice were thus mated to wild type C57BL/6, and the progeny back crossed and screened by the ACT real time PCR method for homozygosity. The E7 tg mice were bred at the Animal Facility of the Wistar Institute from a pair provided by Dr. Y. Patterson (University of Pennsylvania). All animal procedures were performed in accordance with recommendations for the proper use and care of laboratory animals at the Wistar Institute. Groups of 3 to 10 animals were vaccinated i.m. with the E1-deleted AdC68 vectors into the tibialis anterior muscle of each hind limb. AdC68 vectors were inoculated at $5 \times 10^{10}$ vp per mouse unless stated otherwise.

Intracellular Cytokine Staining

Intracellular IFN-γ staining was performed using peripheral blood mononuclear cells (PBMC) and cells from the spleen two weeks after the DNA vaccine dose or 10 days after E1-deleted chimpanzee-derived adenoviral vector administration unless stated otherwise. Samples were washed twice with L-15 medium. Cells were then treated for 5 minutes on ice with ACK lysis buffer (Invitrogen) to rupture red blood cells, washed, and suspended in DMEM supplement with 2% FBS. Samples were cultured at a concentration of $10^6$ cells/well for 5 hours at 37° C. in a 96-well round bottom microtiter plate (Costar) in 200 µl of DMEM supplemented with 2% FBS and $10^{-6}$ M 2-mercaptoethanol. Brefeldin A (GolgiPlug; BD PharMingen) was added at 1 µl/ml. The E7-specific RAHYNIVTF (SEQ ID NO:19) peptide, which carries the immunodominant epitope of E7 for mice of the H-2b haplotype, or the AMQMLKETI (SEQ ID NO:20) peptide, which carries the immunodominant MHC class I epitope of gag for mice of the H-2d haplotype, were used for peptide stimulation at a concentration of 3 µg/ml. The V3 control peptide delineated from the sequence of the envelope protein of HIV-1 clade B (VVEDEGCTNLSGF; SEQ ID NO:21) and the SIINFEKL peptide (SEQ ID NO:30) were used as control peptides. After washing, cells were incubated for 30 min at 4° C. with 100 µl of a 1:100 dilution of a fluorescein (FITC)-conjugated monoclonal antibody to mouse CD8a (BD PharMingen). Cells were washed once with PBS followed by permeabilization with Cytofix/Cytoperm (BD PharMingen) for 20 min at 4° C., washed twice with Perm/Wash buffer (BD PharMingen) and incubated in the same buffer for 30 min at 4° C. with 50 µl of a 1:100 dilution of a phycoerythrin (PE)-labeled monoclonal antibody to mouse IFN-γ (BD PharMingen). After washing, cells were suspended in PBS and examined by two-color flow cytometry using an EPICS Elite XL (Beckman Coulter). Data were analyzed by WinMDi software. The percentages of antigen specific $CD8^+$ T cells that stained positive for IFN-γ over all $CD8^+$ T cells were determined.

TC-1 Challenge

C57Bl/6 Mice were challenged subcutaneously (s.c.) with $1 \times 10^5$ TC-1 cells suspended in 100 µl of serum-free media, and injected at one rear flank. To determine the protection of pre-challenge vaccination mice were challenged 10 and 14 days after vaccination with DNA vaccine or E1-deleted chimpanzee derived adenovirus vector, respectively. Post-challenge vaccination was evaluated with mice challenged five days before vaccination (Example 3 and 15). Tumor growth in pre- and post-challenge vaccinated mice was monitored by visual inspection and palpation three times a week. Animals were scored as tumor-bearing when tumors attained sizes of approximately 1-2 mm in diameter. Mice were euthanized once tumors exceeded a diameter of 1 cm. Tumor growth was followed for a period of 60 days after the challenge.

Statistical Analysis

Experiments were conducted using 3-10 mice per group. Samples tested by ELISA were assayed in triplicates. Results show the means±standard deviation (SD). Intracellular cytokine staining was conducted with PBMC from individual mice, while tetramer and markers staining were performed with pooled samples. Significances between two groups were analyzed by one-tailed student's t-test.

HVEM Binding Assay

CHO/CAR cells were infected with either AdC68gD, AdC68gag, or AdC68gDgag. After 72 hrs, cells were harvested, suspend in 1 ml of extraction buffer (10 mM Tris, 150 mM NaCl, 10 mM EDTA, 1% NP-40, 0.5% sodium deoxycholate, 1 mM PMSF [pH 8.0]) supplement with Complete Protease inhibitor (Roche, Basel, Switzerland), and incubated at 4° C. for 1 hour. After spinning at 12,000 g for 15 min at 4° C., protein extracts were kept at −80° C. until use. A capture enzyme-linked immunosorbent assay (ELISA) was used to normalize the amount of gD in the extracts. ELISA plates were coated with 50 µl of a 10 µg/ml concentration of ID3 monoclonal antibody (MAb) diluted in PBS/well. After an overnight incubation at 4° C., plates were exposed to blocking solution for 1 hour and then to extracts diluted in blocking solution for 2 hours at room temperature. Captured gD was detected by adding 50 µl of a 1 µg/ml concentration of Pab R7/well followed by goat anti-rabbit antibody coupled to horseradish peroxidase. Plates were rinsed with 20 mM citrate buffer (pH 4.5), ABTS peroxidase substrate was added, and the absorbance at 405 nm was recorded by using a microtiter plate reader. The level of gD in each extract was normalized by dilution in extraction buffer. To assess receptor binding of the gD mutants, ELISA plates were coated overnight with 50 µl of human-HVEM (5 µg/ml), exposed to blocking solution, and incubated with normalized cell extracts diluted in blocking solution for 2 hours at room temperature. Bound gD was detected as described above. soluble gD306 (Nicola et al., *J. Virol.* 71, 2940-46, 1997; Sisk et al., *J. Virol.* 68, 766-75, 1994) and gD285 (Whitbeck et al., *J. Virol.* 71, 6083-93, 1997), purified as described previously, were used at 1 µM.

Detection of Transcripts by Real-Time PCR

Total RNA was isolated from CHO/CAR cells 48 hrs after infection with the Ultraspec RNA solution system kit (Biotex). The mRNA was reversed transcribed in vitro using MEGAscript transcription kit (Ambion). Remaining DNA was removed by treatment with DNase I (Ambion) for 1 h at 37° C. Quantification of the housekeeping gene glyceraldehyde-3-phosphate dehydrogenase (GAPDH) was performed to normalize the amount of cDNA in each sample. Normalized cDNA samples were used for amplification with E5-, E6-, E7- and gD-specific primers. Quantitative real-time PCR reactions were conducted using the LightCycler-RNA amplification kit SYBR Green 1 (Boehinger Mannheim), following manufacture's conditions. Samples were quantified in triplicate by three independent experiments.

Confocal Microscopy and FACS Analysis

B78H1/3E5 cells, which express HVEM fused to Enhanced Green Fluorescence Protein (HVEM-EGFP), or B78H1 cells (both obtained from Drs. Gary Cohen and Roselyn Eisenberg, University of Pennsylvania) were infected with either AdC68gD, AdC68gag, or AdC68gDgag. CHO/CAR cells were infected with AdC68gD, AdC68E7E6E5, or AdC68gD-E7E6E5. After 48 hours, cells were directly stained or permeabilized with Cytofix/Cytoperm (BD PharMingen) and then stained with anti-gD MAb (DL-6) followed by anti-mouse IgG conjugated with Texas Red or PE. Confocal microscopy was performed with a Leica TCS SP2 Confocal Microscope at 400× final magnification. Cell suspensions were analyzed using an EPICS XL (Beckman-Coulter, Inc., Miami, Fla.) to determine presence of gDgag. Data were analyzed by Flowjo software (Tree Star, Inc.).

Molecular Modeling of gD-Gag

The 3-dimensional models of the gD-gag were constructed with the MODELLER package[44,45] by combining the structures of individual protein domains as determined by X-ray crystallography. The receptor bound form of gD-gag model was based upon the HSV-1 gD HVEM complex (1JMA)[12], chain A, residues 1:259; SIV gag (1ECW)[46], residues 1:119; and HIV-1 gag (1E6J)[47], chain P, residues 11:220. The gD-gag unligated form was based upon the Cyclophilin A/HIV-1Chimera Complex (1M9D)[48], chain A, residues 1:15; HSV-1 gD (2C36)[15], chain A, residues 23:256; SIV gag (1ECW), residues 1:119; and HIV-1 gag (1E6J), chain P, residues 11:220. Ribbon representations were prepared within the Swiss-PdbViewer program[49] and rendered with the Persistence of Vision Ray Tracer program (POV-Ray 2004, version 3.6).

In Vitro T Cell Proliferation Assay

Cells were harvested from draining popliteal lymph node of naïve and mice i.m. immunized 24 hrs earlier with $10^{11}$vps of AdC68gD or AdC68E7E6E5 then irradiated with 2000 RADs. CD8+ cells were isolated from the spleens of OT-1 mice by negative selection using magnetic beads (Miltenyi Biotec) and labeled with 2 µM CFSE (Molecular Probes). A total of 1×10⁶ irradiated lymph node cells were cultured with 1×10⁵ CD8+ CF SE-labeled OT-1 cells in presence of either SIINFEKL peptide or control peptide AMQMLKETI (both at $10^{-8}$M, Alpha Diagnostic International) in 96-well plate wells for 72 hours. Cells were stained with anti-CD8-PerCP and anti-Vα2-PE (both BD Pharmingen) for 30 min on ice. Cells were examined on aFACSCalibur using CellQuest software (BD Biosciences Pharmingen) and were analyzed using FlowJo software version 7.1.2 (TriStar, Inc).

ELISA for Antibodies to Gag

Sera from the vaccinated or naïve mice were tested on plates coated with purified gag protein. Briefly, 96-well round-bottom Maxisorb (Nunc) plate wells were coated overnight with 0.2 µg of gag p24 HIV-1 (Immuno Diagnostics, Inc.) diluted in 100 µl of coating buffer (15 mM $Na_2CO_3$, 35 mM $NaHCO_3$ and 3 mM $NaN_3$, pH 9.6). The next day plates were blocked with 200 µl of PBS containing 3% BSA for 2 hours. Serum samples were serially diluted in PBS supplemented with 3% BSA and in triplicates at 100 µl/well on the gag-coated plates for 1 h at room temperature. Plates were washed, and a 1:200 dilution of alkaline phosphatase-conjugated goat anti-mouse Igs (Cappel) was added to each well for 1 h at room temperature. After washing, plates were incubated with substrate (10 mg d-nitrophenyl phosphate disodium dissolved in 10 ml of 1 mM $MgCl_2$, 3 mM $NaN_3$, and 0.9 M diethanolamine, pH 9.8), and then read in an automated ELISA reader at 405 nm (model EL311, Bio-Tek Instruments).

Isolation of Lymphocytes

Peripheral blood mononuclear cells (PBMC), spleen and livers were harvested as described (Lasaro et al., Microbes Infect 2005; 7:1541-50; Lin et al., Cancer Res 1996; 56:21-6). Tumor-infiltrating lymphocytes (TILs) were isolated from matrigel-tumors 3 or 10 days after challenge as described (22). TILs from the thyroid of E7-tg mice were harvested upon treatment of thyroid tissue fragments with 2 mg/ml collagenase P (Roche) and 1 mg/ml DNase I (Invitrogen). After 1 hour, the thyroid was homogenized and filtrated through a 70-mm cell strainer. Cells were washed with RPMI (Cellgro) media supplemented with 5% FBS, treated for 5 min on ice with Ack lysing buffer (Invitrogen) to rupture red blood cells, then suspended in 7 mL 40% percoll (Amersham Bioscience, Piscataway, N.J.), and applied on top of 3 mL 70% percoll. After centrifugation at 2200 rpm for 20 min at room temperature, the cells at the interface were harvested and resuspended in media.

Tetramer and Lymphocyte Markers Staining

Antigen-specific CD8+ T cells were detected by APC-labeled MHC class I tetramers carrying the AMQMLKETI peptide (SEQ ID NO:20) of gag or the RAHYNIVTF peptide of E7 (E7tet; SEQ ID NO:19) (MHC Tetramer Core Facility, Emory University Vaccine Center, Atlanta, Ga.). PBMC and splenocytes isolated 10 days after immunization with AdC68 vectors were treated as described for intracellular cytokine staining. Samples were stained for 30 minutes at room temperature with gag-tet and anti-CD8a-PerCP in combination with the following antibodies: CD25-PE, CD122-PE, CD127-PE, CD27-PE, BTLA-PE (eBioscience), PD1-PE, CD62L-FITC, CD69-FITC, CD103-FITC, CD43-FITC, CD44-FITC and CD54-FITC (all from BD Biosciences Pharmingen, unless indicated otherwise). For Bcl2 and CTLA-4 staining, cells were washed, permeabilized for 30 min at 4° C. with Cytofix/Cytoperm (BD Biosciences Pharmingen), and then stained with antibodies Bcl2-PE or CTLA-PE (BD Biosciences Pharmingen).

Lymphocytes were stained for 30 minutes at room temperature with E7-tet and anti-CD8a-PerCP together with the following antibodies: BTLA-PE (eBioscience), CD44-FITC, CD62L-PE, CD27-PE, CD127-PE, CD122-PE and PD1-PE (BD Biosciences Pharmingen). For Bcl2 and CTLA-4 staining, cells were washed, permeabilized for 30 min at 4° C. with Cytofix/Cytoperm (BD Biosciences Pharmingen), and then stained with antibodies Bcl2-PE or CTLA-PE (BD Biosciences Pharmingen). Flow cytometry analyses were performed with at least 100,000 viable cells live-gated on FACSCalibur using CellQuest software (BD Biosciences Pharmingen) and were analyzed using FlowJo software version 7.1.2 (TriStar, Inc).

Example 2

Fusion Protein Constructs

Figure 2:
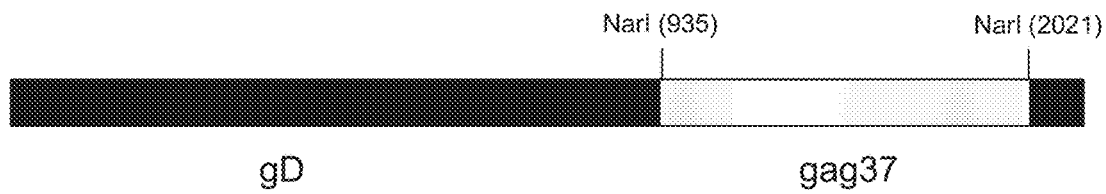
FIG. 2 depicts a schematic representation of chimeric gene gDgag. The codon-optimized truncated form of gag from HIV-1 clade B was fused into the HSV-1 gD gene NarI site, which corresponds to amino acid 289 in the gD mature form.

The HPV-16/HSV-1 glycoprotein D (gD) chimeric gene, called gDE7E6E5, was composed of the complete open reading frame of gD, which had incorporated into the ApaI site a fusion gene composed of HPV-16 E5, E6 and E7 genes without respective start and stop codons (FIG. 1). The HIV-1/gD chimeric gene, named gDgag, was composed of the complete open reading frame of gD which had incorporated into the Nan site a codon-optimized truncated form of gag HIV-1 clade B (FIG. 2).

Example 3

Effects of Fusion Protein Constructs on Host Immune System

Mice were immunized with 100 μg/mouse of DNA vaccines or $5\times10^{10}$ virus particles/mouse of E1-deleted adenovirus vectors. After 14 days (DNA vaccines) or 10 days (E1-deleted adenovirus vaccines) peripheral blood mononuclear cells (PBMC) were stained for CD8 and IFN-γ by intracellular cytokine staining. Percentage represents number of $CD8^+$/IFN-$\gamma^+$ cells over total number of $CD8^+$ cells.

Pre-challenge vaccination: ten days after immunization mice were challenged with $5\times10^5$ TC-1 cells (10 mice per group), in vitro transformed syngeneic cells which express E7 and E6 and induce tumors in C57Bl/6 mice, and tumor growth was following per 60 days. Percentage represents number of tumor-free mice over total mice challenged at day 60.

Post-challenge vaccination: Mice (10 per group) were vaccinated 5 days after challenged with $5\times10^5$ TC-1 cells. Tumor growth was followed for 60 days.

The results are shown in Table 3. Percentage represents number of tumor-free mice over total mice challenged at day 60. The fusion gene gDE7E6E5 expressed by a DNA vaccine (pgDE7E6E5) or an E1-deleted chimpanzee-derived adenovirus vector (AdC68gDE7E6E5) induced high frequencies of E7-specific $CD8^+$ T cells and complete protection against tumor cell challenge after a single dose. However, neither E7-specific $CD8^+$ T cell responses nor protection to challenge were developed when gD was not present, indicating that this fusion had dramatically improved the efficacy of the vaccines.

TABLE 3

| Immunization | E7-specific $CD8^+$ T cell response [b] | Protection upon pre-challenge vaccination [c] | Protection upon post-challenge vaccination [d] |
|---|---|---|---|
| pRE4 (gD only) | 0.11% | 0% | 0% |
| pE7E6E5 | 0.18% | 0% | 0% |
| pgDE7E6E5 | 5.53% | 100% | 70% |
| AdC68gD | 0.05% | 0% | 0% |
| AdC68E7E6E5 | 0.05% | 0% | 0% |
| AdC68gDE7E6E5 | 21.94% | 100% | 100% |

Figure 3A:
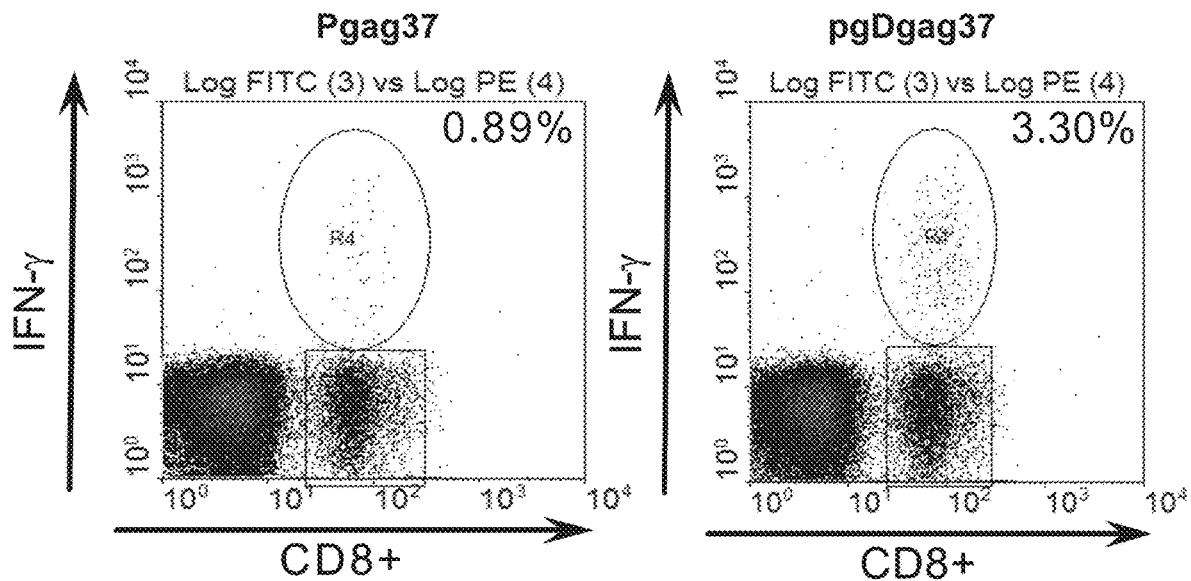
FIGS. 3A-3B depict the gag-specific $CD8^+$ IFN-$\gamma$ response in mice immunized with vaccine constructs carrying the gDgag chimeric gene.
Figure 3B:
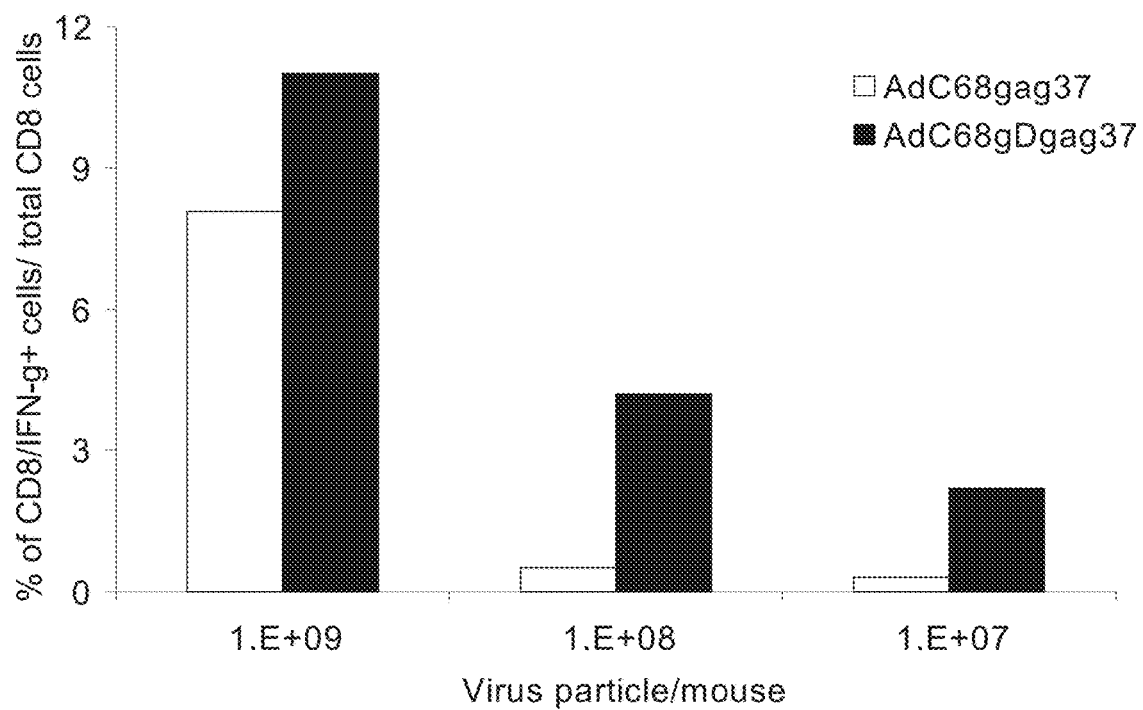

An E1-deleted chimpanzee-derived adenovirus carrying a codon-optimized, truncated form of gag HIV-1 clade B (AdC68gag) has been shown to induce a strong specific $CD8^+$ T cell response (Fitzgerald et al. (2003) *J. Immunol.* 170:1416). However, gag-specific $CD8^+$ T cell frequencies induced by the DNA vaccine (pgDgag) and the E1-deleted chimpanzee-derived adenovirus vector (AdC68gDgag) were higher when gag was fused into gD (FIGS. 3A-3B). The effect of gD fusion was more remarkable when lower amounts of adenovirus vector were used for vaccination (FIG. 3B).

Figure 4:
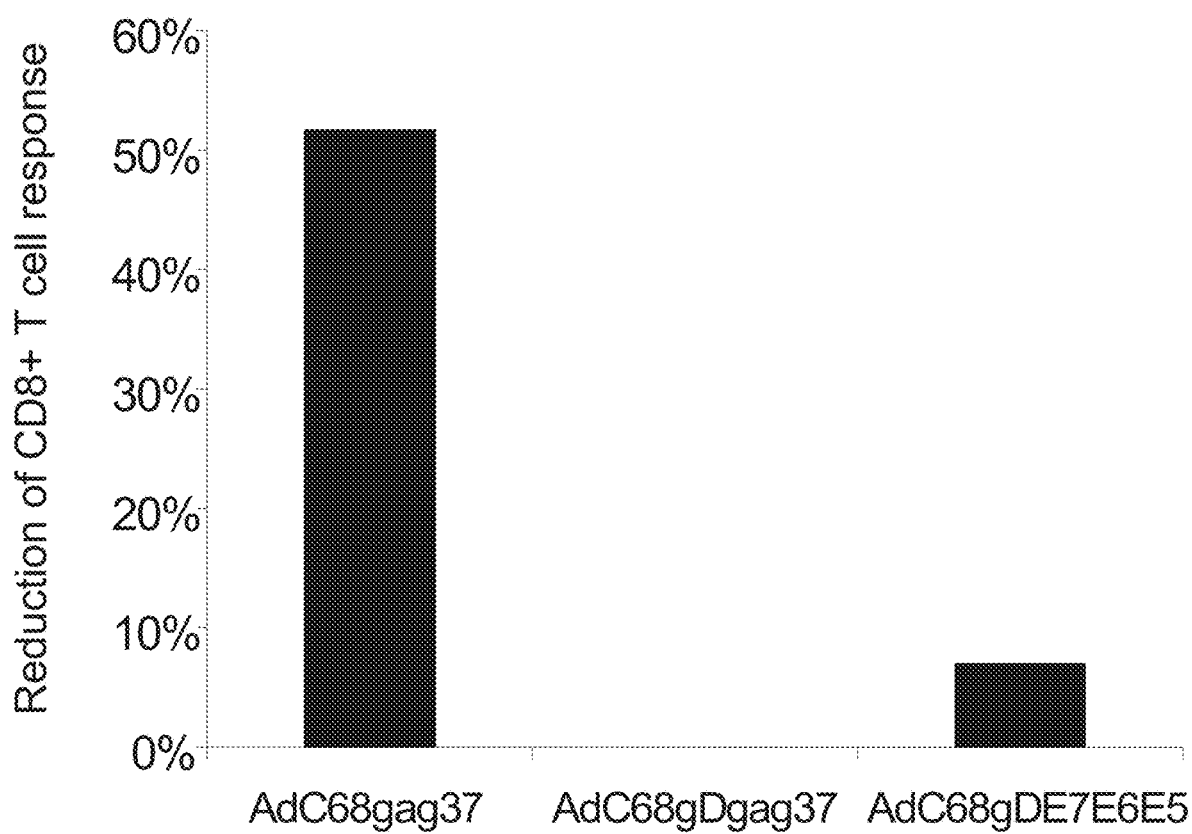
FIG. 4 graphically depicts the effect of pre-existing immunity to the AdHu5 adenovirus vector on the transgene product-specific $CD8^+$ T cell response to the AdC68 vector. AdC68 vectors carrying gag, gDgag or gDE7E65 were inoculated into naïve mice and mice previously immunized with an AdHu5 expressing an unrelated antigen (rabies glycoprotein, AdHu5rab.gp). The percentage of reduction of $CD8^+$ T cell response was defined as a percentage of $CD8^+$/IFN-$\gamma^+$ frequency in mice previously immunized with AdHu5 over the frequency found in mice that did not receive AdHu5 vector.
Figure 5:
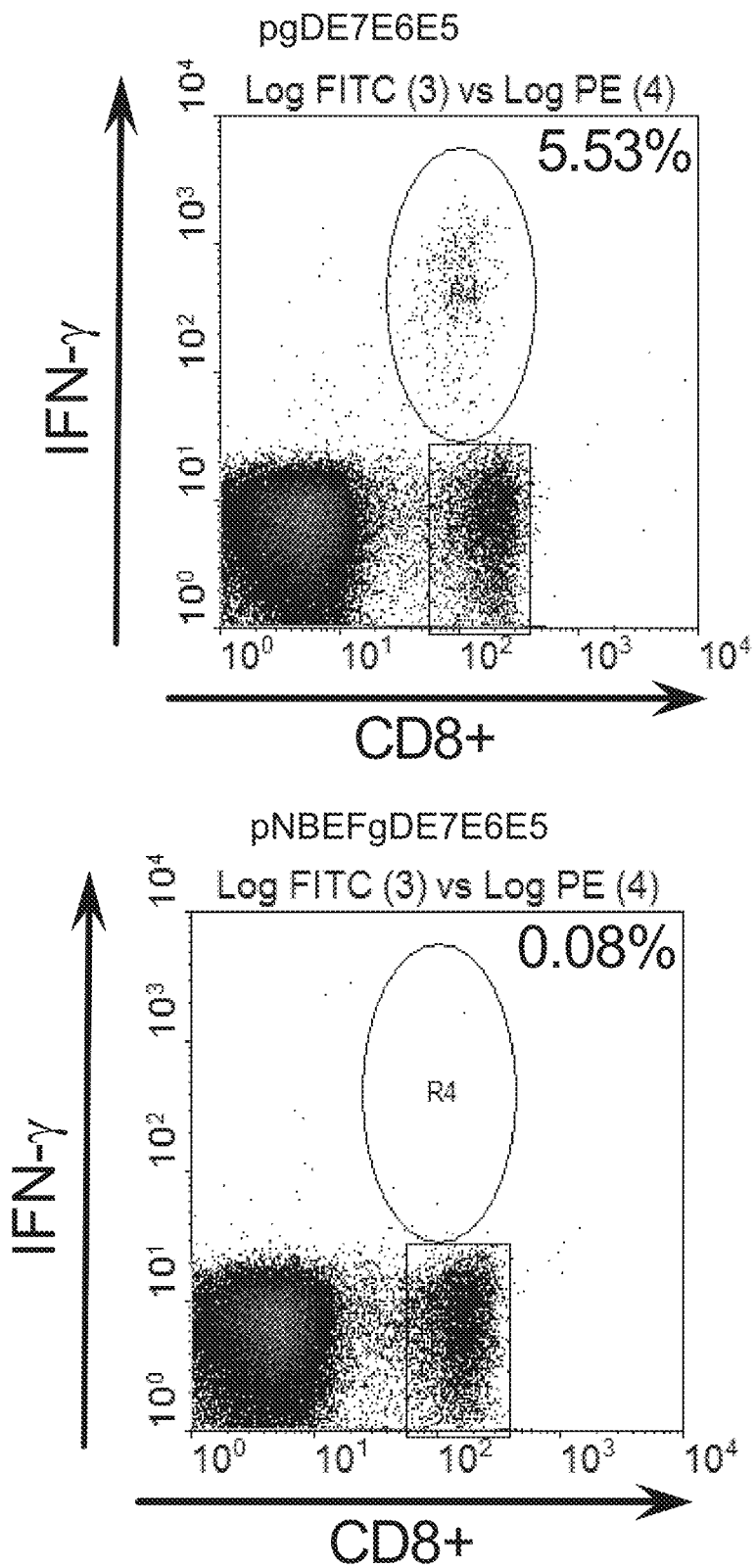
FIG. 5 depicts the E7-specific $CD8^+$ IFN-$\gamma$ response in mice immunized with DNA vaccines expressing non-mutated or mutated gDE7E6E5. The mutation was designed to disrupt the HVEM binding site of gD. Mice were immunized with non-mutated gDE7E6E5 (pgDE7E6E5) or mutated gDE7E6E5 (pNBEFgDE7E6E5) and 14 days later peripheral blood mononuclear cells were investigated by intracellular cytokine staining for E7-specific $CD8^+$ IFN-$\gamma$ responses. Numbers on the right corners represent percentage $CD8^+$/IFN-$\gamma^+$ cells over total of $CD8^+$ cells.
Figure 7:
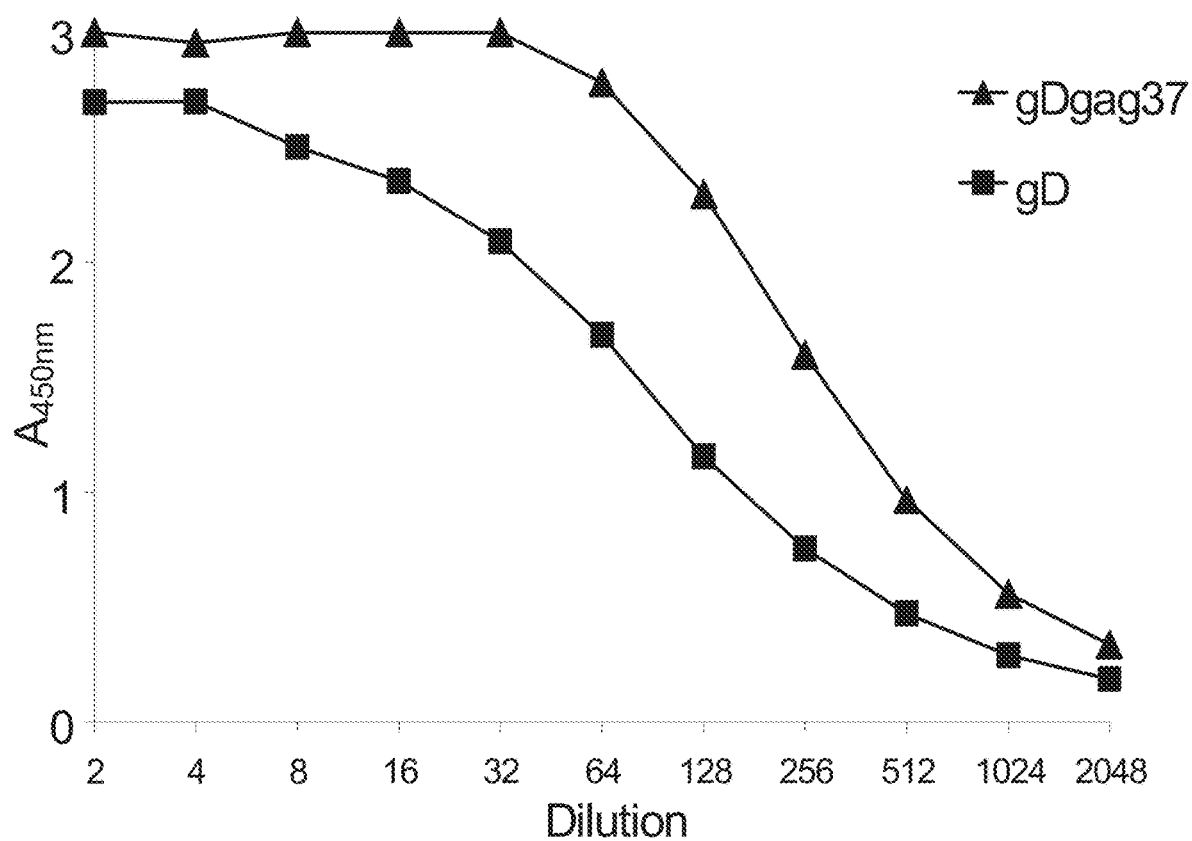
FIG. 7 graphically depicts an in vitro HVEM binding assay. CHO-CAR cells (Chinese hamster ovary-coxsackie-adenovirus receptor cells) were infected with either AdC68gD or AdC68gDgag and, after 48 hours, total protein was extracted. The amount of gD in each sample was quantified by capture ELISA and the protein extracts were diluted in extraction buffer to normalized levels of gD. Equalized extracts were diluted and added to 96-well plates coated with purified HVEM. The amount of gD bound to HVEM was detected by using anti-gD polyclonal antisera and anti-Rabbit IgG horseradish peroxidase. Data shown is one representative experiment from two performed.
Figure 8A:
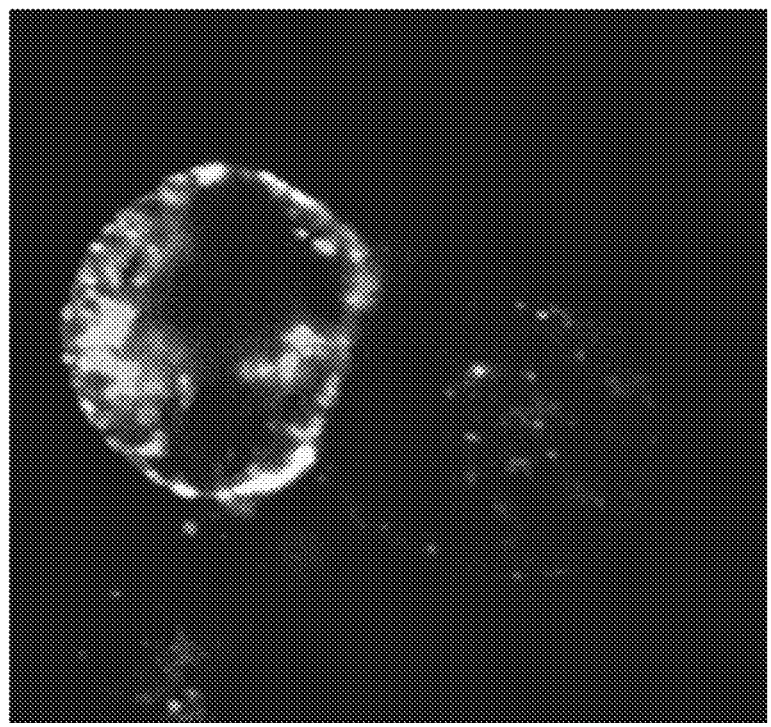
FIGS. 8A-8B depict confocal microscopy for localization of gDgag and HVEM on AdC68gDgag infected cells. B78H1/3E5 cells, which expressed HVEM fused to enhanced green fluorescence protein (HVEM-EGFP), were infected with AdC68gDgag. After 48 hours, cells were either directly stained (FIG. 8A) or permeabilized and stained (FIG. 8B) with an anti-gD monoclonal antibody (DL-6) and anti-mouse IgG conjugated with Texas Red. Cells were examined with a Leica TCS SP2 Confocal Microscope at 400× final magnification.
Figure 8B:
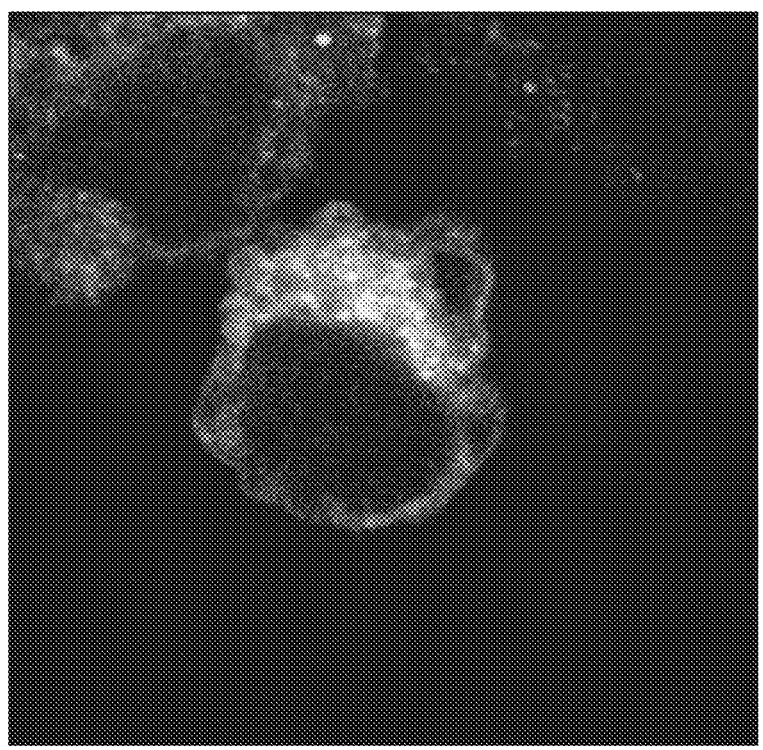
Figure 9:
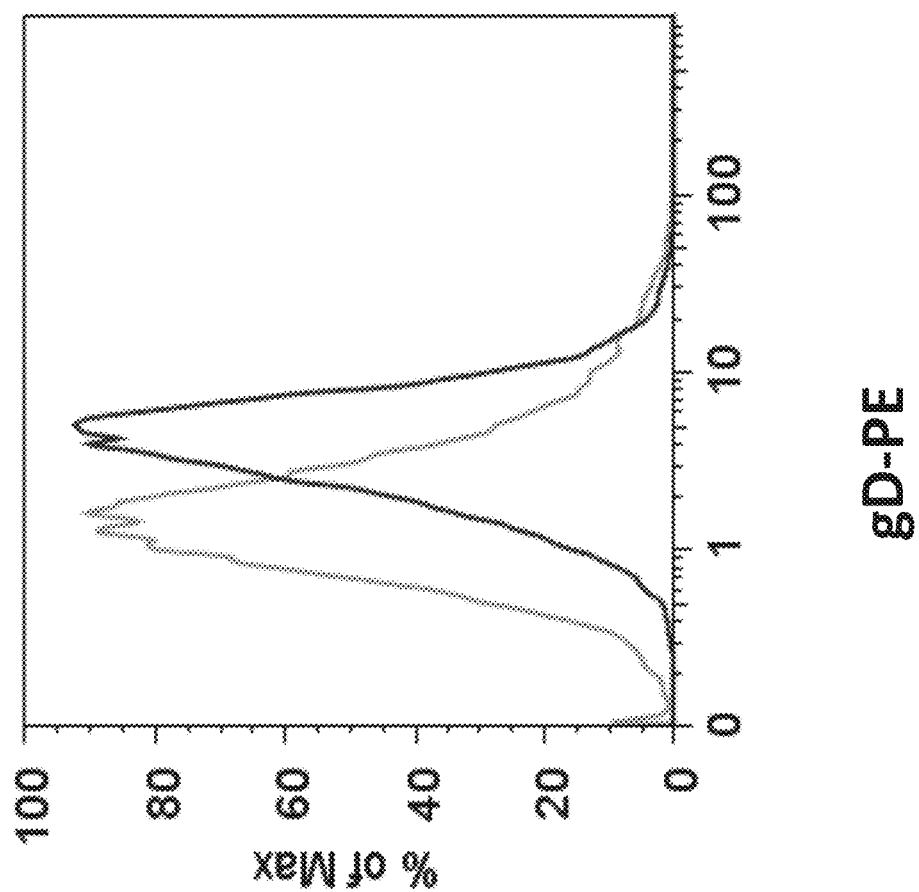
FIG. 9 graphically depicts FACS analysis of gDgag expression on the surface of AdC68gDgag infected cells. B78H1/3E5 cells (darker line), which express HVEM-EGFP on the surface, and B78H1 cells (lighter line), which do not express HVEM, were infected with AdC68gDgag. Cells were cultivated for 48 hours, and then labeled with an anti-gD monoclonal antibody (DL-6) and anti-mouse IgG conjugated to phycoerythrin (PE). Cell suspensions were analyzed using an EPICS XL (Beckman-Coulter, Inc., Miami, Fla.) to determine presence of gDgag.

Although chimpanzee-derived adenovirus vectors circumvented the expected negative effect of pre-existing immunity to common human serotypes of adenovirus, such as serotype 5 (AdHu5), the efficacy of AdC68 vaccination was decreased by approximately 50% when neutralizing antibodies to AdHu5 were present. Although not wishing to be bound by this explanation, this reduction likely is caused by pre-existing T cell that cross-react between adenovirus of the human serotype 5 and the chimpanzee adenoviruses. However, AdC68 vaccinations carrying antigens fused with HSV-1 gD were only weakly influenced by those antibodies (FIG. 4).

Example 4

Interaction of Constructs which Encode Fusion Proteins with HVEM

Figure 10A:
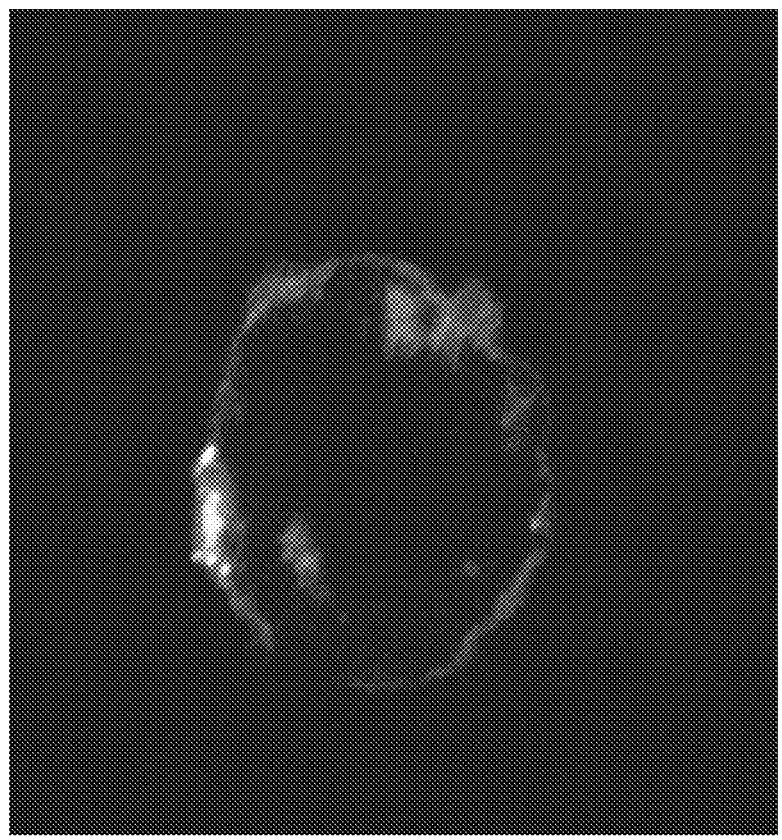
FIGS. 10A-10B depict that gDgag expressed by infected cells bound to HVEM expressed on non-infected cells. Confocal microscopy (FIG. 10A) and FACS analysis (FIG. 10B) were performed to localize gDgag on non-infected cells. CHO-CAR cells were infected with AdC68gDgag. After 48 hours, cells were harvested and washed extensively with cold PBS. AdC68gDgag-infected CHO-CAR cells were cultured with B78H1/3E5 cells, which expresses HVEM-EGFP on the surface, at 4:1 ratio. After 48 hours, cells were stained using the anti-gD monoclonal antibody DL-6 and anti-mouse IgG conjugated to Texas Red (microscopy) or PE (FACS).
Figure 10B:
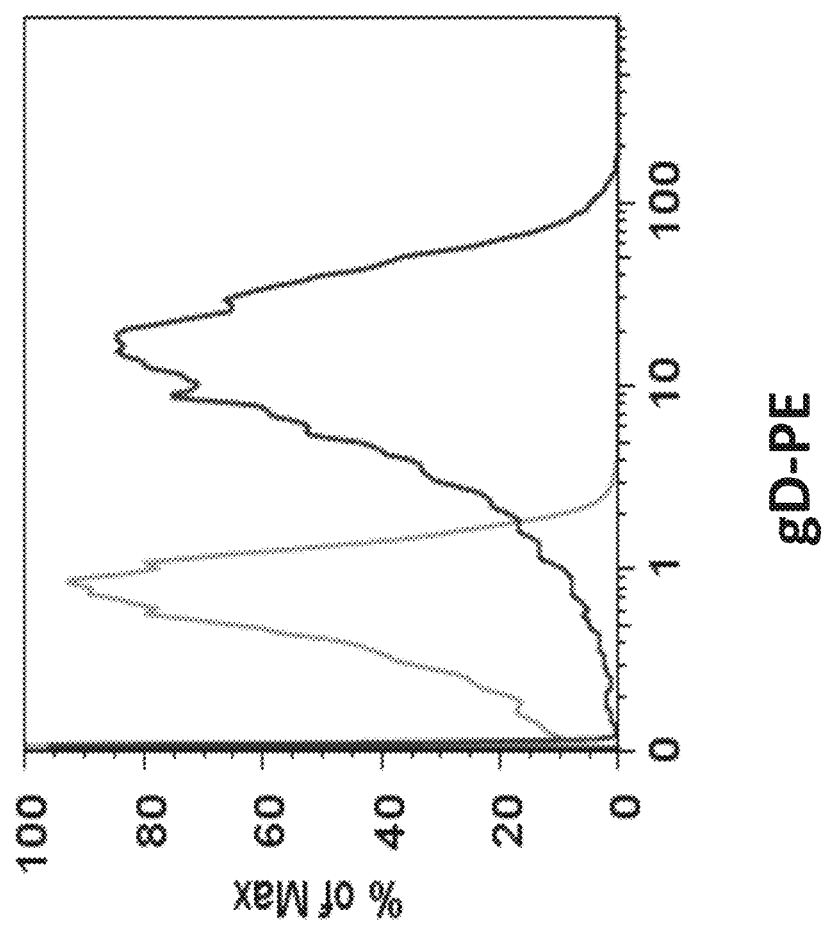
Figure 12:
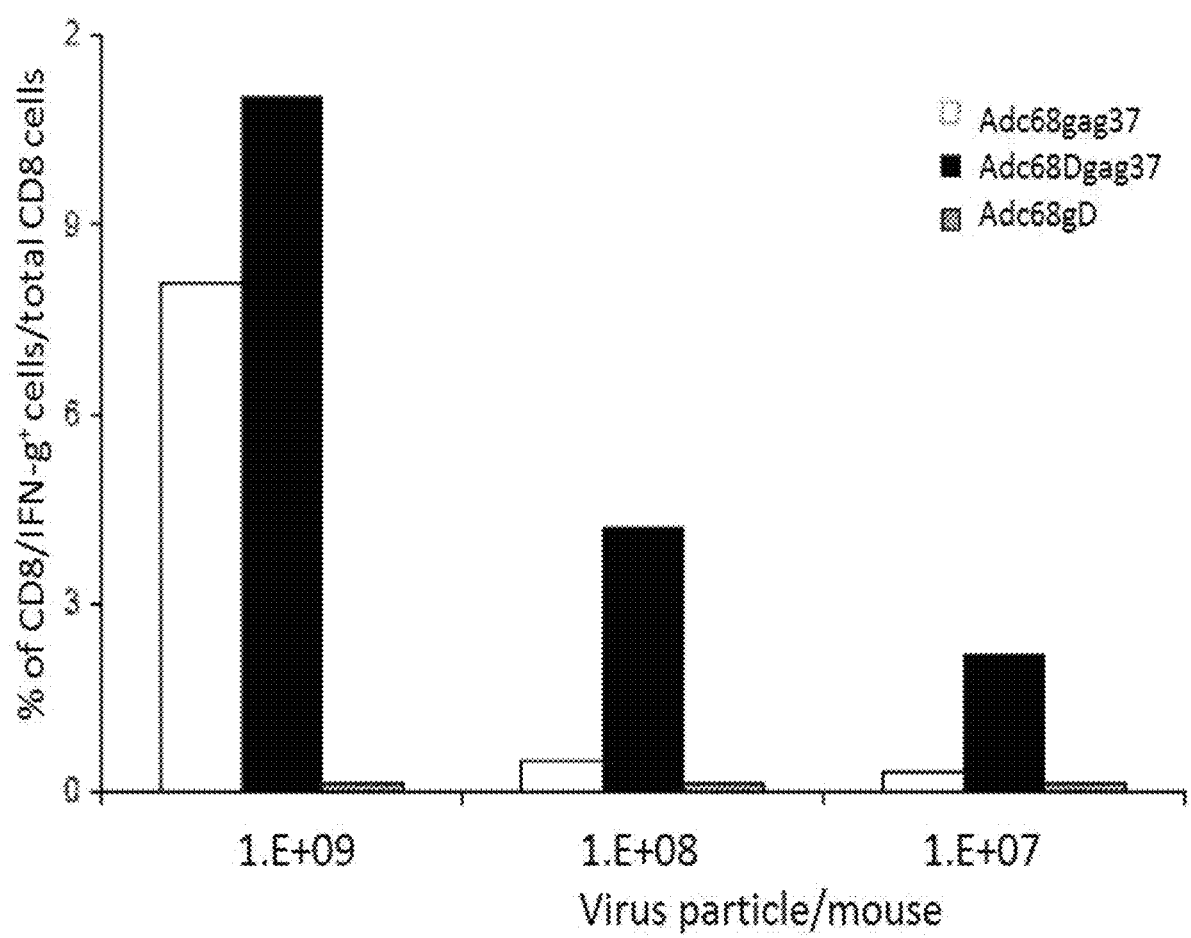
FIG. 12 graphically depicts the gag-specific IFN-γ response of CD8$^+$ T cells from mice immunized with AdC68 vectors. PBMC are from mice immunized with with different amounts of AdC68 vectors carrying either gag, gDgag or gD. Percentage represents CD8$^+$/IFN-γ$^+$ cells over total of CD8$^+$ cells. CD8$^+$/IFN-γ$^+$ frequencies in all groups stimulated with an unrelated control peptide were 0.20%. Data shown are representative of two performed experiments.
Figure 13:
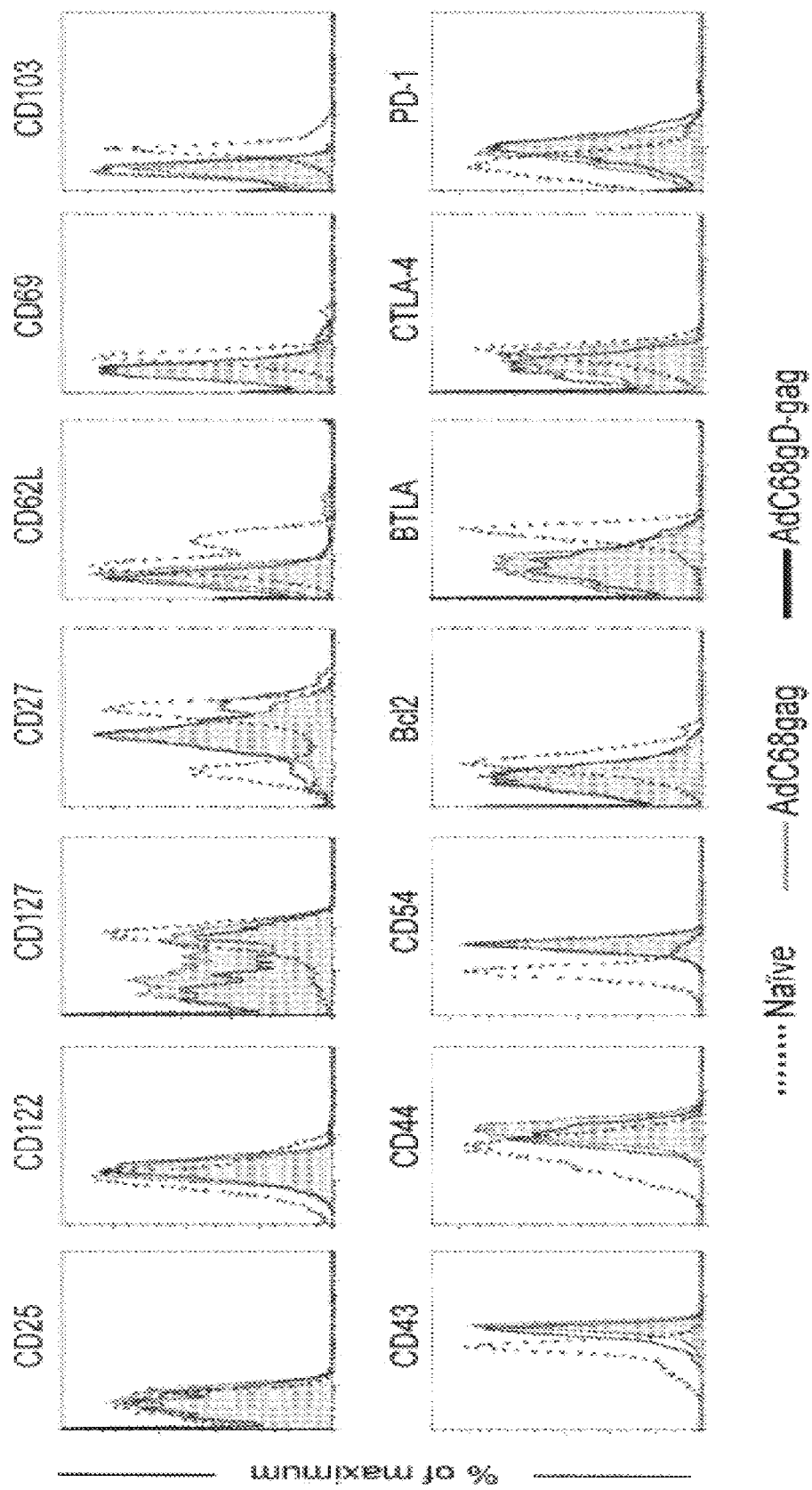
FIG. 13 depicts the phenotypic profile of CD8$^+$ cells activated by AdC68 vaccination. PBMC from naïve mice and mice immunized with AdC68 carrying either gag or gDgag were stained with gag-tetramer-APC and anti-CD8-PerCP, in combination with anti-CD25-PE, anti-CD-122-PE, anti-CD127-PE, anti-CD27-PE, anti-CD62L-FITC, anti-CD69-PE, anti-CD103-PE, anti-CD43-PE, anti-CD44-FITC, anti-CD54-PE, anti-Bcl2-PE, anti-BTLA-PE, anti-CTLA4-PE and anti-PD1-PE. Graphs show data from CD8$^+$/gag-tet$^+$ cells for AdC68gag (gray line) and AdC68gDgag (black line), and total CD8$^+$ for naïve (black dotted line). Data were analyzed on Flowjo software (Tree Star Inc.).

Efficacy of the vaccine was related to the localization of the transgene in relationship the N-terminus of gD. The specific region localized in the N-terminal portion of gD, which interacts with the herpes virus entry mediator (HVEM), was crucial in enhancing stimulation of specific $CD8^+$ T cell mediated immune response. A mutated form of gD chimeric protein gDE7E6E5, called NBEFgDE7E6E5, was generated altering specific gD amino acids (M11A, N15A, L25, Q27A, L28A, T29A, D30A), which promote gD-HVEM interaction. The mutated form of gDE7E6E5 expressed by DNA vaccine was not able to induce an E7-specific $CD8^+$ T cell response, although mutated and non-mutated gDE7E6E5 genes were transcribed at the same level (FIG. 5). On the other hand, a single-amino acid modification on HSV-1 gD (W294A), was able to enhance the efficacy of a gD/E7 fusion DNA vaccine (FIG. 6).

The interaction of HSV-1 gD with HVEM interferes with down-regulation of immune responses associated with HVEM-BTLA (B and T lymphocyte attenuator) pathway. Without intending to be bound by theory, maintenance of gD interference in HVEM-BTLA pathway is a important key to enhance a specific T cell mediated immune response to one or more heterologous antigens. To this end, it was demonstrated that a fusion of an antigen, such as HIV-1 gag, into the C-terminal region of HSV-1 gD did not decrease its affinity to bind to HVEM (FIG. 7). The ability of HSV-1 gD to bind HVEM was not affected by fusion with HIV-1 gag. In fact, the affinity to HVEM of HIV-1 gag/HSV-1 gD chimeric protein was slight higher than non-fused gD.

Confocal microscopy and FACS analyses of cells infected in vitro with AdC68gDgag provided additional evidence that gDgag bound HVEM (FIGS. 8A-8B and FIG. 9). Confocal microscopy indicated that gDgag was co-localized with HVEM on the membrane (FIG. 8A) and inside (FIG. 8B) cells infected with AdC68gDgag. Also, cell surface gD staining on AdC68gDgag-infected cells demonstrated that the amount of gD was greater on cells that expressed HVEM than on cells that did not express HVEM (FIG. 9). These results indicate that gDgag bound HVEM, that part of gDgag expressed by the infected cell bound HVEM inside the cell, and that the complex of gDgag-HVEM was transported from the inside the cell to the cell surface. In addition, confocal microscopy and gD staining indicate that gDgag encoded by AdC68gDgag-infected cell was able to bind to HVEM expressed on the surface of other non-infected cells (FIGS. 10A-10B).

Figure 14:
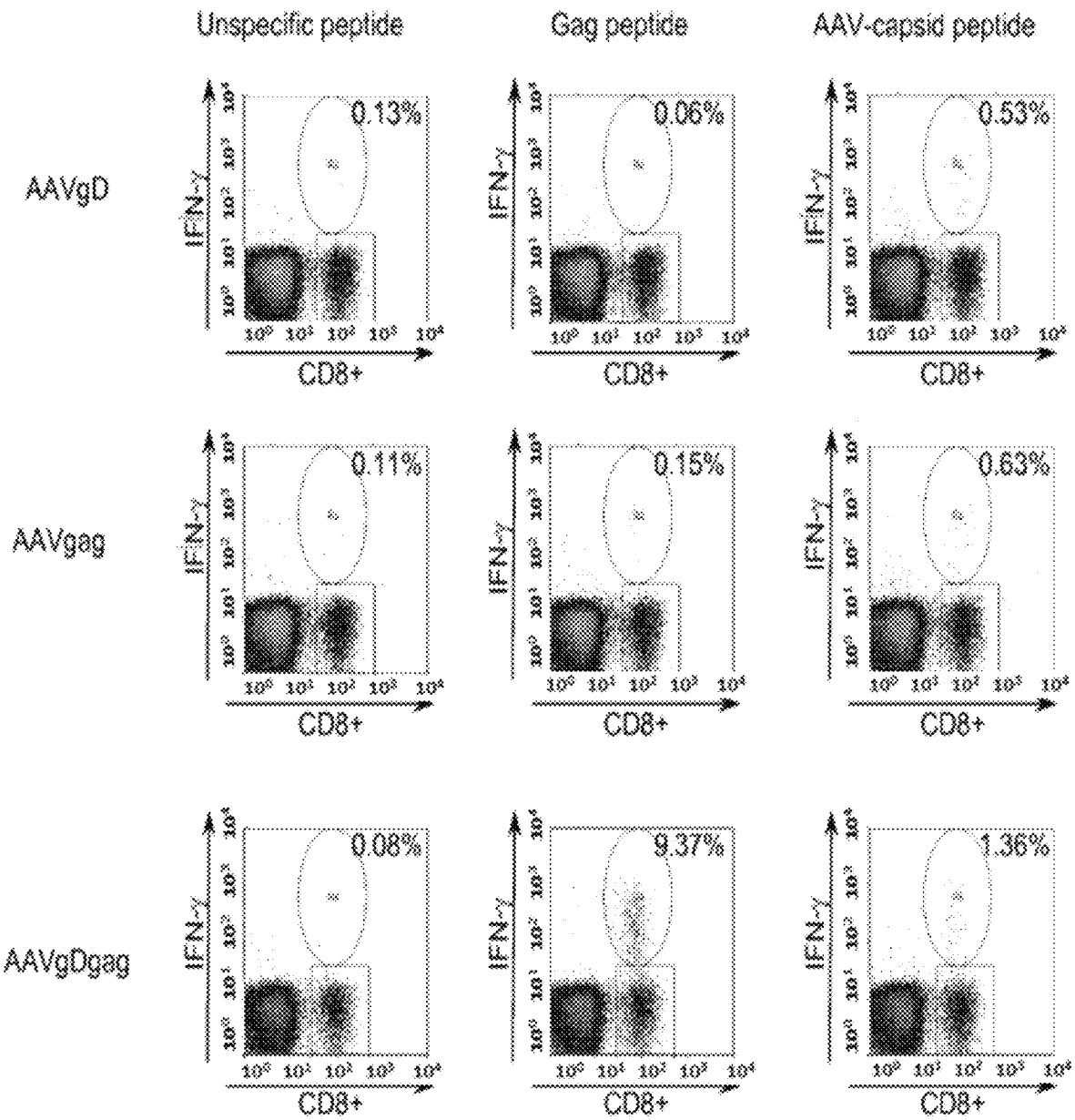
FIG. 14. Intracellular IFN-γ staining of gag-specific and AAV-specific CD8$^+$ T cells from mice immunized with AAV vectors expressing gD, gag or gDgag. Detection of gag-specific and AAV-specific CD8$^+$ T cells was carried out after stimulation of peripheral blood mononuclear cells (PBMCs) with either MHC class I restricted gag peptide or AAV-capsid peptide and cell surface staining for CD8 and intracellular staining for IFN-γ. Unspecific peptide was used as control. The numbers in the right upper corners show the frequencies of peptide-specific CD8$^+$ T cells, as percentages of IFN-γ-producing CD8$^+$ T cells over all detected CD8$^+$ T cells.

Human derived serotype 2 adeno-associated virus (AAV) vectors encoding the gDgag chimeric protein induced higher CD8+ T cell response against gag than AAV vector encoding only gag (FIG. 14). In addition, immunization with AAVgD-gag enhanced CD8+ T cell response against AAV capsid.

Example 5

CD8+ T Cell Response Against NP

Figure 15:
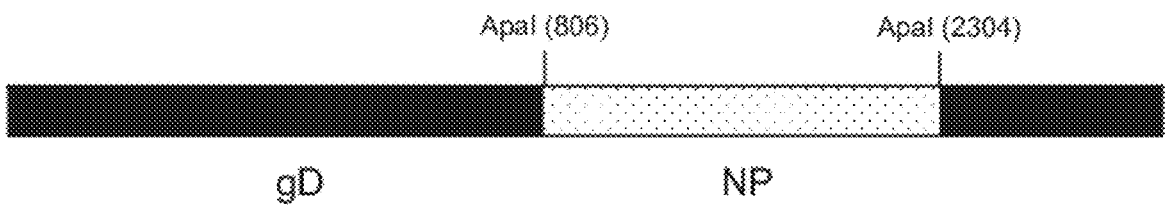
FIG. 15. Schematic representation of chimeric gene gD-NP. Nucleoprotein P (NP) from Influenza virus A/PR8 without its start and stop codons was incorporated into the HSV-1 gD ApaI site, which corresponds to amino acid 244 in the mature form of gD.

The chimeric protein gDNP is composed of the complete open reading frame of HSV-1 gD, into which we incorporated into the ApaI site the nucleoprotein P (NP) gene from Influenza virus A/PR8 without respective start and stop codons (FIG. 15).

Figure 16:
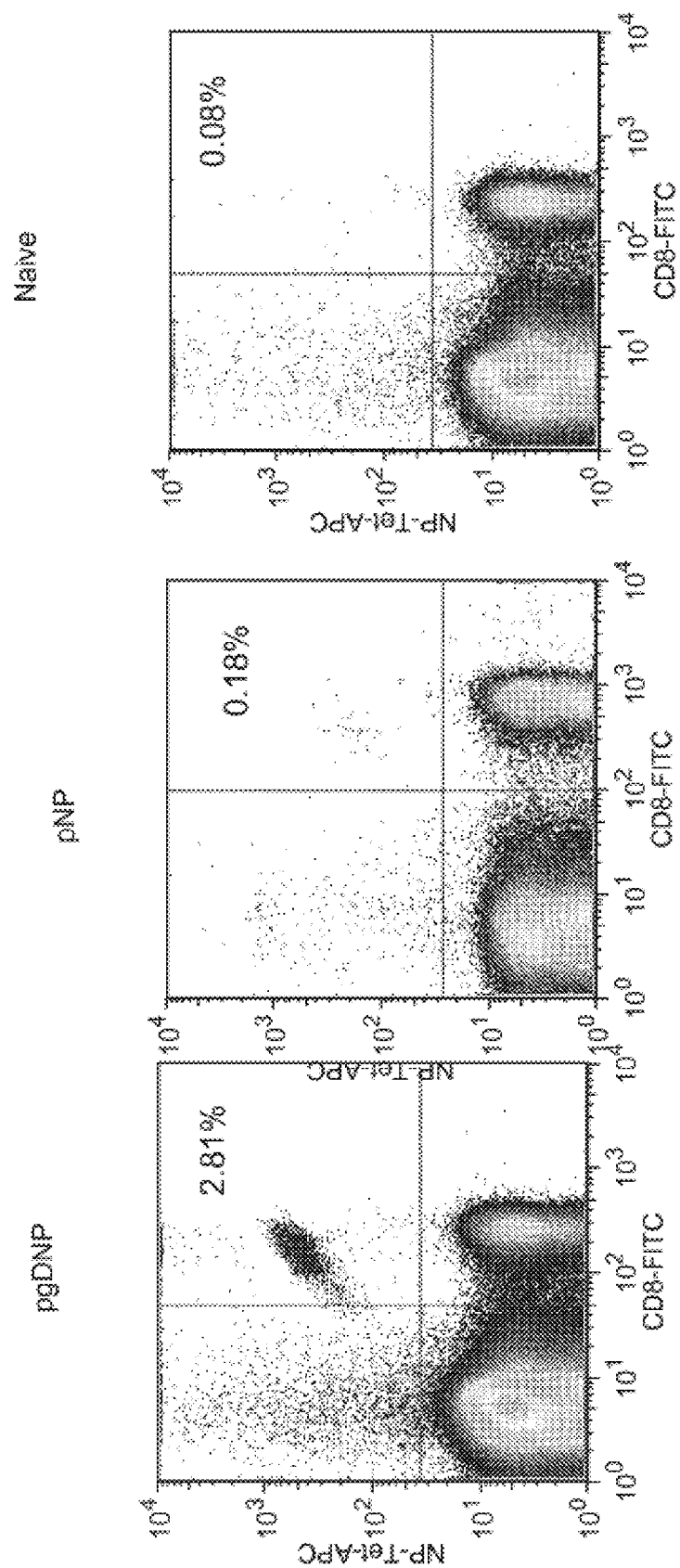
FIG. 16. NP-tetramer staining of CD8$^+$ T cells isolated from blood of mice immunized with either pgD-NP or pNP DNA vaccine. Mice were immunized with 100 μg of each DNA vaccine vector. Fourteen days after immunization peripheral blood mononuclear cells (PBMCs) were isolated and cell surface stained with the NP-tetramer and a labeled antibody to CD8. Naïve mice were used as negative control. Data represent percentages of NP-tetramer$^+$ CD8$^+$ T cells over all detected CD8$^+$ T cells.
Figure 17:
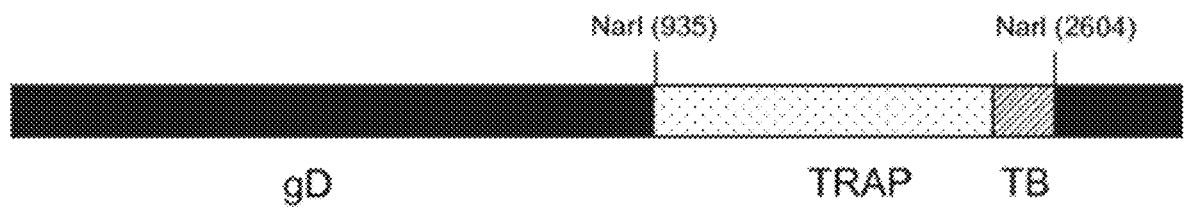
FIG. 17. Schematic representation of chimeric gene gDTRAPTB. Thrombospondin-related anonymous protein (TRAP) from parasite *Plasmodium falciparum* and *Mycobacterium tuberculosis* epitope string (TB) without their start and stop codons are incorporated into the HSV-1 gD NarI site, which corresponds to amino acid 288 in the gD mature form.

Mice were immunized with 100 μg of DNA vaccine vector pgDNP or pNP. Fourteen days after immunization peripheral blood mononuclear cells (PBMCs) were isolated and cell surface stained with the NP-tetramer and a labeled antibody to CD8. Naïve mice were used as negative control. Data are shown in FIG. 16 and represent percentages of NP-tetramer+CD8+ T cells over all detected CD8+ T cells. This experiment demonstrated that the gDNP chimeric protein expressed by DNA vaccine vector induced NP-specific CD8+ T cell response in mice after a single immunization.

Example 6

Molecular Modeling

Figure 18A:
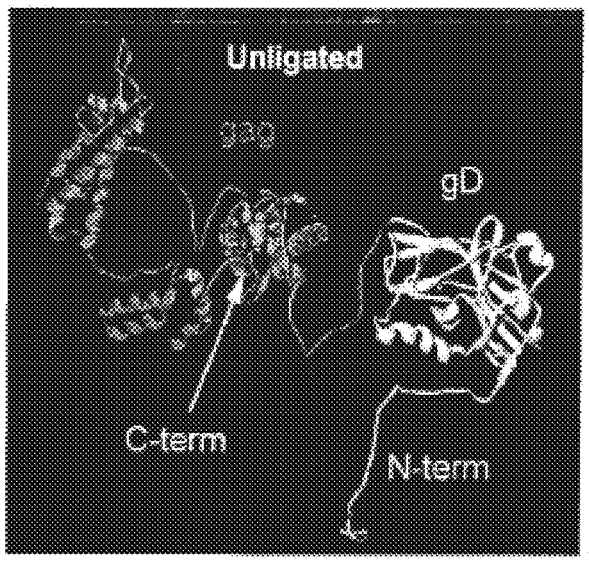
FIGS. 18A-18D. Molecular modeling of the gD-gag chimeric protein. Ribbon representations of gD-gag in the unligated (FIGS. 18A, 18B) and HVEM ligated (FIGS. 18C, 18D) conformations.
Figure 18B:
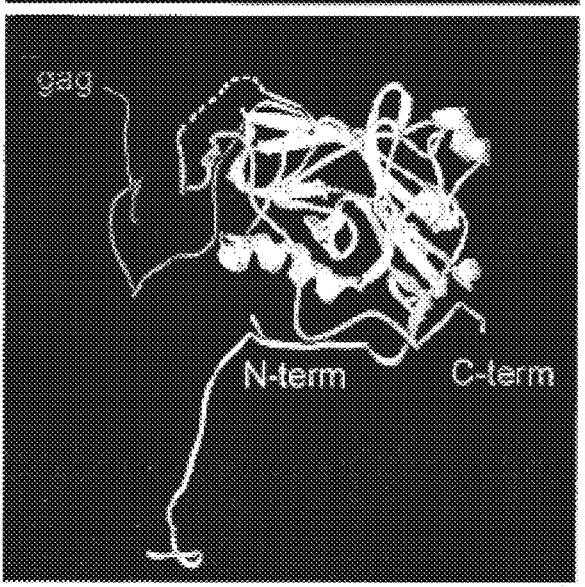
Figure 18C:
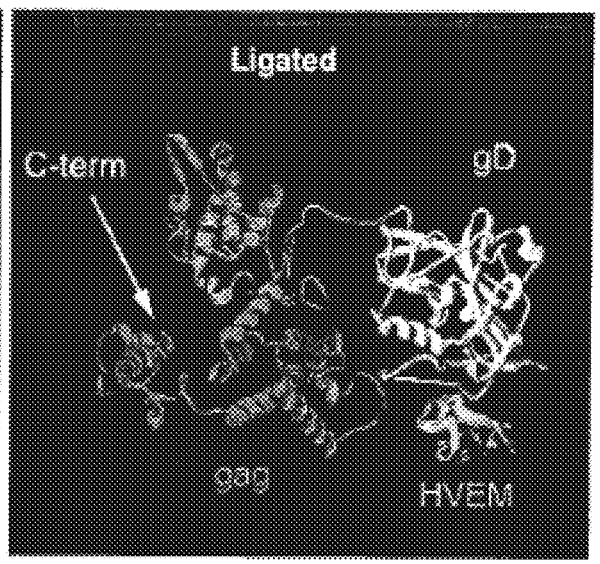
Figure 18D:
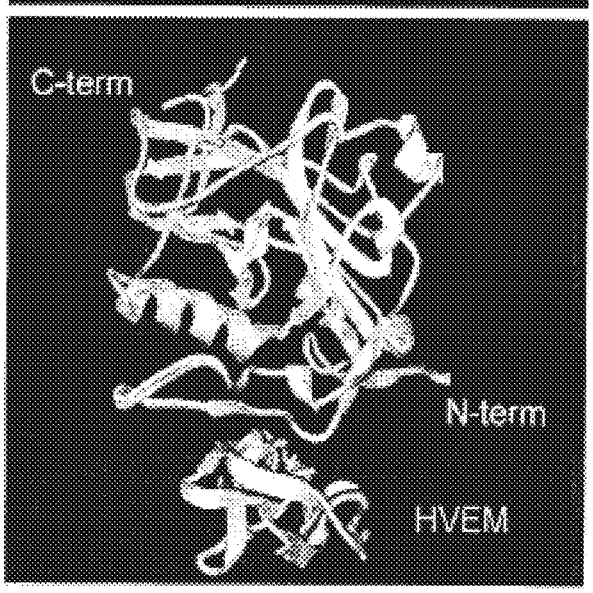
Figure 19:
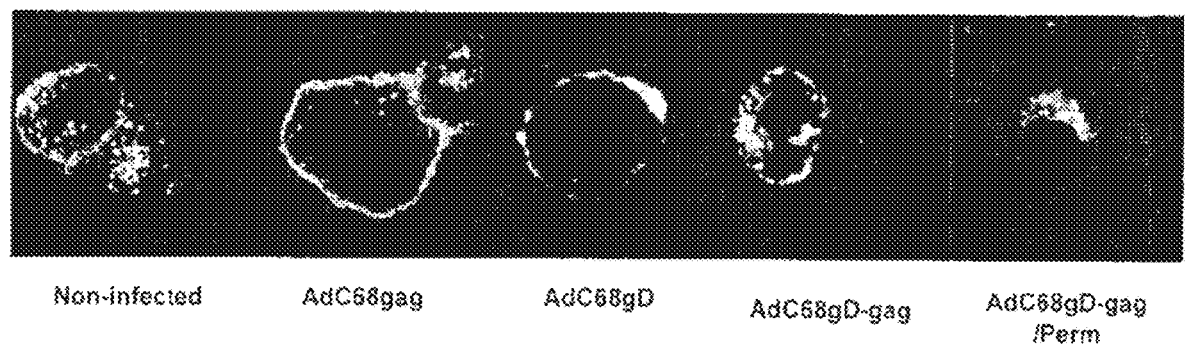
FIG. 19. Confocal microscopy was carried out with B78-H1/3E5 cells, which express HVEM fused to Enhanced Green Fluorescence Protein (HVEM-EGFP). B78-H1/3E5 cells were infected with AdC68gag, AdC68gD or AdC68gD-gag, then stained anti-gD DL-6 MAb and anti-mouse IgG conjugated with Texas Red. AdC68gD-gag-infected cells were permeabilized then stained as above. Cells were examined with a Leica TCS SP2 Confocal Microscope at 400× final magnification.
Figure 20:
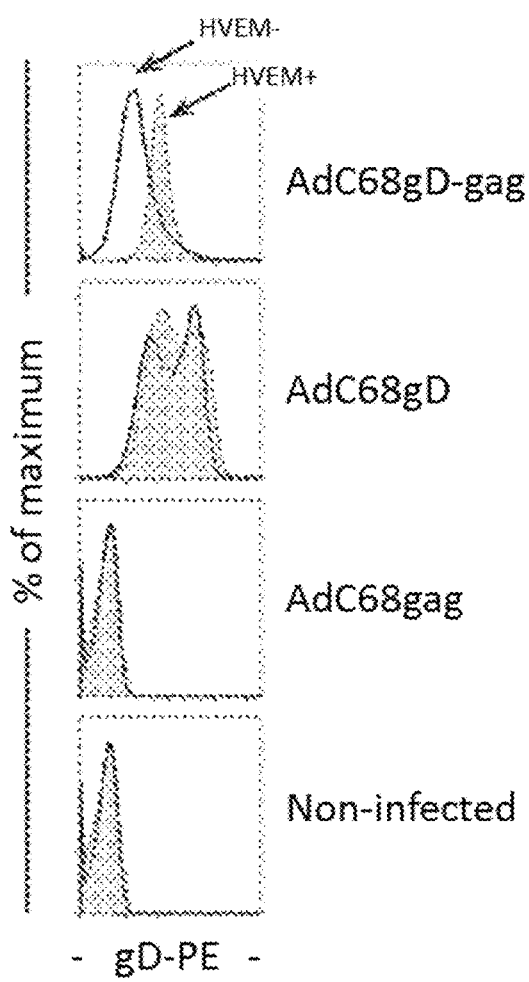
FIG. 20. Comparison of gD expression on the surface of B78-H1 (black line) and B78-H1/3E5 (gray) cells infected with AdC68 vectors carrying gD-gag, gD or gag.
Figure 21:
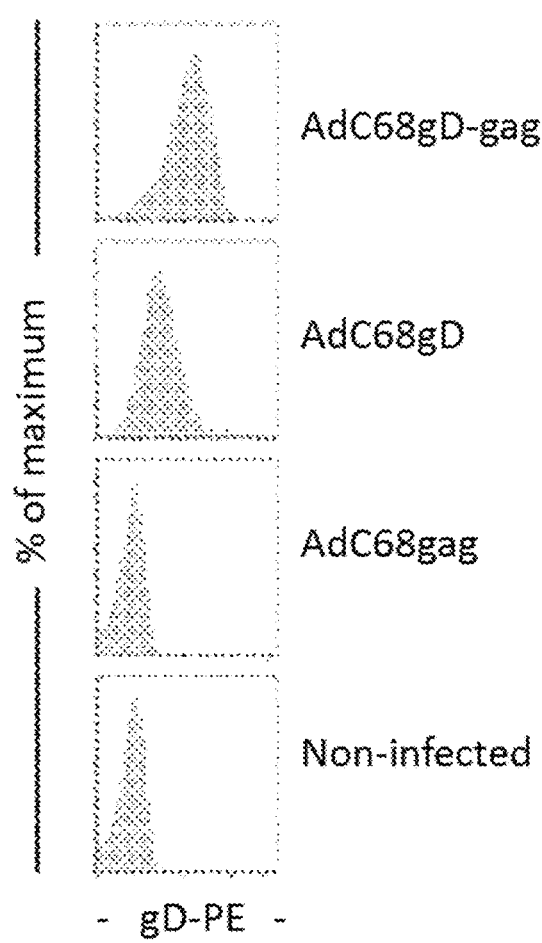
FIG. 21. Presence of gD on the surface of non-infected HVEM$^+$ cells co-cultivated with HVEM$^-$ cells infected with either AdC68gD-gag, AdC68gD or AdC68gag. Non-infected cells were used as negative control.
Figure 22:
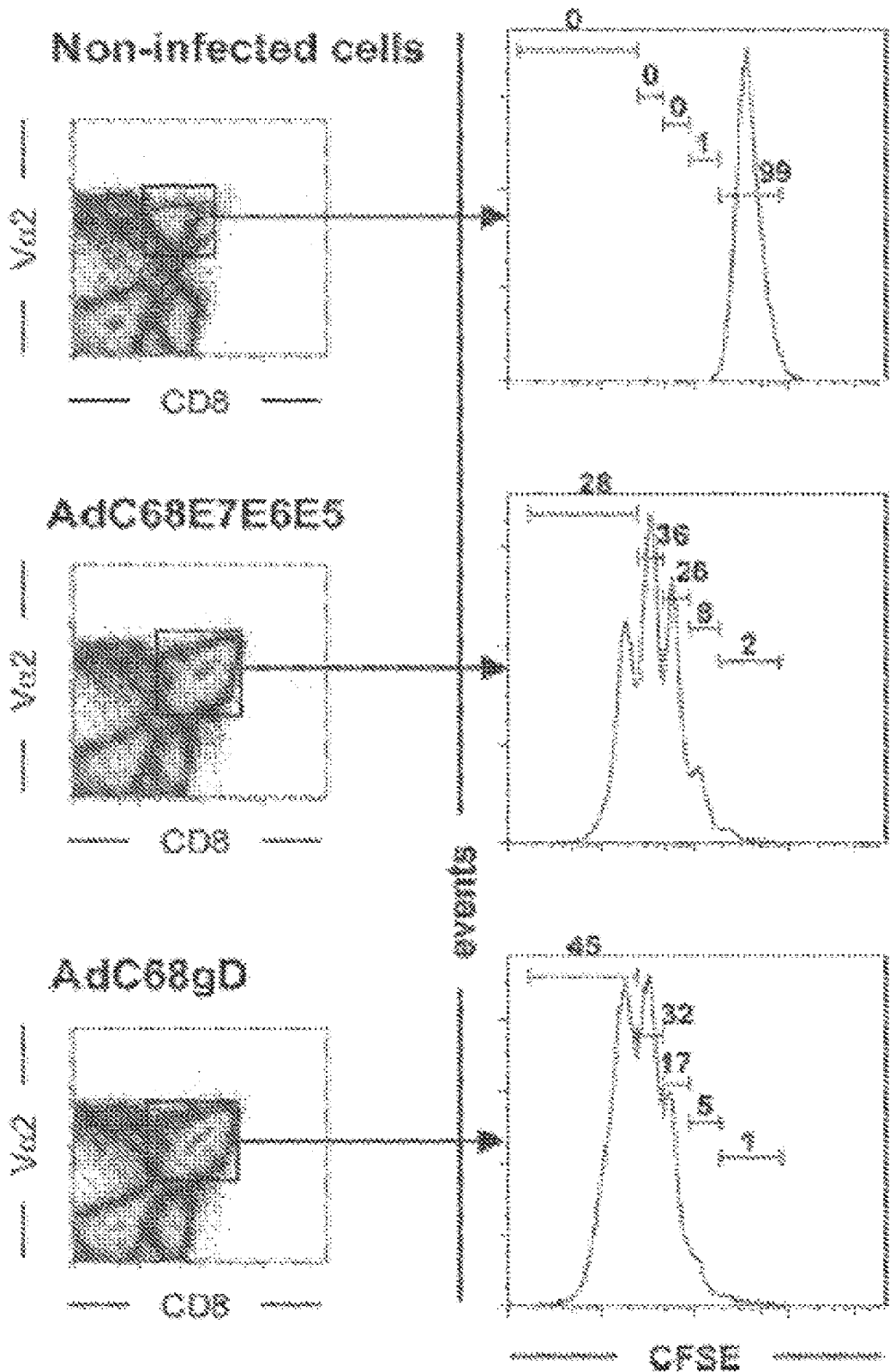
FIG. 22. AdC68gD induces enhanced expansion of CD8$^+$ T cells in vitro. Irradiated lymph nodes cells from naïve mice and mice immunized with either AdC68E7E6E5 or AdC68gD were incubated with CF SE-labeled CD8$^+$ OT-1 (Vα2$^+$) cells for 72 hrs. Total live cells (left) were analyzed for expression of CD8⁺Vα2⁺. CSFE expression by these double positive populations (highlighted by the squares on the right graphs) is shown on the left graphs. The bars and numbers show from right to left the percentages of the population that underwent no replication, 1, 2, 3 or ≤4 cycles of replication. Graphs show data from one representative experiment of two performed.
Figure 23A:
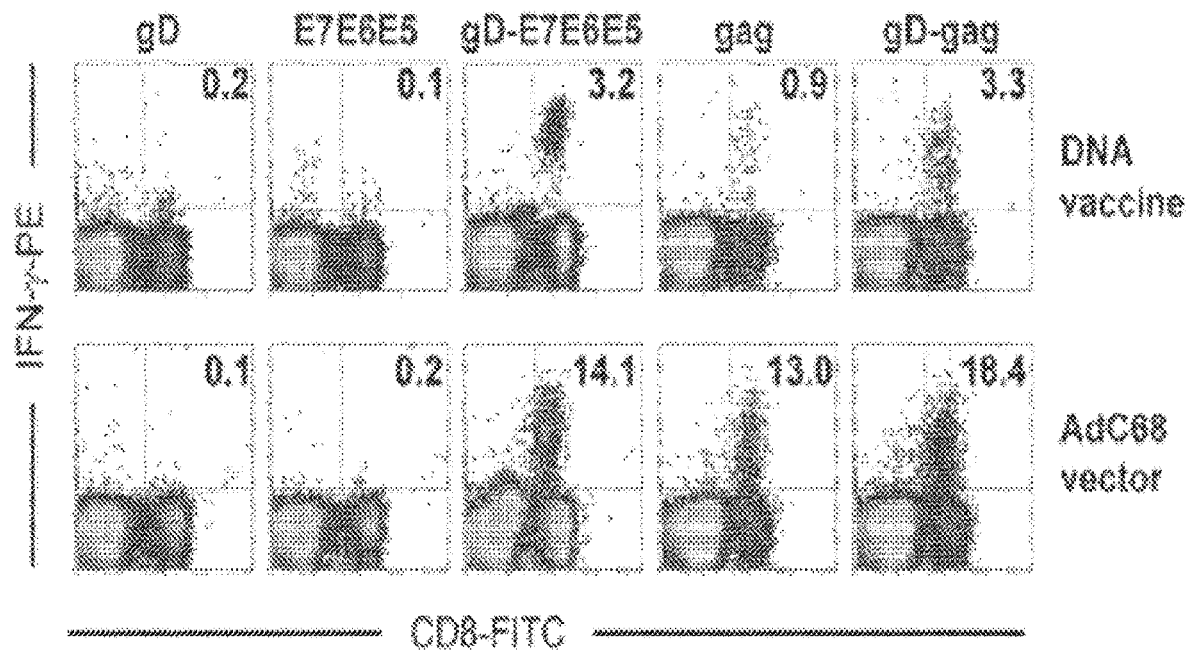
FIGS. 23A-23C. CD8⁺ T cell responses to vectors expressing antigens fused to gD.
Figure 23B:
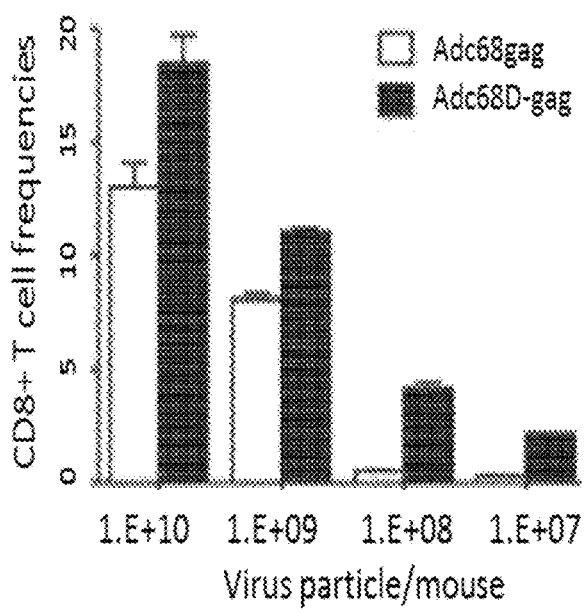
Figure 23C:
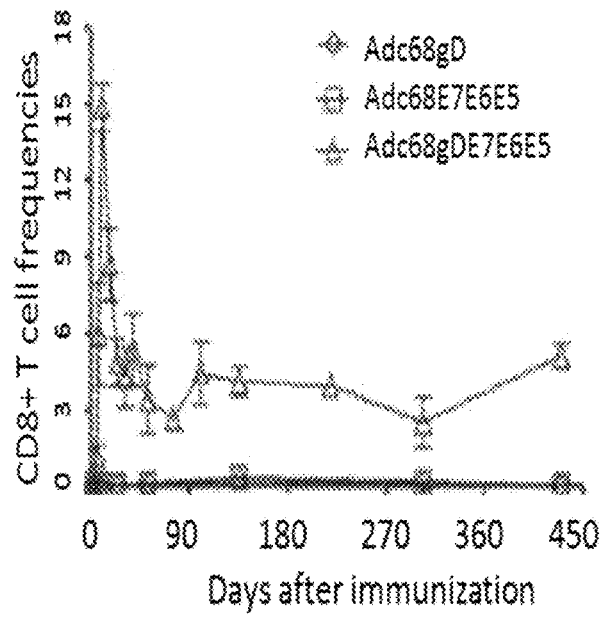

To examine how insertion of a foreign sequence within the C terminus may modify folding of gD we modeled the structure of unligated gD-gag (FIGS. 18A, 18B) and of gD-gag bound to HVEM (FIGS. 18C, 18D). The C-terminus of the native unligated gD structure is anchored near the N-terminal region and thus masks the HVEM binding site (Krummenacher et al., *EMBO J.* 24, 4144-53, 2005; FIG. 19). However, computational modeling of the gD-gag structure predicts that the C-terminus would be shifted away from the N-terminal portion without altering the core structure or the N terminus, which is required to form the HVEM binding site (FIGS. 18A, 18B). A superposition of X-ray structure of gD upon the gD-gag model indicates that insertion of gag into gD does not disrupt the integrity of the HVEM binding surface (FIGS. 18B, 18D).

Example 7

Cellular Localization of Chimeric gD Proteins

Binding of gD to HVEM presumably depends on secretion or cell surface expression of gD. To determine the cellular localization of the chimeric gD-gag protein, B78-H1/3E5 cells, which express human HVEM-EGFP on their surface, were infected with AdC68gag, AdC68gD or AdC68gD-gag, stained with a monoclonal antibody (MAb) to gD and analyzed by confocal microscopy (FIG. 19). Both gD and gD-gag co-localize with HVEM on the surface of infected cells as well as within infected cells. Similar results were obtained upon staining of cells with antibodies to gag. Absolute levels of gD-gag expressed on the surface of infected cells were below those of native gD (FIG. 20). Analyses of mRNA levels showed that all vectors transcribed the chimeric genes at equal amounts to their corresponding non-chimeric versions. Thus the lower levels of cell surface expression of the chimeric protein suggest inefficient secretion, rapid re-internalization of gD-gag or accelerated proteolytic degradation. The presence of HVEM on the cell surface increased the amount of gD-gag (FIG. 20) on the cell surface suggesting that intracellular binding of HVEM to gD-gag stabilized gD-gag or facilitated export of the chimeric protein.

When AdC68gD or AdC68gD-gag infected HVEM negative (HVEM$^-$) cells were mixed with uninfected cells expressing HVEM (HVEM$^+$), both gD and gD-gag co-localized with HVEM on the uninfected HVEM$^+$ cells indicating that some of the protein was released and then bound to HVEM. This was more pronounced with gD-gag than with gD, and may reflect either increased secretion of the chimeric protein or its superior binding to HVEM (FIG. 21). To ensure that the observed transfer of gD or gD-gag from HVEM$^-$ to HVEM$^+$ cells was not a result of cell fusion, cells were stained for an additional marker, the coxsackie adenovirus receptor (CAR), expressed only by the HVEM$^-$ cell line. Uninfected HVEM$^+$ cells which co-stained for gD failed to express CAR thus ruling out cell fusion.

Example 8

Expression of Antigens within gD Augments Antigen-Specific CD8$^+$ T Cell Responses To determine if expression of an antigen within gD affects stimulation of CD8$^+$ T cells in general to epitopes presented on gD transduced antigen presenting cells we initially performed proliferation assays. Irradiated cells from draining lymph nodes of mice intramuscularly (i.m.) immunized with AdC68 carrying either gD or E7E6E5 were pulsed with low amounts of the SIINFEKL peptide and served as antigen presenting cells for carboxyfluorescein diacetate succinimidyl diester (CFSE)-labeled CD8$^+$ T cells from OT-1 mice, which carry CD8$^+$ T cells with a transgenic receptor for SIINFEKL in the context of Kb. We had shown previously that i.m. application of an AdC68 vector causes an accumulation of vector transduced mature dendritic cells within draining lymph nodes[26]. We thus expected that upon application of the AdC68gD vector some of the mature dendritic cells would express gD, which in turn may modulate the response of OT-1 derived CD8$^+$ T cells to their cognate antigen. As shown in FIG. 22, OT-1 CD8+ T cells proliferated more vigorously upon co-culture with lymph node cells from AdC68gD injected mice than upon co-culture with cells from AdC68E7E6E5 injected mice.

To evaluate if blockade of the HVEM inhibitory pathway enhances adaptive immune responses in vivo, we vaccinated mice with DNA and AdC68 vectors expressing the gD-antigen chimeric proteins and tested T and B cell responses in comparison to those of mice injected with vectors expressing E7, E6 and E5 or gag without gD. Mice fail to mount detectable E7-specific CD8$^+$ T cell responses following vaccination with DNA or AdC68 vectors encoding either E7E6E5 (FIG. 23A) or E7 alone. In contrast, the DNA vaccine and the AdC68 vector expressing E7 or the fusion polypeptide of E7, E6 and E5 within gD induce robust E7-specific CD8$^+$ T cell responses. Similarly, the DNA vaccine expressing the gD-gag chimeric protein stimulate more potent gag-specific CD8$^+$ T cell responses compared to vectors expressing gag only (FIG. 23A). The AdC68 vector expressing the gD-gag chimeric protein also elicits stronger gag-specific CD8$^+$ T cells than those expressing gag only, which was especially pronounced at low vector doses (FIGS. 23A, 23B). To determine the longevity of vaccine-induced responses, E7-specific CD8$^+$ T cells were monitored for over a year following vaccination with the AdC68gD-E7E6E5 vectors. CD8$^+$ T cell responses were maintained at stable frequencies indicating that the enhancement of the initial primary T cell response resulted in an increase of the memory T cell population (FIG. 23C).

Example 9

Expression of Antigens within gD Increases Antigen-Specific Antibody Responses

It is well established that neutralizing antibodies are the primary correlate of vaccine-induced protection against most virus infections. LIGHT stimulation enhances both B cell proliferation and immunoglobulin production[27] and might balance inhibition exerted by ligation of BTLA to HVEM. To analyze whether antibody responses can be enhanced by the gD-antigen chimeric proteins, sera of mice immunized with the AdC68 vectors expressing gag or gD-gag were analyzed for antibodies to gag (Table 4).

TABLE 4

Gag-specific antibody response after immunization with AdC68 vectors expressing gD, gag, or gD-gag.

| | Anti-gag antibody titer ± SD$^a$ (p value)$^b$ | | | |
|---|---|---|---|---|
| Immunization | 10 days | 7 weeks | 20 weeks | 49 weeks |
| AdC68gag | 26 ± 8 | 35 ± 8 | 152 ± 19 | 6 ± 4 |
| AdC68gD | 3 ± 4 (0.007) | 9 ± 4 (0.0037) | 28 ± 15 (0.0004) | 8 ± 2 (0.2573) |
| AdC68gD-gag | 287 ± 7 (2.6E−7) | 740 ± 2 (6.8E−9) | 1257 ± 21 (4.8E−6) | 294 ± 8 (3.3E−7) |

$^a$Anti-gag Ig titers were established as the reciprocal of the serum dilution that gave an adsorbance twice above that of the sera from naïve mice. SD-standard deviation.
$^b$p-values were determined using one-tailed Student t test comparing titers either from mice immunized with AdC68gD or AdC68gD-gag with titers from mice immunized with AdC68gag.

The AdC68gag vector induces only marginal levels of gag-specific antibodies while AdC68gD-gag vector elicits a significantly higher response that remained detectable for at least 11 months. Antibody responses to gD, measured in parallel, were comparable in mice vaccinated with the AdC68gD or the AdC68gD-gag vector.

Example 10 gD HVEM Interaction is Needed to Augment Immune Responses

Figure 24A:
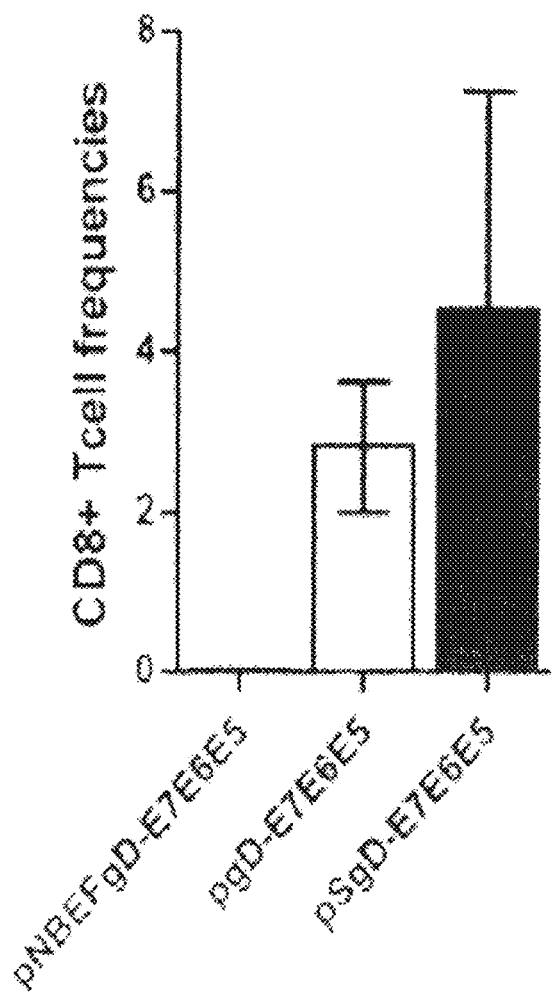
FIGS. 24A-24B. The enhancement of CD8⁺ T cell responses requires binding of gD to HVEM.
Figure 24B:
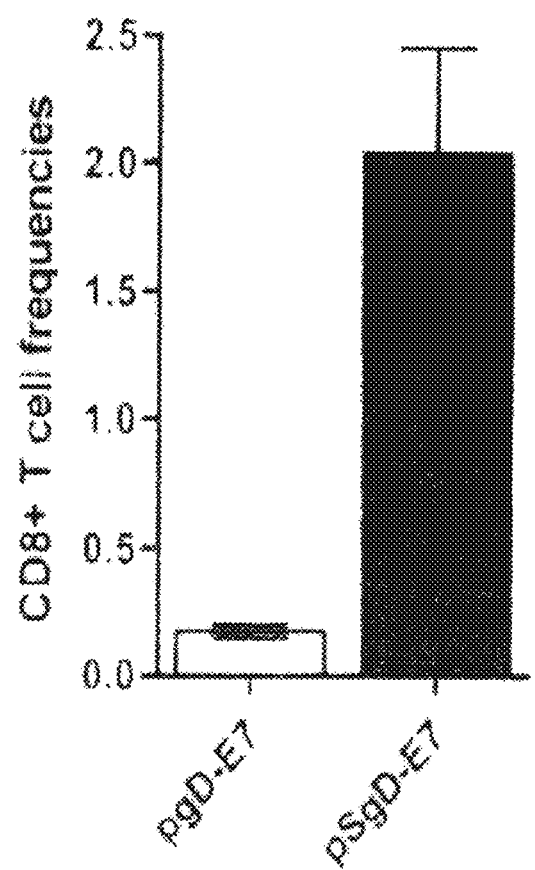

To determine if enhancement of the CD8+ T cell responses by expression of an antigen within gD requires binding of gD to HVEM, we constructed DNA vaccines expressing the E7E6E5 sequence within two modified versions of gD; In one construct, termed NBEFgD-E7E6E5, 7 amino acids at the N-terminus of gD, i.e., M11, N15, L25, Q27, L28, T29 and D30, were replaced with alanine residues. Previous studies have shown that these 7 amino acids on wild type gD are crucial to gD-HVEM interaction[13]. In a second construct, termed SgD-E7E6E5, the tryptophan (W) in position 294 of gD was changed to alanine (A). This modification, which is thought to destabilize the native conformation of the gD C-terminus, was shown to increase binding of gD306 to HVEM[15]. Mice immunized with one dose of a DNA vaccine expressing NBEFgD-E7E6E5 failed to mount detectable frequencies of E7-specific CD8+ T cells (FIG. 24A). In contrast, frequencies of E7-specific IFN-γ+CD8+ T cells induced by pSgD-E7E6E5 were higher compared to those induced by pgD-E7E6E5 (FIG. 24A), although this difference did not reach statistical significance. To confirm this observation we also modified the pgD-E7 DNA vaccine[28], which carries only E7 inserted into gD, by changing the tryptophan in position 294 to alanine. This new vector, termed pSgD-E7, stimulated significantly higher frequencies of E7-specific CD8+ T cells compared to a plasmid vector expressing E7 within the wild-type form of gD (FIG. 24B). Taken together, these results demonstrate that binding to HVEM is essential for the immunopotentiating effect of gD and that gD mutations that increase its binding to HVEM can under some conditions further augment CD8+ T cell responses.

Example 11

Functionality of CD8+ T Cells Induced by gD Chimeric Proteins

Figure 25:
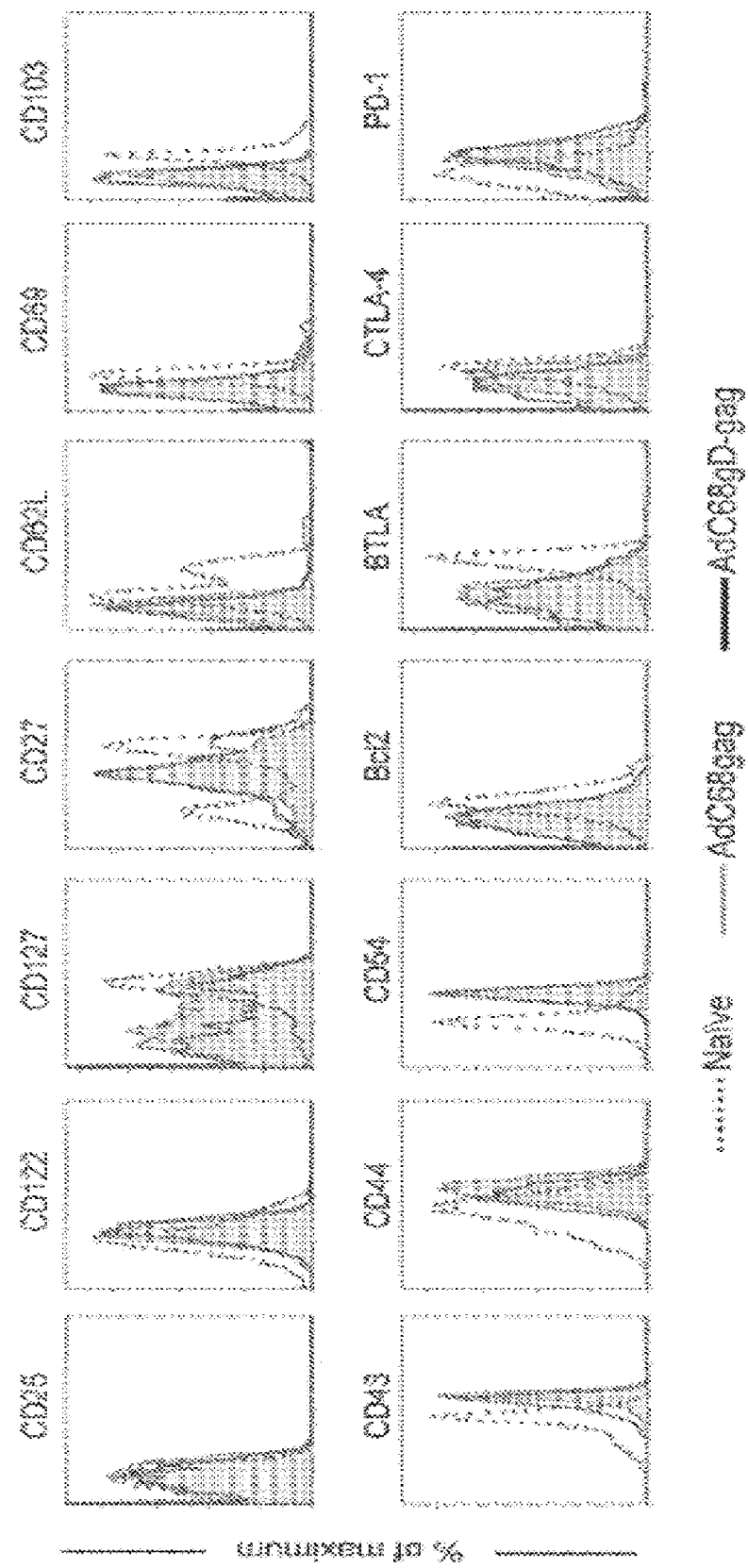
FIG. 25. Phenotypes of gag-specific CD8⁺ T cells were analyzed on PBMCs from mice immunized with either AdC68gD-gag or AdC68gag. PBMCs were isolated 10 days after immunization. Naïve mice were used as controls (black dotted line). The graphs shown reflect expression levels of total CD8+ T cells from naïve mice (black dotted line) and gag-tet⁺CD8⁺ T cells from mice immunized with either AdC68gag (grey line) or AdC68gD-gag (black line).

Modulation of regulatory pathways may affect the functionality of the resultant T cell responses. Phenotypes of vaccine-induced CD8+ T cells were analyzed from mice immunized with AdC68 vectors expressing gD-gag or gag (FIG. 25). We measured expression of the following phenotypic markers, i.e., CD25, CD122, CD127, CD27, CD62L, CD69, CD103, CD43, CD44, CD54, Bcl2, BTLA, CTLA-4 and PD-1 on gag-specific CD8+ T cells (FIG. 25). Most of the markers tested (CD122, CD127, CD27, CD62L, CD69, CD103, CD43, CD44, CD54, Bcl2, BTLA, CTLA-4 and PD-1) are modulated on antigen-specific CD8+ T cells as compared to naïve CD8+ T cells and for most markers expression levels on CD8+ T cells induced by gag or gD-gag are identical. CD27 is increased on a subpopulation of gD-gag induced gag-specific CD8+ T cells, while CTLA expression is marginally lower when compared to CD8+ T cells induced by gag alone. Overall, although AdC68gD-gag elicits higher frequencies of gag-specific CD8+ T cells than AdC68gag, the phenotypic profiles of the resultant effector cells are very similar. IFN-γ+CD8+ T cells induced by gD-gag or gag respond to the same epitope when tested against a panel of gag peptides, indicating that expression of gag within gD does not increase the breadth of the CD8+ response.

T cell functionally was further accessed by testing if mice vaccinated with either DNA (FIG. 26A) or AdC68 vectors (FIG. 26B) expressing E7E6E5 with or without gD were protected against challenge with TC-1 cells, which are lung epithelial cells derived from C57Bl/6 mice that are transformed with v-Ha-ras and the E6 and E7 oncoproteins of HPV-16[26]. Animals immunized with pgD-E7E6E5 or AdC68gD-E7E6E5 were completely protected against TC-1 tumor progression, and protection was only seen upon vaccination with constructs carrying gD fusion proteins. Mice vaccinated with DNA vaccines expressing E7 or E7E6E5 within mutant forms of gD were also tested for protection against TC-1 tumor formation (FIG. 26C). Protection correlated with CD8+ T cell responses; mice immunized with a vector expressing E7E6E5 within the form of gD that can not bind to HVEM were not protected while mice immunized with the same antigen expressed within the gDW294A variant were fully protected. Additionally, animals immunized once with a DNA vaccine expressing only E7 within gD developed tumors while those that expressed E7 within the gDW294A variant were completely protected.

Discussion of Examples 2-11

Incorporation of the antigens into the extracellular C-terminal domain of gD markedly increases vaccine-induced CD8+ T and B cell responses. As demonstrated in the specific examples, above, this is especially pronounced for CD8+ T cell responses to E7, which expresses a T cell epitope with low to moderate affinity to H-2 $K^b$ (He et al., virol. 270, 146-61, 2000). A single dose of DNA vaccines or AdC68 vectors expressing the E7E6E5 polypeptide fails to elicit detectable CD8+ T cell responses or protective immunity to challenge with an E7-expressing tumor cell line, while the same antigen expressed within gD by either vector results in high and sustained frequencies of E7-specific CD8+ T cells and complete protection against tumor cell challenge. Gag of HIV-1 carries a high affinity epitope for mice of the $H-2^d$ haplotype and DNA vaccines or AdC68 vectors (Fitzgerald et al., J. Immunol. 170, 1416-22, 2003) expressing gag induce readily detectable CD8+ T cell responses. Responses to gag are also increased upon expression of gag within gD.

The immunopotentiating effect of gD on the response to gag is more impressive when the gD-gag chimeric protein is delivered by a DNA vaccine rather than by the highly immunogenic AdC68 vector. Upon dose reduction of the AdC68 vector, results clearly demonstrate that an induction of gag-specific CD8+ T cells can be achieved with an approximately 100 fold lower vaccine dose than needed for the AdC68 vector expressing gag only. This is important because Ad vectors of the common human serotype 5 (AdHu5) when tested in clinical trials as vaccine carriers for antigens of HIV-1 encountered dose limiting toxicity (Kresge, IAVI rep. 9, 18-20, 2005). Reactogenicity at high doses in humans is also anticipated with the chimpanzee-origin Ad vectors such as AdC68, which was developed to circumvent the effect of neutralizing antibodies to common human serotypes of adenovirus. Thus, further improvement of the immunogenicity of Ad vector vaccines that allows for a substantial dose reduction while maintaining efficacy could lower vaccine-related side effects, reduce the overall cost of the vaccine and facilitate production for mass vaccination. Increased efficacy may also lessen the need for complex prime boost regimens that are currently being tested in clinical HIV-1 vaccine trials but that may be unmanageable and too costly for developing countries.

Insertion of antigens into gD does not affect the functionality of antigen-specific CD8+ T cells; T cells induced by the gD chimeric proteins protect against tumor challenge in the E7 model, are phenotypically similar to those induced in absence of gD, and efficiently differentiate into memory cells as shown with gag-expressing AdC68 vaccines, confirming a previous study with BTLA-deficient T cells (Krieg et al., Nat. Immunol. 8, 162-71, 2007).

Antibody responses are also augmented by expressing the antigen within gD. LIGHT participates in B cell expansion as a co-stimulus of CD40 and induces antibody production (Duhen et al., Eur. J. Immunol. 34, 3534-41, 2004). The control of LIGHT-induced B cell activation appears to be provided by down-regulation of HVEM following its engagement by LIGHT (Duhen et al., 2004). BTLA is constitutively expressed on B cells and BTLA deficient mice mount higher antibody responses compared to wild-type mice although this effect was shown previously to be modest (Hurchla et al., J. Immunol. 174, 3377-85, 2005). In contrast, in our vaccine model, antibody responses were markedly enhanced upon expressing gag within gD. While not wishing to be bound by the explanation, this may reflect that binding of gD to HVEM augments CD4+ T cell responses, which in turn promote activation of B cells. Alternative pathways such as an enhancement of the co-stimulatory HVEM-LIGHT pathway may also have contributed.

Binding of gD to HVEM is essential for augmentation of CD8+ T cell responses to the fusion partner as vaccines expressing antigen within a modified gD in which the HVEM binding site had been obliterated fail to induce enhanced CD8+ T cell responses. In the native unligated structure form of gD, the C-terminus largely obstructs movement of the N-terminus into its HVEM-binding conformation (Krummenacher et al., EMBO J. 24, 4144-53, 2005). According to our molecular model, insertion of foreign sequences of certain lengths such as gag or the E7E6E5 polypeptide may effect a structural change of gD which improves its binding to HVEM. This may not be achieved by short sequences such as E7 alone, for which the immunogenicity and efficacy of the gD chimeric vaccines can be improved further through a single amino acid exchange in position 294 of gD which had been described previously to improve binding of gD to HVEM (Krummenacher et al., 2005).

Manipulation or disruption of negative regulatory pathways has been shown previously to augment T cell responses. Recent reports showed that antibody-mediated interruption of the PD1-PD-L1 pathway reverses T cell exhaustion caused by chronic infections and allows for increased T cell proliferation (Barber et al., Nature 439, 682-87, 2006; Day et al., Nature 443, 350-54, 2006). Manipulation of this pathway may not readily affect primary T cell responses as PD1 requires induction by activation and is not expressed on naïve T cells (Barber et al., 2006). In contrast, low levels of BTLA are expressed on naïve T cells; the levels rapidly increase upon T cell activation and then decline (Hurchla et al., 2005; Han et al., J. Immunol. 172, 5931-39, 2004).

Medicinal targeting of immunoregulatory pathways can result in immunopathology such as the devastating cytokine storms observed upon application of anti-CD28 antibodies to human volunteers (Suntharalingam et al., NEJM 355, 1018-28, 2006) or auto-immunity commonly seen in genetically modified mice (Watanabe et al., Nat. Immunol. 4, 670-79, 2003). The use of a gD-antigen chimeric protein to enhance the immunogenicity of vaccines has the advantage that it does not involve systemic interruption of an inhibitory pathway but rather exerts its effects locally to the site of antigen presentation. We confirmed the spatially limited effect of gD experimentally by injecting two Ad vectors expressing either gD or E7E6E5 into distant anatomical sites (left leg versus right leg) and failed to observe enhancement of antigen-specific CD8+ T cell responses. It has been suggested previously that targeting of BTLA through inhibitory antibody or small molecules may enhance vaccine immunogenicity. Results shown here suggest that such novel adjuvants may indeed be useful; nevertheless, their effect, unlike that of gD chimeric antigens, would be systemic and thus carry a higher likelihood of unwanted side effects.

Example 12

In Vitro Characterization of the Vaccine Vectors

Figure 27A:
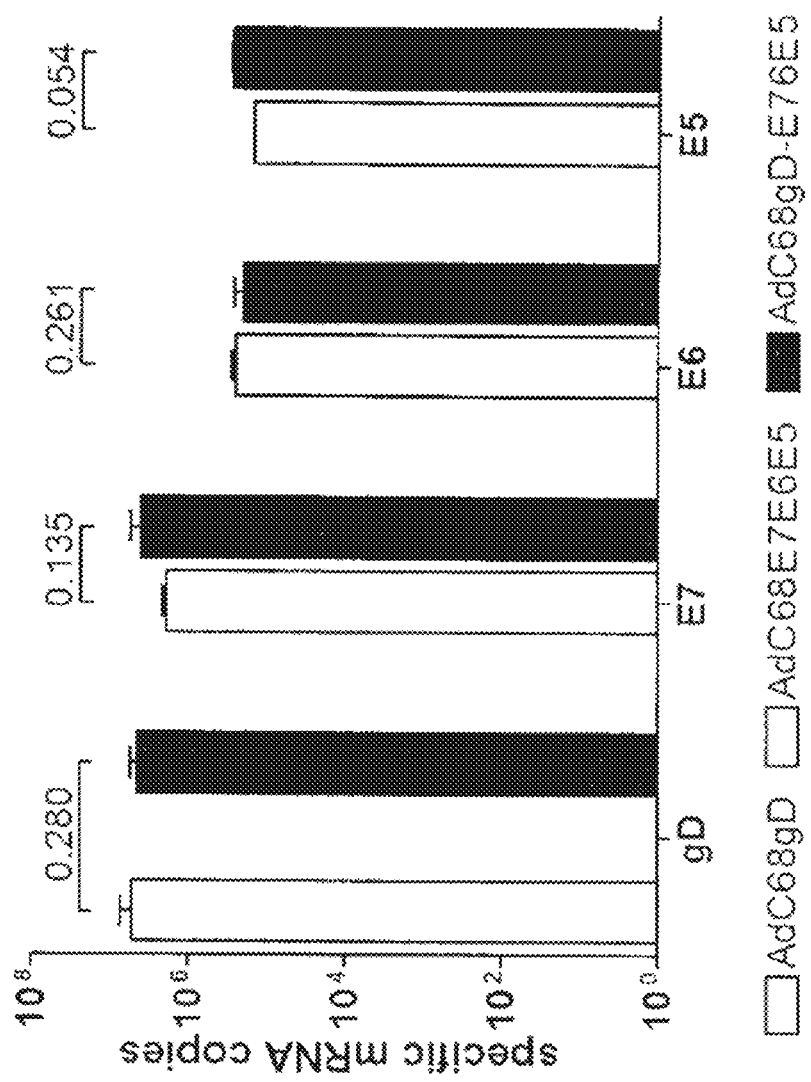
FIGS. 27A-27B. Quantification of specific mRNA copies and protein expression by cells infected in vitro with AdC68 vectors.
Figure 27B:
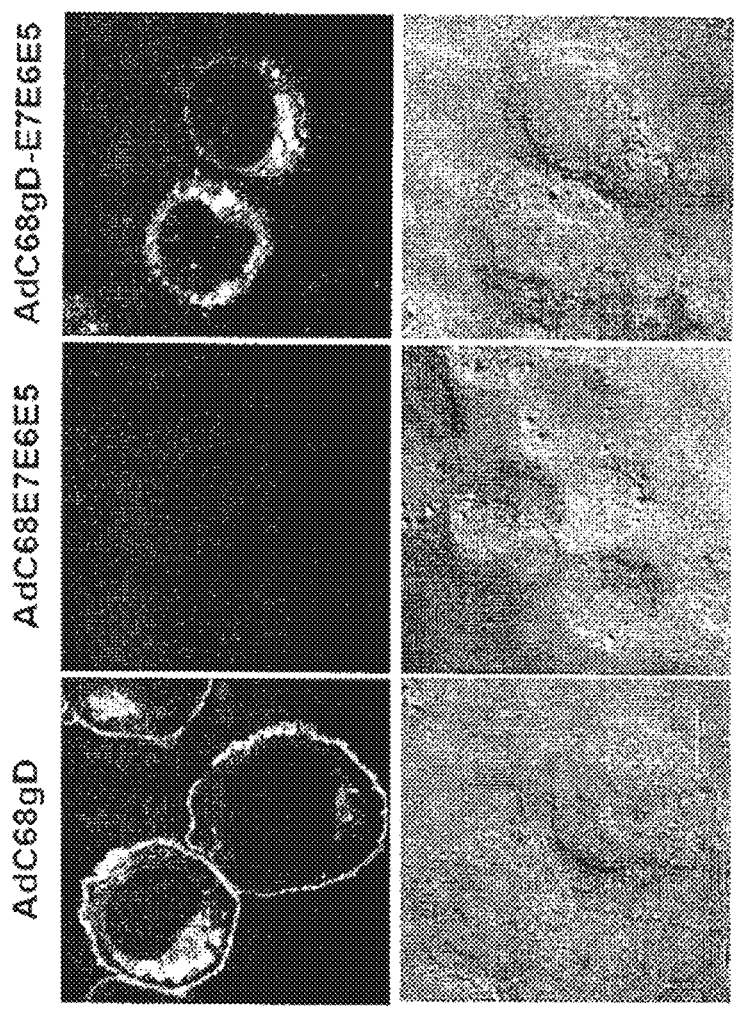

We compared levels of transgene in cells infected in vitro with AdC68 vectors. Total RNA isolated from CHO/CAR cells infected with $10^9$ virus particles (vps) of AdC68gD, AdC68E7E6E5 and AdC68gD-E7E6E5 vectors was reversed transcribed and gD, E7, E6 and E5 specific mRNA were quantified by real-time PCR (FIG. 27A). To minimize inherent differences in RNA isolation procedures, mRNA of a housekeeping gene (GAPDH) was used to normalize the amount of cDNA in each sample. The amount of gD-specific mRNA transcripts in cells infected with AdC68gD-E7E6E5 was not statistically different from that in cells infected with AdC68gD. The mRNA levels of E7, E6 and E5 were also similar in samples infected with AdC68gD-E7E6E5 and AdC68E7E6E5. Protein expression in cells infected with AdC68 vectors was evaluated by immunofluorescence with a monoclonal antibody (MAb) against gD (FIG. 27B). CHO/CAR cells infected with AdC68gD expressed gD mainly on their surface although some of the protein could be detected within the cells. Cells infected with AdC68E76E5 did not stain with the gD-specific MAb. In cells infected with AdC68gD-E7E6E5, gD was mainly detected within the cells; levels of gD on the cell surface were markedly reduced when compared to those on cells infected with AdC68gD. The lower levels of cell surface expression of the chimeric protein might be due to inefficient secretion, rapid re-internalization of gD-E7E6E5 or accelerated proteolytic degradation.

Example 13

E7-Specific CD8+ T Cell Responses Induced by AdC68 Vectors

Figure 28A:
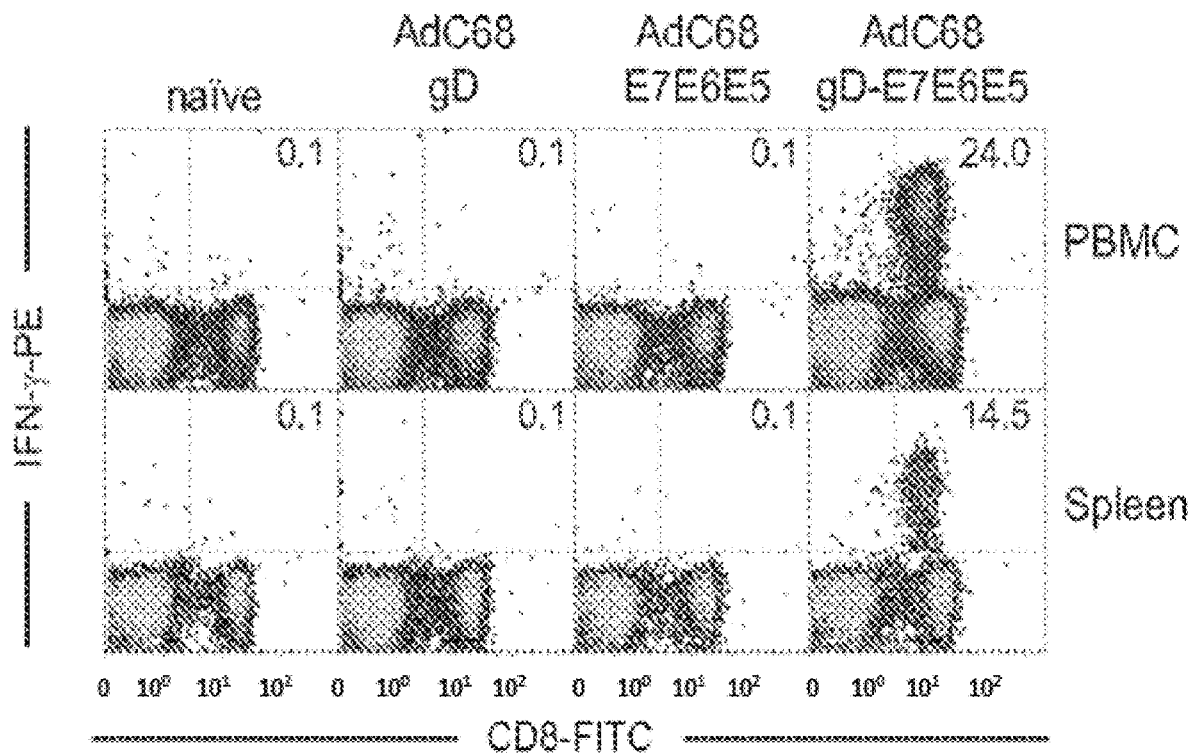
FIGS. 28A-28C. Intracellular IFN-γ staining of E7-specific CD8⁺ T cells from mice immunized with AdC68 and DNA vectors.
Figure 28B:
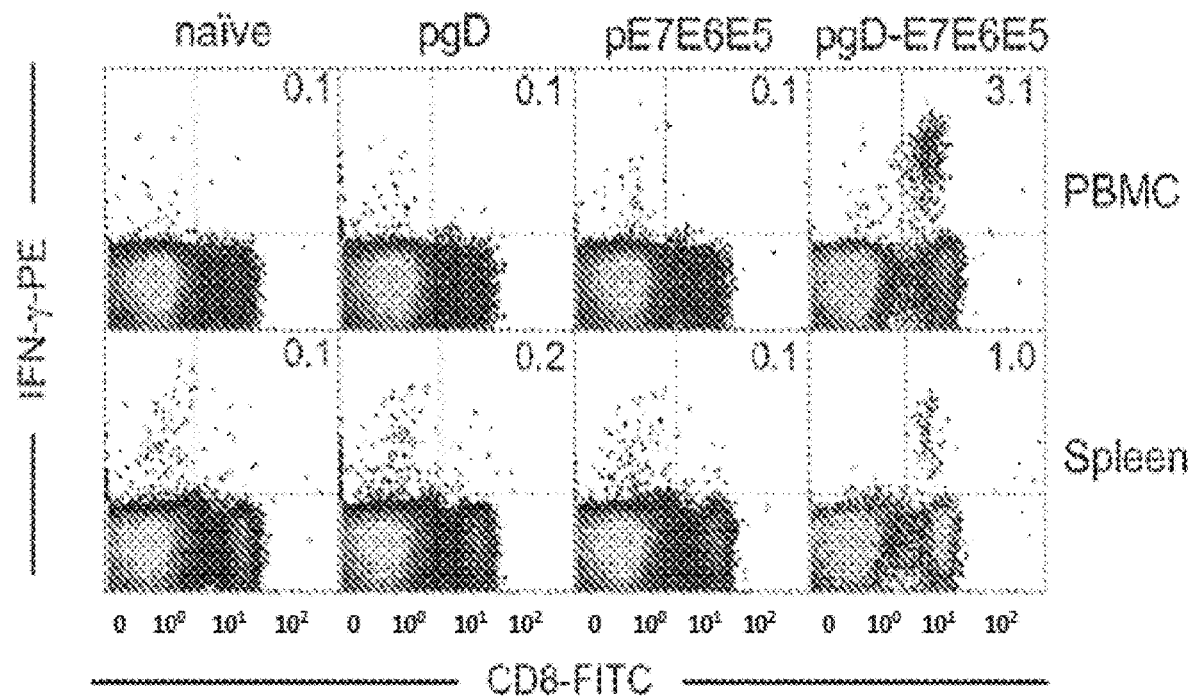

The induction of immune responses by the gD-E7E6E5 expressed by AdC68 and DNA vectors were described above. Here, we confirmed our studies by testing splenocytes and PBMCs from mice immunized with either AdC68 or DNA by ICS for frequencies of CD8+ T cells producing IFN-γ in response to a peptide expressing the immunodominant epitope of E7 (FIGS. 28A and 28B, respectively). We confirm that immunization with AdC68gD-E7E6E5 induced a potent E7-specific CD8+ T cell response detectable from spleens and blood while no specific CD8+ T cell response was found upon immunization with AdC68gD or AdC68E7E6E5. Also, DNA vaccines carrying either the E7E6E5 fusion protein alone or gD failed to induce CD8+ T cells to E7, while such cells were elicited by the DNA vaccine expressing E7E6E5 within gD.

Figure 28C:
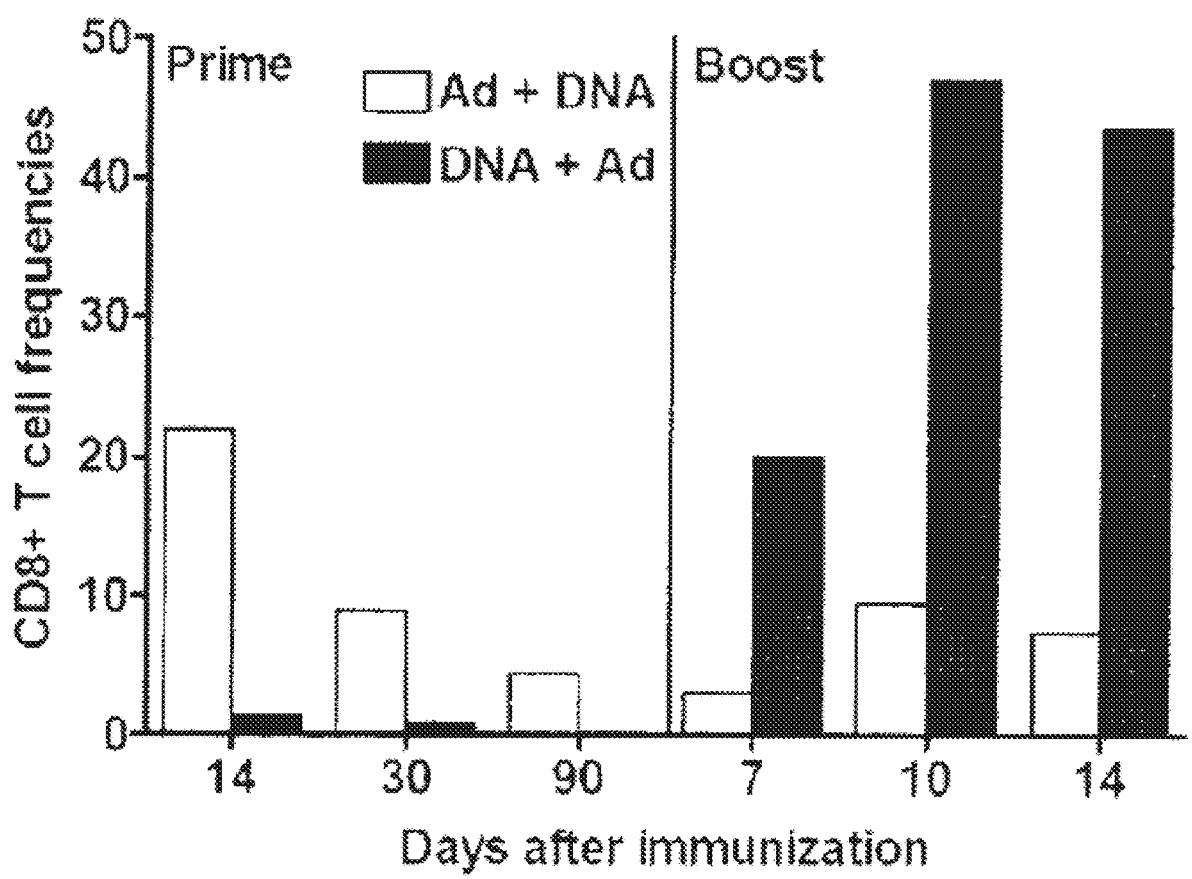

To investigate whether the CD8+ T cell response induced by AdC68gD-E7E6E5 could be enhanced further, AdC68gD-E7E6E5 was tested in a prime and boost regimen with the DNA vaccine expressing the same transgene product (FIG. 28C). Groups of mice were primed with the DNA vaccine and then boosted with the AdC68 vector 90 days later. In other animals the order of the vaccines was reversed. T cell frequencies were tested from blood 14, 30 and 90 days after priming and then on days 7, 10 and 14 after the boost. After priming, the AdC68 vector induced higher frequencies of E7-specific CD8+ T cells compared to the DNA vaccine. Upon booster immunization the AdC68 prime DNA boost regimen performed poorly, and although CD8+ T cell frequencies increased they remained below the peak frequencies seen upon AdC68 priming. In contrast, in the group primed with the DNA vaccine, a boost with the AdC68 vector induced a pronounced increase in E7-specific CD8+ T cell frequencies.

Once we defined the most efficient prime boost regimen, we tested whether the DNA vaccine or the AdC68E7E6E5 vector could prime or boost a CD8+ T cell response to E7. Mice primed with the DNA vaccines carrying E7E6E5 with or without gD were boosted 90 days later with either AdC68E7E6E5 or AdC68gD-E7E6E5, respectively. See Table 5, below.

TABLE 5

AdC68 vectors boost after prime with DNA vaccines.

| Prime [a] | Percentage of IFN-γ CD8+ cells over total CD8+ cells [b] Boost [c] | | |
|---|---|---|---|
| | No Boost | AdC68E7E6E5 | AdC68gD-E7E6E5 |
| No prime | 0.1 | 0.1 | 21.9 |
| pE7E6E5 | 0.1 | 0.1 | 21.2 |
| pgD-E7E6E5 | 0.3 | 2.5 | 47.4 |

[a] Mice were primed i.m. immunized with 100 μg of DNA vaccine.
[b] Frequencies of E7-specific CD8+ T cells over all CD8+ cells were determined 10 days after boost.
[c] Mice were boosted with 5 × $10^{10}$ vps of AdC68 vectors 60 days after prime.

Ten days after immunization with AdC68gD-E7E6E5, E7-specific CD8+ T-cell frequencies were similar in mice primed with pE7E6E5 and unprimed control mice, indicating that the DNA vaccine expressing the oncoproteins of HPV-16 was non-immunogenic. Again, mice primed with pgDE7E6E5 and boosted with AdC68gD-E7E6E5 developed high frequencies of E7-specific IFN-γ-producing CD8+ T cells. A low but significant increase in E7-specific CD8+ T cells was observed in mice primed with the DNA vaccine expressing gD-E7E6E5 and then boosted with AdC68E7E6E5, indicating that within this more immunogenic vaccine vehicle, the oncoproteins could trigger expansion of a memory response.

To test whether the effect of gD required that the antigen was expressed within gD or if concomitant presence of gD and the antigen sufficed, we immunized mice with a mixture of equal doses of AdC68gD and AdC68E7E6E5. This mixture failed to elicit a detectable E7-specific CD8+ T cell response, suggesting that the immunopotentiating effect of gD requires that the antigen is expressed within gD or that the same cells that express gD have to express the antigen.

Example 14

Dose Response Curve of the CD8+ T Cell Response to AdC68gD-E7E6E5

Figure 29:
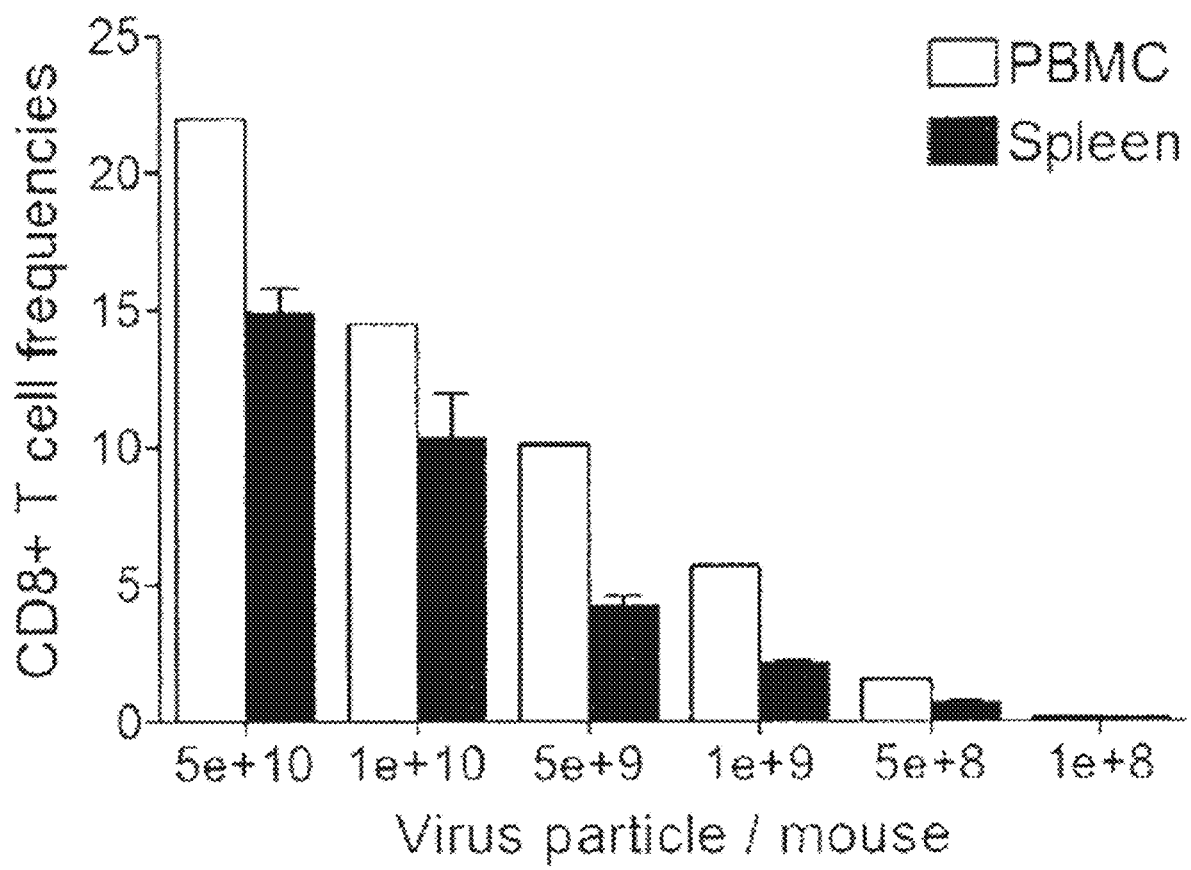
FIG. 29. Dose-response of the CD8+ T cell response to AdC68gD-E7E6E5. Frequencies of IFN-γ-producing E7-specific CD8⁺ T cells in spleens and PBMCs induced by $5 \times 10^{10}$ to $1 \times 10^8$ vp/animal of AdC68gD-E7E6E5 vector were determined as described on legend to FIGS. 28A-28C.

In humans, Ad vectors cause dose limiting toxicity, as has been established for E1-deleted AdHu5 vector tested as vaccine carriers for antigens of HIV-1 in clinical trials (Kresge, K. J et al., 2005). Although the AdC68 vector has not yet undergone clinical testing, we anticipate that this vector would also cause significant toxicity if used at high doses. We therefore tested the E7-specific CD8+ T cell response elicited by varied doses of AdC68gD-E7E6E5 (FIG. 29A).

Mice were immunized i.m. with $1 \times 10^8$ to $5 \times 10^{10}$ vps of AdC68gD-E7E6E5. Frequencies of E7-specific CD8+ T cells were measured 10 days later from blood and spleens. The specific CD8+ T response declined with decreasing doses of adenovirus vector. A response could still be detected upon immunization with $5 \times 10^8$ vps of the vaccine

Example 15

AdC68gD-E7E6E5 Protects Against Challenge with an E7-Expressing Tumor Cell Line

Figure 30A:
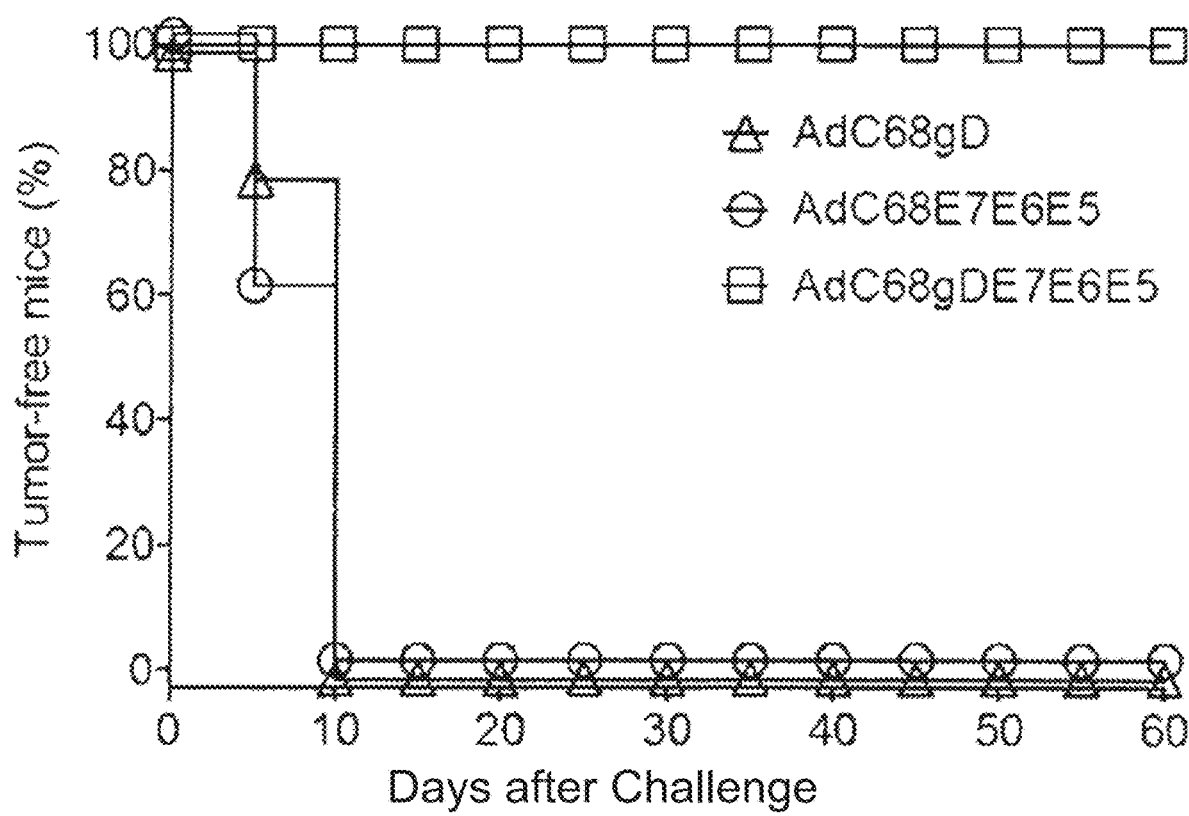
FIGS. 30A-30B. Anti-tumor effects of AdC68 vectors against TC-1 cell challenge.

To formally demonstrate efficacy of AdC68gD-E7E6E5 we conducted challenge experiments with the TC-1 cell line. To determine the effectiveness of the AdC68 vector-induced immune response in causing regression of already established tumors, groups of C57Bl/6 mice were first injected with TC-1 cells then vaccinated 5 days later with AdC68gD, AdC68E7E6E5, or AdC68gD-E7E6E5 (FIG. 30A). Mice immunized with AdC68gD-E7E6E5 rejected the tumors and remained tumor-free for at least 60 days after challenge. In contrast, mice immunized with AdC68gD and AdC68E7E6E5 showed progressive growth of the TC-1 tumors.

Figure 30B:
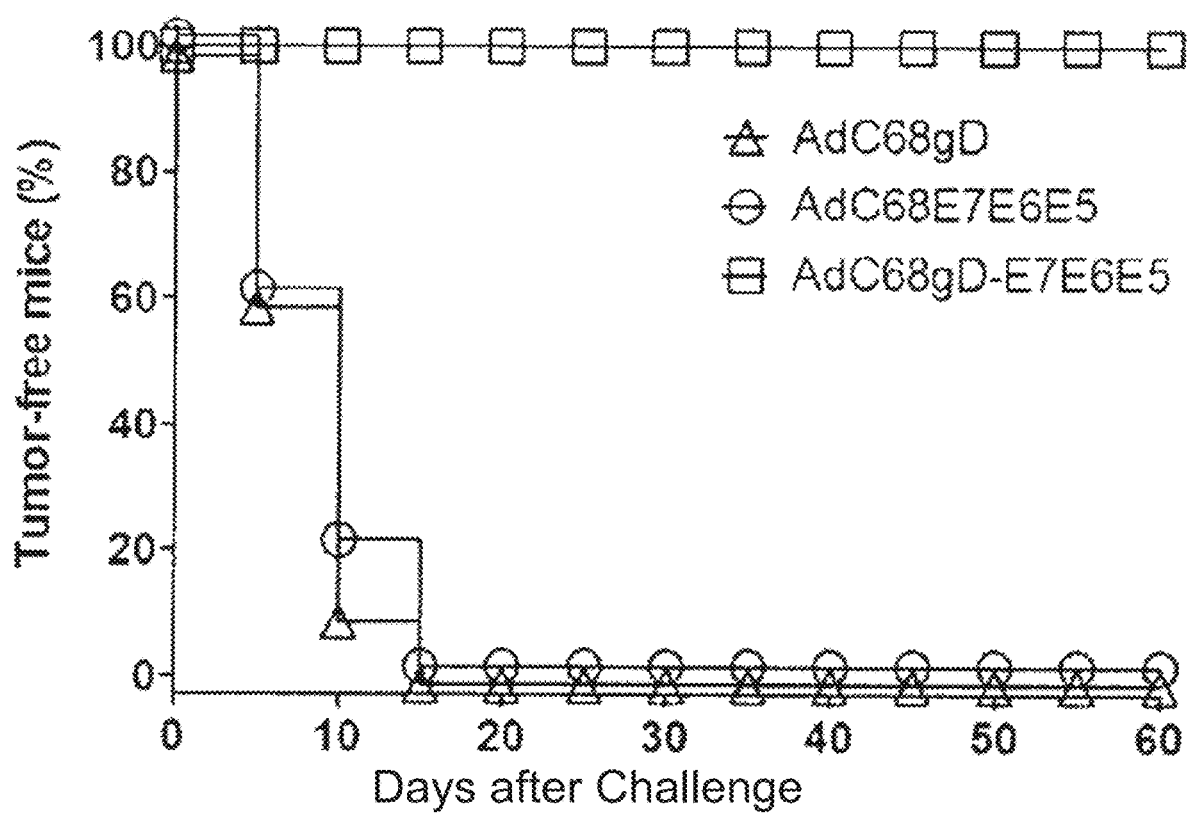

Induction of long-term memory by a therapeutic vaccine is advantageous, since longevity of T cells may prevent resurgence of virus-infected cells that escape the initial wave of the immune response. Recently, we showed that E7-specific CD8$^+$ T response in mice immunized with a single dose of AdC68gD-E7E6E5 was detected over a year after immunization. We challenged mice that had been vaccinated 1 year earlier with AdC68gD-E7E6E5, AdC68gD or AdC68E7E6E5 with TC-1 cells (FIG. 30B). Mice immunized with AdC68gD-E7E6E5 were protected against TC-1 challenge given one year later, while mice injected with AdC68gD or AdC68E7E6E5 developed tumors after challenge.

Figure 31A:
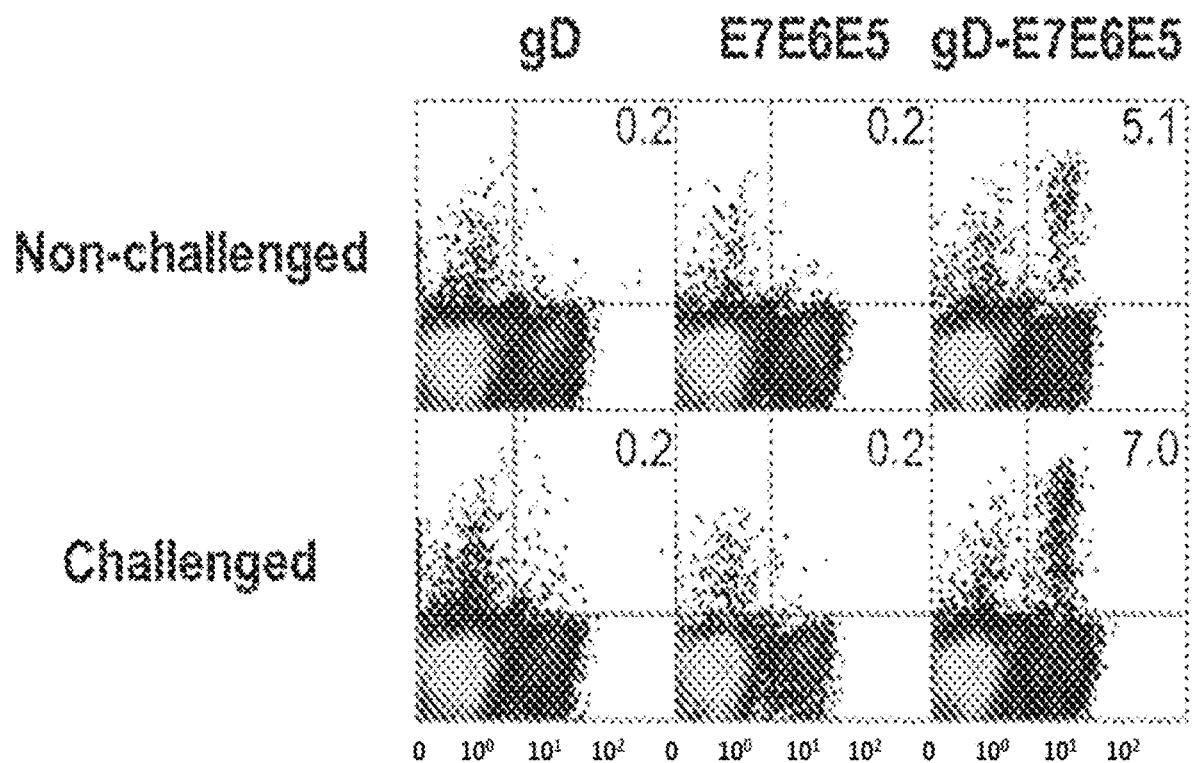
FIGS. 31A-31B. CD8⁺ T cell response after challenge with TC-1 in mice vaccinated one year earlier. One year after vaccination with AdC68 vectors expressing either gD, E7E6E5 or gD-E7E6E5, mice were challenged with TC-1 cells and 10 days later E7-specific frequencies of E7-specific CD8+ T cells were determined.
Figure 31B:
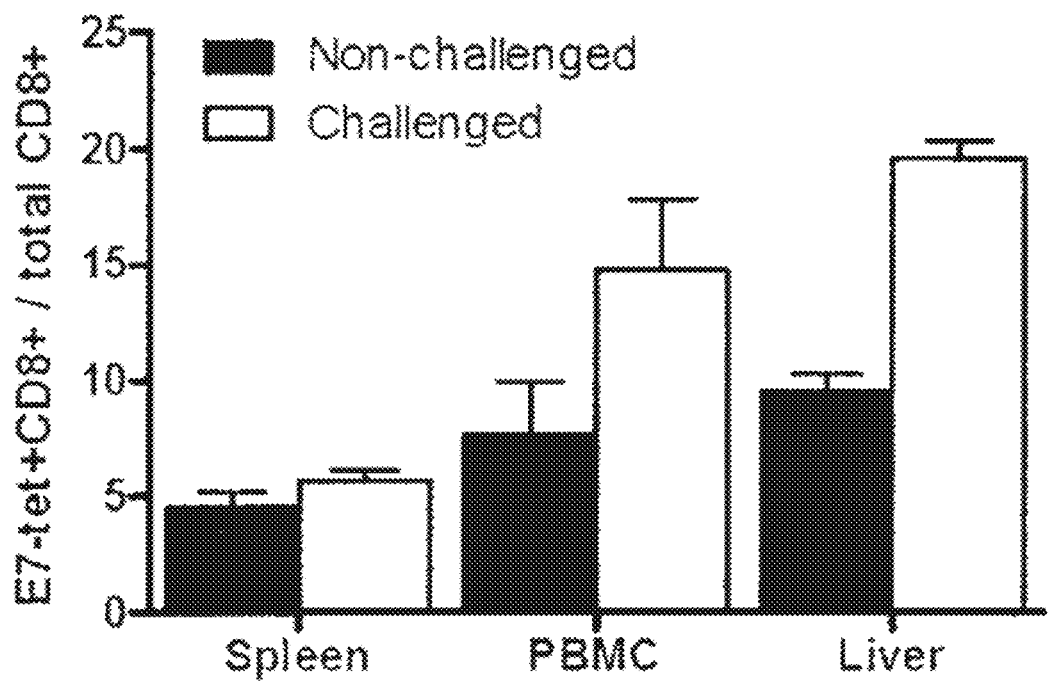
Figure 32A:
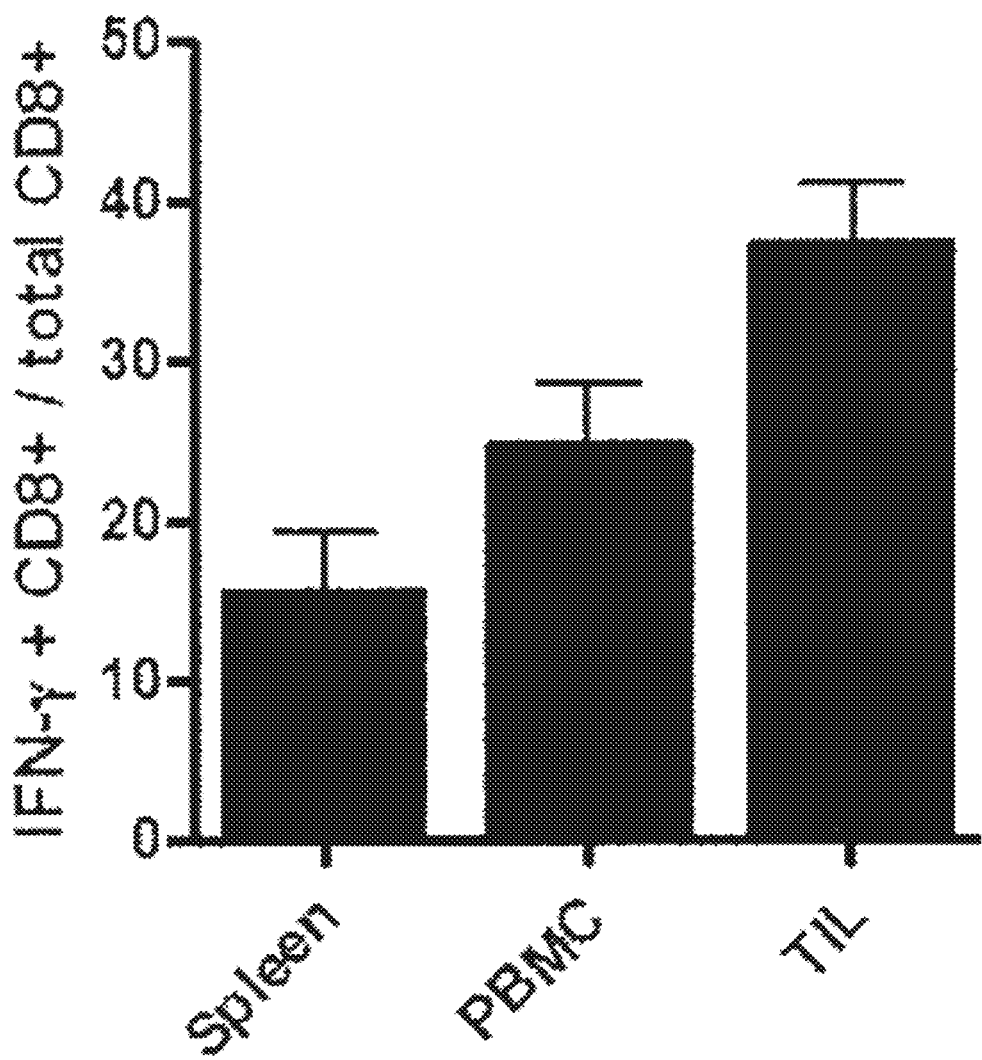
Figure 32B:
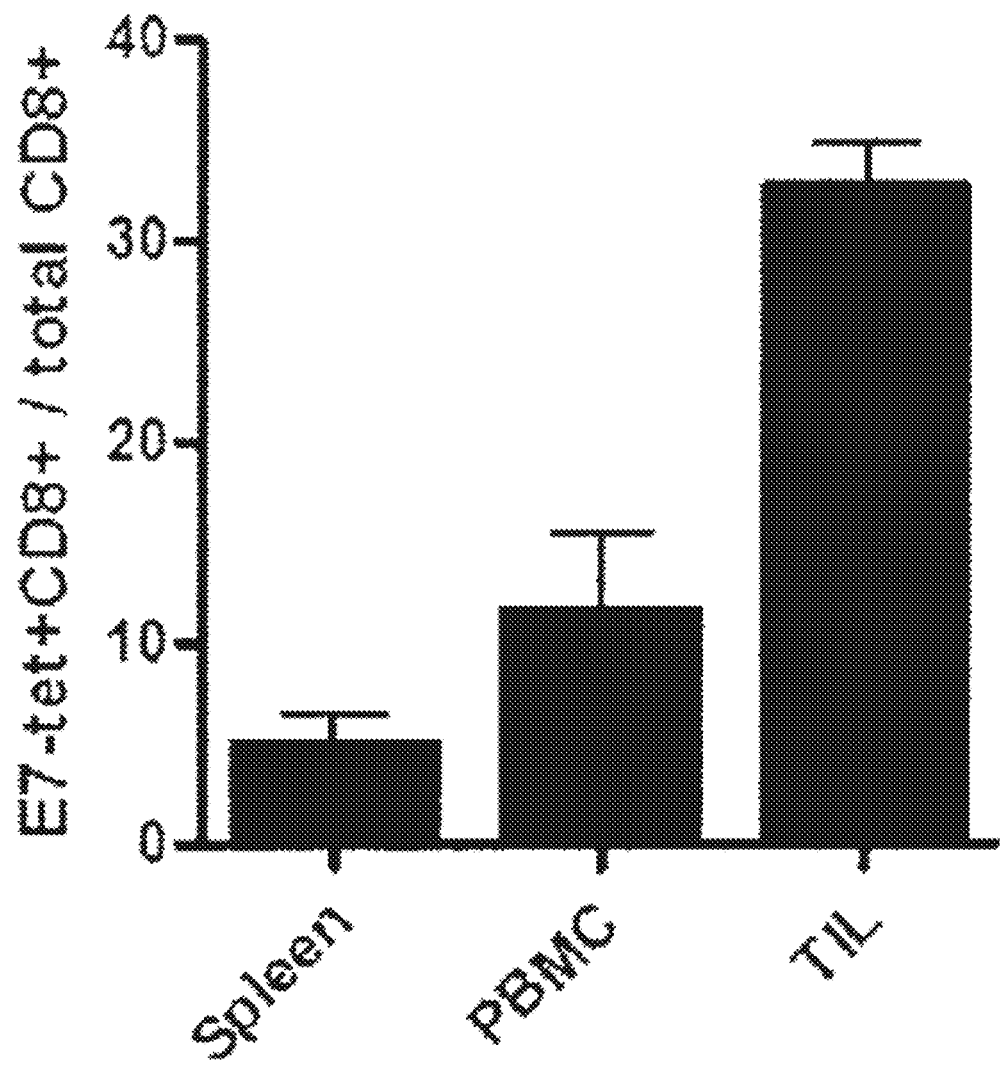

To determine if tumor cell challenge boosted the vaccine-induced E7-specific CD8$^+$ T cell response, we investigated E7-specific CD8$^+$ T cell response after challenge (FIGS. 31A-31B). Frequencies of E7-specific CD8$^+$ T cells as detected by E7/D$^b$ tetramers increased slightly in mice that were challenged compared to those that had only been vaccinated (FIGS. 31A and 31B).

Example 16

Phenotypic Profile of E7-Specific CD8$^+$ T Cells

We analyzed CD8$^+$ T cells from blood, spleens and tumors of vaccinated mice. Mice were immunized with AdC68gD, AdC68E7E6E5 or AdC68gD-E7E6E5. They were challenged 10 days later with TC-1 cells in matrigel. Lymphocytes were isolated 3 days later from spleens, blood and tumors. A pronounced cellular infiltrate was seen in tumors from AdC68gD-E7E6E5 vaccinated animals while comparatively few cells could be isolated from tumors of the other groups. We therefore isolated cells from additional mice on day 10 after challenge. At this time point there was a pronounced infiltrate in the tumors of AdC68gD and AdC68E7E6E5 vaccinated mice. In mice vaccinated with AdC68gD-E7E6E5, tumors had resolved and only a few cells could be recovered. We therefore compared cells isolated from day 3 tumors from AdC68gD-E7E6E5 vaccinated mice with those isolated on day 10 from tumors of AdC68gD and AdC68E7E6E5 vaccinated mice. In addition we analyzed PBMCs and splenocytes harvested on the corresponding days.

Tumors from mice vaccinated with AdC68gD-E7E6E5 had frequencies of E7-specific CD8$^+$ T cells that exceeded those in spleens or blood of the same mice, indicating a rapid recruitment or retention of E7-specific CD8$^+$ T cells within the tumors. E7-specific CD8$^+$ T cells from spleens, blood and tumors were analyzed phenotypically for CD44, CD62L, CD27, Bcl2, BTLA, CTLA-4 and PD-1 in comparison to tetramer negative (tet-) T cells from naive mice or mice immunized with AdC68gD or AdC68E7E6E5. The phenotypic profiles of tet-T cells from either of these groups were identical. E7-specific CD8$^+$ T cells from spleens and blood up-regulated CD44 and down-regulated CD62L, CD27, Bcl2 and BTLA. There was no change of CTLA-4 or PD1 expression compared to tet-CD8$^+$ T cells. CD8$^+$ T cells isolated from tumors showed a distinct phenotype. Tee CD8$^+$ cells up-regulated CD44 and down-regulated CD62L, CD27 and BTLA. Unlike cells from blood and spleens, they failed to down-regulate Bcl2 and strongly upregulated CTLA-4 and PD1, two molecules involved in negative immunoregulation.

Example 17

AdC68gD-E7E6E5 Induces an E7-Specific CD8$^+$ T Cell Response in E7-Transgenic Mice Women with HPV-16-associated cancers are expected to respond poorly to E7 as a progressing tumor would impair the adaptive immune response directed against its antigen. To determine if AdC68gD-E7E6E5 induces an E7-specific CD8$^+$ T cell response in mice that are tolerant to E7 we tested transgenic (tg) mice that constitutively express E7 under a tissue-specific promoter in the thyroid. These mice develop with age large goiters and thyroid carcinomas. E7-tg mice as well as age-matched control mice were vaccinated at one year of age with 5×10$^{10}$ vps of AdC68gD-E7E6E5 or as a control with AdC68gD or AdC68E7E6E5. Ten days later lymphocytes were isolated from blood and spleens.

Figure 33A:
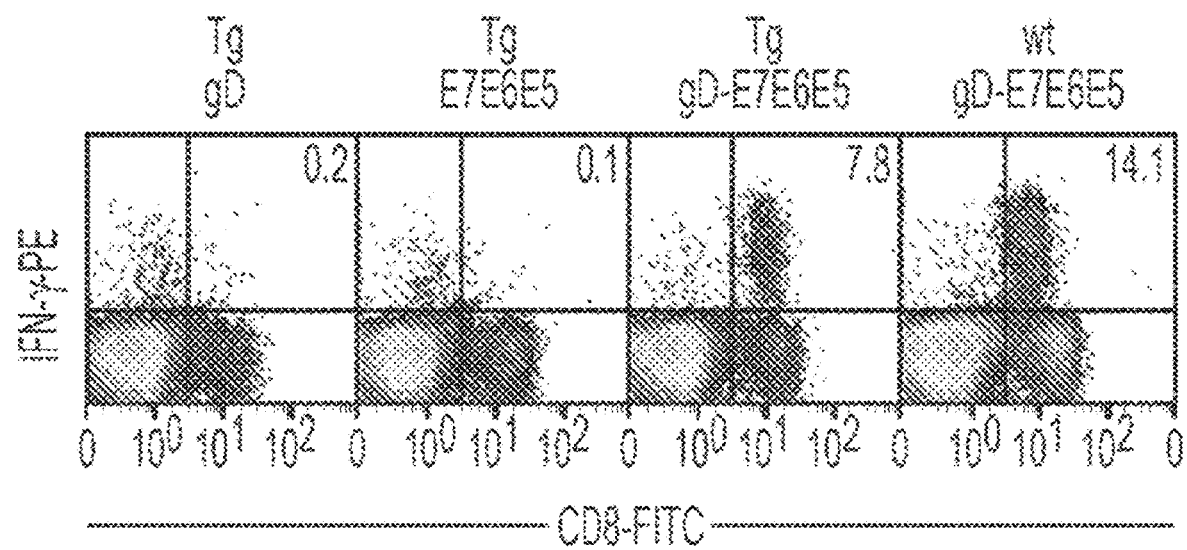
Figure 33B:
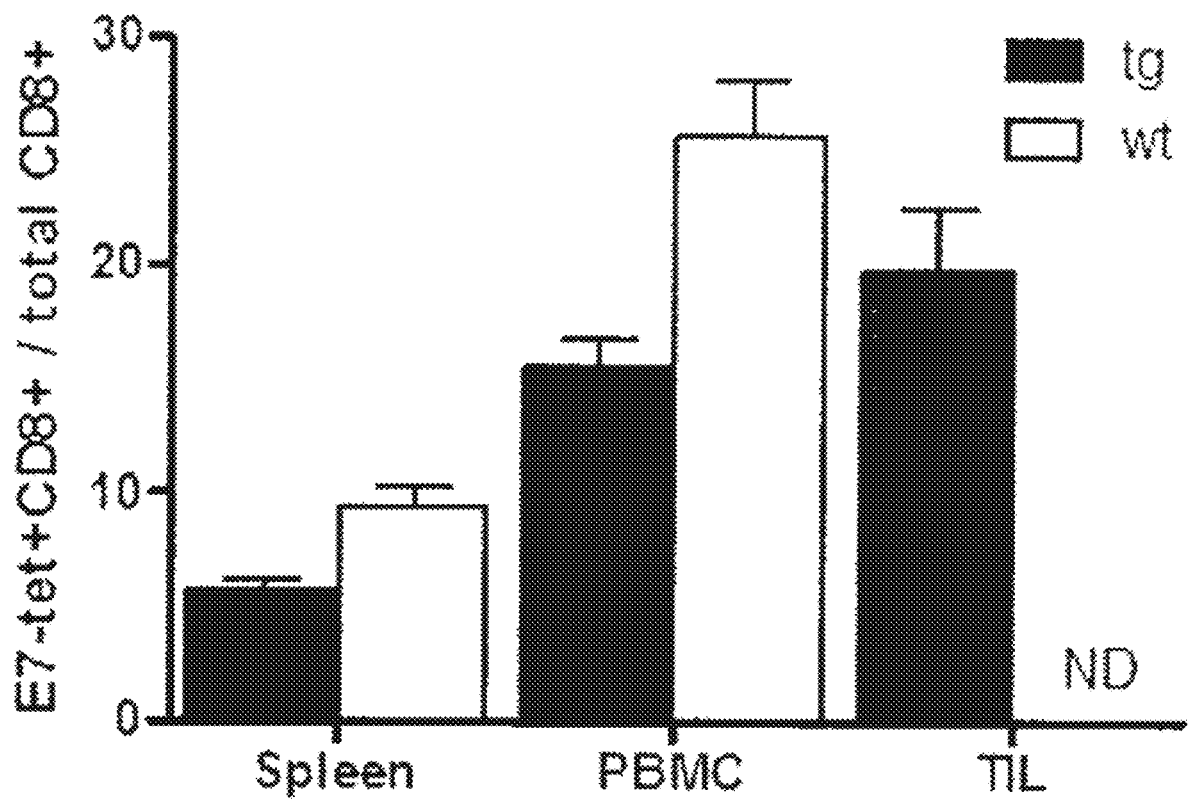

E7-tg mice had markedly enlarged thyroids and lymphocytes were also isolated from their thyroids. The thyroids of wild-type mice were comparatively small and we were unsuccessful to obtain lymphocytes from them. T cells from individual animals were tested for frequencies of E7-specific CD8$^+$ T cells. Mice failed to develop E7-specific CD8$^+$ T cells upon vaccination with AdC68gD or AdC68E7E6E5 (FIG. 33A). Both E7-tg and wild-type mice developed vigorous responses in blood and spleens to E7 upon vaccination with AdC68gD-E7E6E5. Responses were slightly higher in samples from wild-type mice compared to those from E7-tg mice. This difference was statistically not significant by ICS although it was significant upon analysis by tetramer staining. E7-specific CD8$^+$ T cells could also be detected at high frequencies in the thyroid of AdC68gD-E7E6E5-vaccinated E7-tg mice. E7-specific CD8$^+$ T cells isolated from blood and spleen of wild-type and E7-tg mice as well as from thyroids of E7-tg mice were analyzed for expression of phenotypic markers.

CD8$^+$ T cells from naïve E7-tg mice isolated from spleens, blood or thyroids were analyzed for comparison. In spleen and blood expression of CD62, CD127, BcL2, BTLA, and CTLA-4 on E7-specific CD8$^+$ T cells from E6/E7-tg and wild-type mice were indistinguishable. CD27, CD44 and PD-1 were slightly higher on E7-specific CD8$^+$ T cells isolated from blood and to a lesser degree from spleens of E7-tg mice. E7-specific CD8$^+$ T cells isolated from the thyroids expressed markedly higher levels of CD44, CD27 and PD-1 in comparison to CD8$^+$ T cells isolated from the thyroids of naïve E7-tg mice. The other markers were similar to those seen on E7-specific T cells from blood and spleens. None of the CD8$^+$ T cells isolated from the thyroids of naïve E7-tg mice stained with the tetramer to E7, phenotypes of the vaccine-induced E7-specific CD8+ T cells could thus not be compared to phenotypes of T cells induced by the transgenic E7 protein.

Discussion of Examples 12-17

A preventative vaccine for HPV-16 based on L1 virus like particles, which induces neutralizing antibodies, has recently been licensed by FDA and has been recommended for use in teenage girls and young women. Once an infection has occurred, however, neutralizing antibodies do not affect viral clearance nor do they inhibit development of malignancies. Consequently, women with humoral immunodeficiency do not have an increased susceptibility to cervical cancer, while women with cell-mediated immunodeficiency, such as HIV-1-infected patients, renal transplant patients or patients with genetic T cell deficiencies, have increased incidence rates (Moscicki et al., *J Infect Dis* 2004; 190:37-45; Matas et al., *Lancet* 1975; 1:883-6; Frisch et al., *J Natl Cancer Inst* 2000; 92:1500-10; Lowy et al., *J Natl Cancer Inst* 2003; 95:1648-50. This together with extensive studies in animal models and clinical trials (reviewed in Galloway, *Lancet* Infect Dis 2003; 3:469-75) implicates a crucial role for T cells in eliminating cells persistently infected with oncogenic types of HPVs.

The vaccine described here expressed three of the oncoproteins of HPV-16, i.e., E7, E6 and E5 to broaden responses in human outbred populations. Mice of the $H-2^b$ haplotype respond to a low affinity epitope of E7, but according to our results fail to develop CD8+ T cells to E6. Our CD8+ T cell analyses thus focused on responses to E7. To enhance immune responses we incorporated the oncoproteins into gD of HSV-1 which binds to the herpes virus entry mediator (HVEM) (Montgomery et al., Cell 1996; 87:427-36; Whitbeck et al., J Virol 1997; 71:6083-93). HVEM, which is expressed on dendritic cells, is a member of the tumor-necrosis factor receptor (TNFR) family and interacts with LIGHT (Marsters et al., J Biol Chem 1997; 272:14029-32; Granger & Rickert, Cytokine Growth Factor Rev 2003; 14:289-96) and lymphotoxin-α (LT-α) (Mauri et al., Immunity 1998; 8:21-30; Sarrias et al., Mol Immunol 2000; 37:665-73). Also, HVEM binds to B and T lymphocyte attenuator (BTLA), a recently described member of the B7-family (Gonzalez et al., Proc Natl Acad Sci USA 2005; 102:1116-21; Sedy et al., Nat Immunol 2005; 6:90-8). The HVEM-BTLA interaction inhibits T cell activation in vitro thus defining these molecules as part of an inhibitory pathway (Sedy et al., 2005). Expression of BTLA is upregulated on tumor-infiltrating T cells as was shown in cancer patients (Wang et al., Tissue Antigens 2007; 69:62-72). HSV-1 gD competes with BTLA for binding to HVEM (Compaan et al., J Biol Chem 2005; 280:39553-61) and would thus be expected to enhance activation of naïve T cells by blockade of this negative immunoregulatory pathway. Recently, we showed that viral antigens expressed within gD induced CD8+ T and B cell responses to the antigens that are far more potent than those elicited by the same antigen expressed without gD.

Our data confirm a very strong increase of CD8+ T cell responses to E7 expressed within HSV-1 gD. Responses to E7 expressed by the DNA vaccine or the AdC68 vector without gD were below the level of detection, while E7 expressed within gD induced frequencies of E7-specific CD8+ T cells of 1-3% upon DNA vaccination and 10-24% upon Ad vector immunization. As expected, responses were markedly higher upon vaccination with the AdC68 vector than the DNA vaccine. Most of our studies therefore focused on the AdC68 vector vaccine. Mice vaccinated with AdC68gD-E7E6E5 were completely protected against challenge with the E7 and E6 expressing TC-1 tumor cells given shortly after vaccination or one year later. More importantly, mice with pre-existing TC-1 tumors rejected the tumors upon vaccination and then remained disease-free. Vaccine-induced E7-specific CD8+ T cells rapidly enriched within the TC-1 tumors. Phenotypically E7-specific CD8+ T cells isolated from TC-1 tumors upregulated CD27, CTLA-4 and PD-1 and down-regulated Bcl2, which may have been a consequence of the engagement of their receptors by the tumor cells. Expression of BTLA, which was previously reported to become upregulated on TILs cells in humans, was not increased on E7-specific CD8+ T cells isolated from TC-1 tumors.

Numerous studies have shown efficacy of HPV-16 E7 vaccines against TC-1 tumors. Transplantable tumors grow very rapidly in mice and vaccines are thus applied before or shortly after challenge. At this early stage, T cells to the tumor antigens are probably not yet compromised. We therefore tested AdC68gD-E7E6E5 in E7-tg mice, which express the oncoprotein under a tissue specific promoter within their thyroid. Listeria based E7 vaccines have been tested in E6/E7-tg mice in which the transgenes were similarly expressed with a bovine thyroglobulin promoter (Souders et al., Cancer Immun 2007; 7:2). The Listeria vaccine was shown to induce lower frequencies of E7-specific CD8+ T cells compared to wild-type mice and the average avidity of CD8+ T cells that were induced was ten fold lower than those isolated from wild-type mice. Nevertheless the Listeria vaccine could eradicate 7 day established (5 mm) transplanted tumors in some E6/E7 transgenic mice, albeit at lower frequency than in wild-type mice. We tested AdC68gD-E7E6E5 in one-year-old E7-tg with thyroid hyperplasia. AdC68gD-E7E6E5 induced an E7-specific CD8+ T cell response in the E7-tg mice that was only slightly below that induced in age-matched wild-type mice. The vaccine-induced E7-specific CD8+ T cells infiltrated the thyroid. Phenotypically, the thyroid-infiltrating vaccine-induced E7-specific CD8+ T cells in E7-tg mice showed only minor difference to those isolated from TC-1 tumors and these differences, i.e., an overall decrease in CD44, CD27, Bcl2, and CTLA4 may be a reflection of difference in sampling time rather than T cell functionality. Accordingly E7-specific CD8+ T cells isolated from blood or spleens of vaccinated wild-type or E7-tg mice showed virtually identical phenotypes.

Our studies show that E7 of HPV-16 expressed as a fusion protein together with E6 and E5 within gD induces a robust CD8+ T cell response even in animals with developing E7-associated malignancies. Without further studies directly comparing the effect of similar numbers of E7-specific CD8+ T cells induced by a vaccine expressing E7 without gD to those induced by a vaccine expressing E7 within gD we can only speculate that the high efficacy of the latter is linked to blockade of an immunoinhibitory pathway. The Listeria vector used previously induces frequencies of E7-specific CD8+ T cells that in wild-type mice are comparable in magnitude to those induced by AdC68gD-E7E6E5. In E6/E7-tg mice the Listeria vector induced markedly lower frequencies of T cells (Souders et al., 2007), while the response to AdC68gD-E7E6E5 is only slightly reduced. Although it is tempting to speculate that this is caused by an immunopotentiating effect of gD, other differences in the vaccine delivery vehicles such as their interactions with antigen presenting cells, in addition to differences between the E6/E7 and E7 transgenic mice such as transgene copy number and E7 expression may also have contributed to these results.

Blockade of immunoinhibitory pathways that are upregulated in cancer patients such as regulatory T cells or PD-1 expression on T cells has been shown pre-clinically to increase T cell responses to tumor antigens. In these systems regulatory T cells were depleted or rendered dysfunctional by antibodies and using a similar approach, the PD-1 pathway was blocked by antibodies to PD-1 or its ligand. These interventions, which have shown promise in animal models, exert a global effect on the immune system, which poses the risk of augmenting auto-immune reactivity. In contrast, blockade of the BTLA-HVEM pathway only exerts a local effect on T cells that are being activated to the antigen expressed within gD and should thus not subject patients to unwanted immune responses.

Example 18

Immunization of Rhesus Macaques

Two groups of rhesus macaques (4 per group) are enrolled into the study. Animals are screened for antibodies to AdC68. Only seronegative animals are used. Sera and peripheral PBMCs are harvested 4 and 2 weeks before vaccination and preserved to serve as controls.

Animals are vaccinated once with 500 µg of pgag (group 1) or pgD-gag (group 2). They are boosted 2 months later with $5 \times 10^{10}$ vps of purified and quality controlled AdC68gag (group 1) or AdC68gD-gag (group 2) vector given i.m. in saline. Animals are bled 2, 4, and 8 weeks after priming and 2, 6 and 12 weeks after booster vaccination. PBMCs are tested for T cell responses to a pool of gag peptides by ELISpot for IFN-γ and IL-2 and by ICS for CD3, CD8, CD4, IFN-γ and IL-2 as described (Reyes-Sandoval, et al. J. Virol. 78:7392-7399).

Sera are tested for antibodies to gag (ELISA) and neutralizing antibodies to the vaccine carrier. The experiments are controlled by samples collected prior to vaccination. Animals are euthanized ~4 months after the boost, and lymphocytes are isolated from various compartments (spleen, blood, lymph nodes, liver, intestine) and tested by ELISpot for T cell responses to gag including analyses for IFN-γ, IL-2, TNF-α and MW-1β. In addition they are analyzed by ICS for secretion of IFN-γ and expression of T cell markers (CD3, CD4, CD8, included into each panel), activation (CD69, CD25, CD95, CD71) and proliferation (Ki67) markers, markers that identify T cell subsets (naive, central memory T cells, effector memory T cells and effector T cells) (CD28, CD95, CD45RA, CD62L, CCR7, CD27, CD127); chemokine and homing receptors (CCR5, CCR9, CXCR4, C11a-c, a4b7, CD103, CD49d); and markers indicative for lytic potential (CD107, perforin, granzyme B).

Immunophenotypical studies are performed by multicolor (7-8 colors) flow cytometry on mononuclear cells. The analyses are restricted to compartments that that allow for isolation of sufficient numbers of lymphocytes. The experiment is controlled using cryopreserved splenocytes from sham-vaccinated rhesus.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention.

What is claimed:

1. A method of inducing an immune response comprising providing to a subject in need thereof a vaccine comprising a nucleic acid molecule which encodes a fusion protein, wherein the fusion protein comprises:
   a. a first polypeptide segment comprising at least amino acids 1-240 of a mature Herpes simplex virus (HSV) glycoprotein D, wherein the first polypeptide segment does not comprise a full length mature glycoprotein D;
   b. a second polypeptide segment comprising at least one antigen, wherein the at least one antigen is not an HSV glycoprotein D antigen, wherein the N terminus of the second polypeptide segment is linked to the C terminus of the first polypeptide segment; and
   c. a third polypeptide segment comprising a C terminal portion of the HSV glycoprotein D, wherein the N terminus of the third polypeptide segment is linked to the C terminus of the second polypeptide segment.

2. The method of claim 1, wherein the HSV is selected from the group consisting of HSV-1 and HSV-2.

3. The method of claim 2, wherein the first polypeptide segment comprises an amino acid sequence selected from the group consisting of:
   a. amino acids 26-265 of SEQ ID NO:27;
   b. amino acids 26-265 of SEQ ID NO:29;
   c. amino acids 1-244 of the glycoprotein D;
   d. amino acids 1-288 of the glycoprotein D; and
   e. amino acids 1-294 of a mature HSV glycoprotein D with the exception that amino acid 294 is alanine instead of tryptophan.

4. The method of claim 3, wherein the first polypeptide segment is encoded by a nucleic acid sequence comprising nucleotides 76-795 of SEQ ID NO:26; or nucleotides 350-1069 of SEQ ID NO:28.

5. The method of claim 1, wherein the nucleic acid molecule is in a viral vector.

6. The method of claim 1, wherein the nucleic acid molecule is naked DNA.

7. The method of claim 1, wherein the nucleic acid molecule is in a bacterial vector.

8. The method of claim 1, wherein the second polypeptide segment comprises the HPV E5 protein, the HPV E6 protein, and the HPV E7 protein.

9. The method of claim 1, wherein the third polypeptide segment comprises the transmembrane domain of the HSV glycoprotein D.

* * * * *